US012747447B2

(12) United States Patent
Nakamura et al.

(10) Patent No.: US 12,747,447 B2
(45) Date of Patent: Sep. 29, 2026

(54) TRANSFORMED PLANT HAVING BLUE FLOWER COLOR, AND METHOD FOR CREATING SAME

(71) Applicant: Suntory Holdings Limited, Osaka (JP)

(72) Inventors: Noriko Nakamura, Soraku-gun (JP); Naoko Okitsu, Soraku-gun (JP); Yoshikazu Tanaka, Soraku-gun (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 16/753,110

(22) PCT Filed: Oct. 2, 2018

(86) PCT No.: PCT/JP2018/036935
§ 371 (c)(1),
(2) Date: Apr. 2, 2020

(87) PCT Pub. No.: WO2019/069946
PCT Pub. Date: Apr. 11, 2019

(65) Prior Publication Data

US 2020/0283782 A1 Sep. 10, 2020

(30) Foreign Application Priority Data

Oct. 3, 2017 (JP) ................................ 2017-193480

(51) Int. Cl.

| | |
|---|---|
| ***C12N 15/82*** | (2006.01) |
| ***C12N 9/10*** | (2006.01) |
| ***C12N 9/88*** | (2006.01) |
| ***C12N 15/52*** | (2006.01) |

(52) U.S. Cl.
CPC ......... *C12N 15/825* (2013.01); *C12N 9/1007* (2013.01); *C12N 9/88* (2013.01); *C12N 15/52* (2013.01); *C12Y 101/01001* (2013.01); *C12Y 114/11022* (2013.01); *C12Y 114/13088* (2013.01)

(58) Field of Classification Search
None
See application file for complete search history.

(56) References Cited

U.S. PATENT DOCUMENTS

| | | | |
|---|---|---|---|
| 2007/0033674 A1 | 2/2007 | Brugliera et al. | |
| 2010/0281575 A1 | 11/2010 | Tanaka et al. | |
| 2014/0033369 A1 | 1/2014 | Tanaka et al. | |
| 2015/0074855 A1* | 3/2015 | Tanaka ............... | C12N 15/8205 800/282 |
| 2020/0325486 A1 | 10/2020 | Noda et al. | |

FOREIGN PATENT DOCUMENTS

| | | |
|---|---|---|
| CN | 101679972 A | 3/2010 |
| CO | 20180011157 A2 | 2/2019 |
| WO | WO-2012/096307 A1 | 7/2012 |

OTHER PUBLICATIONS

Hicks and Edwards. "Metabolic engineering of the flavone-C-glycoside pathway using polyprotein technology". Metabolic Engineering. 16: 11-20. (Year: 2013).*

Nakamura (Nakamura et al. "Flower color modification in Rosa hybrida by expressing the S-adenosylmethionine: anthocyanin 3',5'-O-methyltransferase gene from Torenia hybrid". Plant Biotechnology. 32: 108-117. Feb. 5, 2015) (Year: 2015).*

Brazier-Hicks and Edwards. "Metabolic engineering of the flavone-C-glycoside pathway using polyprotein technology". Metabolic Engineering. 16: 11-20. (Year: 2013).*

Casas et al. "Flavone-rich maize: an opportunity to improve the nutritional value of an important commodity crop". Frontiers in plant science. 5(440): 1-11. (Year: 2014).*

Schmitzer and Stampar. "Changes in Anthocyanin and Selected Phenolics in 'KORcrisett' Rose Flowers Due to Substrate pH and Foliar Application of Sucrose". ISHS Acta Horticulturae 870: V International Symposium on Rose Research and Cultivation. (Year: 2010).*

Yabuya et al. "Anthocyanin-flavone copigmentation in bluish purple flowers of Japanese garden iris (*Iris ensata* Thunb.)". Euphytica. 98:163-167. (Year: 1997).*

Ueyama et al. "Molecular and biochemical characterization of torenia flavonoid 3'-hydroxylase and flavone synthase II and modification of flower color by modulating the expression of these genes". Plant Science. 163(2):253-263. (Year: 2002).*

Katsumoto et al. "Engineering of the Rose Flavonoid Biosynthetic Pathway Successfully Generated Blue-Hued Flowers Accumulating Delphinidin." Plant and Cell Physiology. 48(11)1589-1600. (Year: 2007).*

Akashi et al. NCBI Locus BAA84072. (Year: 1999).*

Ohbayashi, M. Genbank Locus C75A6_CAMME. (Year: 2017).*

Genbank Locus BAP74301.1 (Year: 2014).*

Sasaki et al. FEBS Letters. 589(1):182-187. NCBI Locus F6CGT_GENTR. (Year: 2015).*

Nakatsuka, et al. Molecular Breeding. 17:91-99. (Year: 2006).*

Salehi et al. Int. J Mol Sci. 20(6):1305. (Year: 2019).*

Sasaki et al. FEBS Letters. 589(1):182-187. (Year: 2015).*

NCBI Reference Sequence 004773 (Year: 1993).*

NCBI Reference Sequence: A0A0B6VIJ5. (Year: 2015).*

NCBI Reference Sequence: BAP74301. (Year: 2014).*

NCBI Reference Sequence: BAA84072. (Year: 1999).*

Database UriProtKB, Accession No. Q5VMIO, Definition: RecName: Full=UDP-glucose:2-hydroxyflavanone C-glucosyltransferase; Short=OsCGT, [online], Aug. 30, 2017, URL :<https://www.ncbi,nlm.nih,gov/pre;protein/75287487?sat=46&satkey=124639238>, entire text.

International Search Report mailed Jan. 8, 2019 for PCT/JP2018/036935.

T. Yabuya et al., "Stability of flower colors due to anthocyanin-flavone copigmentation in Japanese garden iris, *Iris ensata* Thunb.," Euphytica 115: 1-5, 2000.

(Continued)

*Primary Examiner* — David R Byrnes
(74) *Attorney, Agent, or Firm* — Banner & Witcoff, Ltd.

(57) ABSTRACT

Provided are a transformed plant having a blue-hued flower color or its inbred or outbred progenies, or their propagules, partial plant bodies, tissues or cells. Delphinidin type anthocyanin and flavone C-glycoside are made to be coexpressed in petals.

18 Claims, 2 Drawing Sheets

Specification includes a Sequence Listing.

(56) References Cited

OTHER PUBLICATIONS

Notice of Reasons for Refusal mailed on Apr. 19, 2022 in Japanese Patent Application No. 2019-546742.
"Sasaki et al., Identification of the glucosyltransferase that mediates direct flavone C-glucosylation in *Gentiana triflora*," FEBS Letters, vol. 589, pp. 182-187, 2015.
"Predicted: *Oryza sativa* Japonica Group UDP-glycosyltransferase 708A6 (LOC9266253), mRNA," Accession: XM_015786198, GenBank, 2 page, Mar. 1, 2016, https://www.ncbi.nlm.nih.gov/nuccore/1002274739?sat=46&satkey=162872110.
Brazier Hicks et al., "The C-Glycosylation of Flavonoids in Cereals", Journal of Biological Chemistry, vol. 284, No. 27, pp. 17926-17934, 2009.
Examiner Requisition mailed Jul. 13, 2023, in Canadian patent application 3,078,387.
Ocean Song from Rosen Tantau (available at <https://rosentantaulatam.com/product/ocean-song/>; last visited Dec. 7, 2023).
Ocean Song from Royal Flowers (available at <https://www.royalflowersgroup.com/product/roses/lavender/oceansong/>; last visited Dec. 7, 2023).
Ocean Song from Rio Roses (available at <https://www.rioroses.com/roses/ocean-song/>; last visited Dec. 7, 2023).
Ocean Song from Eco Roses (available at <https://ecoroses.com.ec/rosevarieties/ocean-song/>; last visited Dec. 7, 2023).

* cited by examiner

SEQUENCE LISTING

```
<160> NUMBER OF SEQ ID NOS: 33

<210> SEQ ID NO 1
<211> LENGTH: 1781
<212> TYPE: DNA
<213> ORGANISM: Viola x wittrockiana

<400> SEQUENCE: 1

gacaacatgg caattctagt caccgacttc gttgtcgcgg ctataatttt cttgatcact      60

cggttcttag ttcgttctct tttcaagaaa ccaacccgac cgctcccccc gggtcctctc     120

ggttggccct tggtgggcgc cctccctctc ctaggcgcca tgcctcacgt cgcactagcc     180

aaactcgcta agaagtatgg tccgatcatg cacctaaaaa tgggcacgtg cgacatggtg     240

gtcgcgtcca cccccgagtc ggctcgagcc ttcctcaaaa cgctagacct caacttctcc     300

aaccgcccac ccaacgcggg cgcatcccac ctagcgtacg gcgcgcagga cttagtcttc     360

gccaagtacg gtccgaggtg gaagacttta agaaaattga gcaacctcca catgctaggc     420

gggaaggcgt tggatgattg ggcaaatgtg agggtcaccg agctaggcca catgcttaaa     480

gccatgtgcg aggcgagccg gtgcggggag cccgtggtgc tggccgagat gctcacgtac     540

gccatggcga acatgatcgg tcaagtgata ctcagccggc gcgtgttcgt gaccaaaggg     600

accgagtcta acgagttcaa agacatggtg gtcgagttga tgacgtccgc cgggtacttc     660

aacatcggtg acttcatacc ctcgatcgct tggatggatt tgcaagggat cgagcgaggg     720

atgaagaagc tgcacacgaa gtttgatgtg ttattgacga agatggtgaa ggagcataga     780

gcgacgagtc atgagcgcaa agggaaggca gatttcctcg acgttctctt ggaagaatgc     840

gacaatacaa atggggagaa gcttagtatt accaatatca aagctgtcct tttgaatcta     900

ttcacggcgg gcacggacac atcttcgagc ataatcgaat gggcgttaac ggagatgatc     960

aagaatccga cgatcttaaa aaaggcgcaa gaggagatgg atcgagtcat cggtcgtgat    1020

cggaggctgc tcgaatcgga catatcgagc ctcccgtacc tacaagccat tgctaaagaa    1080

acgtatcgca aacacccgtc gacgcctctc aacttgccga ggattgcgat ccaagcatgt    1140

gaagttgatg gctactacat ccctaaggac gcgaggctta gcgtgaacat ttgggcgatc    1200

ggtcgggacc cgaatgtttg ggagaatccg ttggagttct tgccggaaag attcttgtct    1260
```

gaagagaatg ggaagatcaa tcccggtggg aatgattttg agctgattcc gtttggagcc 1320
gggaggagaa tttgtgcggg gacaaggatg ggaatggtcc ttgtaagtta tattttgggc 1380
actttggtcc attcttttga ttggaaatta ccaaatggtg tcgctgagct taatatggat 1440
gaaagttttg ggcttgcatt gcaaaaggcc gtgccgctct cggccttggt cagcccacgg 1500
ttggcctcaa acgcgtacgc aacctgagct aatgggctgg gcctagtttt gtgggcctta 1560
atttagagac ttttgtgttt taaggtgtgt actttattaa ttgggtgctt aaatgtgtgt 1620
tttaatttgt atttatggtt aattatgact ttattgtata attatttatt tttcccttct 1680
gggtatttta tccatttaat ttttcttcag aattatgatc atagttatca gaataaaatt 1740
gaaaataatg aatcggaaaa aaaaaaaaaa aaaaaaaaaa a 1781

<210> SEQ ID NO 2
<211> LENGTH: 506
<212> TYPE: PRT
<213> ORGANISM: Viola x wittrockiana

<400> SEQUENCE: 2

Met Ala Ile Leu Val Thr Asp Phe Val Val Ala Ala Ile Ile Phe Leu
1 5 10 15

Ile Thr Arg Phe Leu Val Arg Ser Leu Phe Lys Lys Pro Thr Arg Pro
20 25 30

Leu Pro Pro Gly Pro Leu Gly Trp Pro Leu Val Gly Ala Leu Pro Leu
35 40 45

Leu Gly Ala Met Pro His Val Ala Leu Ala Lys Leu Ala Lys Lys Tyr
50 55 60

Gly Pro Ile Met His Leu Lys Met Gly Thr Cys Asp Met Val Val Ala
65 70 75 80

Ser Thr Pro Glu Ser Ala Arg Ala Phe Leu Lys Thr Leu Asp Leu Asn
85 90 95

Phe Ser Asn Arg Pro Pro Asn Ala Gly Ala Ser His Leu Ala Tyr Gly
100 105 110

Ala Gln Asp Leu Val Phe Ala Lys Tyr Gly Pro Arg Trp Lys Thr Leu
115 120 125

Arg Lys Leu Ser Asn Leu His Met Leu Gly Gly Lys Ala Leu Asp Asp
130 135 140

Trp Ala Asn Val Arg Val Thr Glu Leu Gly His Met Leu Lys Ala Met
145 150 155 160

Cys Glu Ala Ser Arg Cys Gly Glu Pro Val Val Leu Ala Glu Met Leu
165 170 175

Thr Tyr Ala Met Ala Asn Met Ile Gly Gln Val Ile Leu Ser Arg Arg
180 185 190

Val Phe Val Thr Lys Gly Thr Glu Ser Asn Glu Phe Lys Asp Met Val
195 200 205

Val Glu Leu Met Thr Ser Ala Gly Tyr Phe Asn Ile Gly Asp Phe Ile
210 215 220

Pro Ser Ile Ala Trp Met Asp Leu Gln Gly Ile Glu Arg Gly Met Lys
225 230 235 240

Lys Leu His Thr Lys Phe Asp Val Leu Leu Thr Lys Met Val Lys Glu
245 250 255

His Arg Ala Thr Ser His Glu Arg Lys Gly Lys Ala Asp Phe Leu Asp
260 265 270

Val Leu Leu Glu Glu Cys Asp Asn Thr Asn Gly Glu Lys Leu Ser Ile
275 280 285

```
Thr Asn Ile Lys Ala Val Leu Leu Asn Leu Phe Thr Ala Gly Thr Asp
    290                 295                 300

Thr Ser Ser Ser Ile Ile Glu Trp Ala Leu Thr Glu Met Ile Lys Asn
305                 310                 315                 320

Pro Thr Ile Leu Lys Lys Ala Gln Glu Glu Met Asp Arg Val Ile Gly
                325                 330                 335

Arg Asp Arg Arg Leu Leu Glu Ser Asp Ile Ser Ser Leu Pro Tyr Leu
            340                 345                 350

Gln Ala Ile Ala Lys Glu Thr Tyr Arg Lys His Pro Ser Thr Pro Leu
        355                 360                 365

Asn Leu Pro Arg Ile Ala Ile Gln Ala Cys Glu Val Asp Gly Tyr Tyr
    370                 375                 380

Ile Pro Lys Asp Ala Arg Leu Ser Val Asn Ile Trp Ala Ile Gly Arg
385                 390                 395                 400

Asp Pro Asn Val Trp Glu Asn Pro Leu Glu Phe Leu Pro Glu Arg Phe
                405                 410                 415

Leu Ser Glu Glu Asn Gly Lys Ile Asn Pro Gly Gly Asn Asp Phe Glu
            420                 425                 430

Leu Ile Pro Phe Gly Ala Gly Arg Arg Ile Cys Ala Gly Thr Arg Met
        435                 440                 445

Gly Met Val Leu Val Ser Tyr Ile Leu Gly Thr Leu Val His Ser Phe
    450                 455                 460

Asp Trp Lys Leu Pro Asn Gly Val Ala Glu Leu Asn Met Asp Glu Ser
465                 470                 475                 480

Phe Gly Leu Ala Leu Gln Lys Ala Val Pro Leu Ser Ala Leu Val Ser
                485                 490                 495

Pro Arg Leu Ala Ser Asn Ala Tyr Ala Thr
            500                 505
```

<210> SEQ ID NO 3
<211> LENGTH: 1920
<212> TYPE: DNA
<213> ORGANISM: Glycyrrhiza echinata

<400> SEQUENCE: 3

```
ccccaatttc ctctatcata agccattccg ttgattgagc ttcctttccg tgaaaaaaat     60

aactaagcga tatggaacct caactcgtag cagtgtctgt gttggtttca gcacttatct    120

gctacttctt tttccggcca tatttccacc gttacggaaa aaccttccca ccatctcctt    180

ttttccggct tccaataatt ggccacatgc acatgttagg tccccttctt caccaatcct    240

tccacaacct ctcccaccgt tacggtcctc tgttttcact taactttggc tctgttctct    300

gtgtcgttgc ttcaacccct cactttgcca aacaactcct tcaaaccaac gaactcgcct    360

ttaactgtcg cattgaatca accgccgtta aaaaactcac ttacgagtct tccttggcct    420

tcgcacctta cggtgattac tggaggttca ttaagaagct gagcatgaac gagcttttgg    480

gctctcgtag cataaacaac ttccaacacc tacgagcaca agagacccat caattgttaa    540

ggcttttgtc caacagggca agagcgtttg aggccgtgaa tatcaccgag gagcttctta    600

agttgaccaa caacgttatt tctataatga tggttgggga ggcagaggag gcaagggatg    660

tggtgcgtga tgtgacggag atatttggag agtttaatgt ttcggatttt atttggttgt    720

ttaagaagat ggacttgcag ggtttggga agaggattga ggatttgttt cagaggtttg    780

atacgttggt ggaaaggatt attagcaagc gggagcagac gaggaaagac agaaggagga    840
```

-continued

```
atgggaagaa gggtgagcag gggagtggtg atgggatcag agactttctt gatatcttgc    900

ttgactgtac tgaggatgag aattccgaga ttaaaatcca aagggttcac attaaggcct    960

tgattatgga tttcttcact gcagggacgg ataccacagc gatttcaaca gagtgggcat   1020

tagtggagct cgtcaagaaa ccctccgtgc tacaaaaagt tcgtgaagag atagacaatg   1080

tcgtaggaaa agacagactt gttgaggaat ctgattgtcc taatctccca tatctccaag   1140

ccattcttaa agaaacattc cgtttgcacc caccggttcc tatggttaca agaagatgcg   1200

tggcagagtg cacggtagag aattacgtca tcccagaaga ctcacttctc tttgtgaatg   1260

tttggtccat cggaagaaac ccaaagtttt gggacaaccc attggagttt cgccccgaac   1320

gattcttaaa actagaagga gattccagtg gagttgttga tgtgaggga agccattttc   1380

agcttctgcc atttgggtct ggaaggagga tgtgccctgg tgtgtccttg gctatgcaag   1440

aggtgccagc actacttggt gctataatcc agtgctttga tttccacgtt gtgggtccca   1500

aaggtgagat tttgaagggt gatgacatag tcattaatgt ggatgaaagg ccaggattga   1560

cggctccaag ggcacataac cttgtgtgtg ttcccgttga tagaacaagt ggcggtggac   1620

ccctcaaaat cattgaatgt tgattattcg tctcttgaat ttggatctgt gtgtggcttt   1680

gaataacatg tatggtgtat gtatgtatgt gttcttttct ttctttctaa ttctgatcag   1740

tagcgtacac taggcactag ccttcgttag tggcaataac ttcggcaaat taacgaacat   1800

atgctgttca gagatatttt ttgccatgta tcgtcattct attctaggtt gtttttccgt   1860

tttccttatt acattctatg ataaatataa taaattgagt aatattatag tctcttaatt   1920
```

```
<210> SEQ ID NO 4
<211> LENGTH: 523
<212> TYPE: PRT
<213> ORGANISM: Glycyrrhiza echinata

<400> SEQUENCE: 4

Met Glu Pro Gln Leu Val Ala Val Ser Val Leu Val Ser Ala Leu Ile
1               5                   10                  15

Cys Tyr Phe Phe Phe Arg Pro Tyr Phe His Arg Tyr Gly Lys Asn Leu
            20                  25                  30

Pro Pro Ser Pro Phe Phe Arg Leu Pro Ile Ile Gly His Met His Met
        35                  40                  45

Leu Gly Pro Leu Leu His Gln Ser Phe His Asn Leu Ser His Arg Tyr
    50                  55                  60

Gly Pro Leu Phe Ser Leu Asn Phe Gly Ser Val Leu Cys Val Val Ala
65                  70                  75                  80

Ser Thr Pro His Phe Ala Lys Gln Leu Leu Gln Thr Asn Glu Leu Ala
                85                  90                  95

Phe Asn Cys Arg Ile Glu Ser Thr Ala Val Lys Lys Leu Thr Tyr Glu
            100                 105                 110

Ser Ser Leu Ala Phe Ala Pro Tyr Gly Asp Tyr Trp Arg Phe Ile Lys
        115                 120                 125

Lys Leu Ser Met Asn Glu Leu Leu Gly Ser Arg Ser Ile Asn Asn Phe
    130                 135                 140

Gln His Leu Arg Ala Gln Glu Thr His Gln Leu Leu Arg Leu Leu Ser
145                 150                 155                 160

Asn Arg Ala Arg Ala Phe Glu Ala Val Asn Ile Thr Glu Glu Leu Leu
                165                 170                 175

Lys Leu Thr Asn Asn Val Ile Ser Ile Met Met Val Gly Glu Ala Glu
            180                 185                 190
```

```
Glu Ala Arg Asp Val Val Arg Asp Val Thr Glu Ile Phe Gly Glu Phe
        195                 200                 205

Asn Val Ser Asp Phe Ile Trp Leu Phe Lys Lys Met Asp Leu Gln Gly
    210                 215                 220

Phe Gly Lys Arg Ile Glu Asp Leu Phe Gln Arg Phe Asp Thr Leu Val
225                 230                 235                 240

Glu Arg Ile Ile Ser Lys Arg Glu Gln Thr Arg Lys Asp Arg Arg Arg
                245                 250                 255

Asn Gly Lys Lys Gly Glu Gln Gly Ser Gly Asp Gly Ile Arg Asp Phe
            260                 265                 270

Leu Asp Ile Leu Leu Asp Cys Thr Glu Asp Glu Asn Ser Glu Ile Lys
        275                 280                 285

Ile Gln Arg Val His Ile Lys Ala Leu Ile Met Asp Phe Phe Thr Ala
    290                 295                 300

Gly Thr Asp Thr Thr Ala Ile Ser Thr Glu Trp Ala Leu Val Glu Leu
305                 310                 315                 320

Val Lys Lys Pro Ser Val Leu Gln Lys Val Arg Glu Glu Ile Asp Asn
                325                 330                 335

Val Val Gly Lys Asp Arg Leu Val Glu Glu Ser Asp Cys Pro Asn Leu
            340                 345                 350

Pro Tyr Leu Gln Ala Ile Leu Lys Glu Thr Phe Arg Leu His Pro Pro
        355                 360                 365

Val Pro Met Val Thr Arg Arg Cys Val Ala Glu Cys Thr Val Glu Asn
    370                 375                 380

Tyr Val Ile Pro Glu Asp Ser Leu Leu Phe Val Asn Val Trp Ser Ile
385                 390                 395                 400

Gly Arg Asn Pro Lys Phe Trp Asp Asn Pro Leu Glu Phe Arg Pro Glu
                405                 410                 415

Arg Phe Leu Lys Leu Glu Gly Asp Ser Ser Gly Val Val Asp Val Arg
            420                 425                 430

Gly Ser His Phe Gln Leu Leu Pro Phe Gly Ser Gly Arg Arg Met Cys
        435                 440                 445

Pro Gly Val Ser Leu Ala Met Gln Glu Val Pro Ala Leu Leu Gly Ala
    450                 455                 460

Ile Ile Gln Cys Phe Asp Phe His Val Val Gly Pro Lys Gly Glu Ile
465                 470                 475                 480

Leu Lys Gly Asp Asp Ile Val Ile Asn Val Asp Glu Arg Pro Gly Leu
                485                 490                 495

Thr Ala Pro Arg Ala His Asn Leu Val Cys Val Pro Val Asp Arg Thr
            500                 505                 510

Ser Gly Gly Gly Pro Leu Lys Ile Ile Glu Cys
        515                 520
```

<210> SEQ ID NO 5
<211> LENGTH: 1624
<212> TYPE: DNA
<213> ORGANISM: Oryza sativa Japonica Group

<400> SEQUENCE: 5

```
tgcagctacc tacacgaccc aagcagcagc agcacgcaca cggcacacct actcccgctt      60

cacatcgcca ggtgttcgac cgaggccacc accggcaatg ccgagctctg gcgacgcggc     120

gggcaggcgg ccgcatgtgg tgctcatccc gagcgccggc atgggccacc tcgtcccctt     180

cggccgcctc gccgtggcgc tctcctccgg ccacggctgc gacgtctccc tcgtcacggt     240
```

```
gctccccacg gtgtccaccg cggagtcgaa gcacctcgac gcgctgttcg acgcgttccc    300
ggcggtgcgg cggctcgact tcgagctcgc gccgttcgac gcgtcggagt tccccagcgc    360
cgacccgttc ttcctccggt tcgaggccat gcggcggtcg gcgccgctgc tcggcccgct    420
cctcaccggc gccggcgcat cggcgctcgc cacggacatc gcgctgacat ccgtcgtcat    480
acccgtggcg aaggagcagg gcctcccgtg ccacatcctc ttcaccgcct ccgccgcgat    540
gctctccctc tgcgcctact tccccacata cctcgacgcc aacgctggcg acggcggcgg    600
cgtcggcgac gtcgacatcc ccggcgtgta ccgcatcccc aaggcctcca tcccgcaggc    660
gctgcacgat cccaaccacc tcttcacccg ccagttcgtc gccaacggcc ggagcctcac    720
gagcgccgcc ggcatcctcg tcaacacgtt cgacgccttg gagccggagg ccgtcgcggc    780
cctgcagcag ggcaaggtcg cctccggctt cccgccggtg ttcgccgtgg ggccacttct    840
cccggcgagc aaccaggcaa aagatccgca ggcaaactac atggagtggc tcgacgcgca    900
gccggcgcgg tcggtggtgt acgtgagctt cggcagccgc aaggccatct caggggagca    960
gctcagggag ctcgccgccg ggctggagac cagcggccac aggttcctgt gggtggtgaa   1020
gagcaccgtc gtggacaggg acgacgccgc cgagctcggc gagctgctcg gcgaggggtt   1080
cttgaagcgg gtggagaagc gaggcctcgt caccaaggca tgggtggatc aggaagaggt   1140
cctgaagcac gagtccgtgg cgctgttcgt gagccactgc ggctggaact cggtgacgga   1200
ggcggcggcg agcggcgtcc cggtgctggc gctgccgagg ttcggcgacc agcgggtgaa   1260
ctccggcgtg gtggcgcgcg ccgggctcgg cgtgtgggcg gacacctgga gctgggaggg   1320
ggaagccggg gtgatcggcg cagaggagat atcggagaag gtgaaggcgg cgatggcgga   1380
cgaggcgttg cgtaggaagg cggcgagcct cgccaaggcc gccgcgaagg ccgtcgccgg   1440
cggtggatcg agccaccgtt gtctggtcga gttcgcgcgg ctgtgccaag gggaacatg    1500
tcgcactaat tgagtactga gacatgggtt ctaatttaaa taattcggat ggaatccttg   1560
ttacagattt taaattggaa taagaaatga agccatatga aatttggaag aattttaaat   1620
ttaa                                                                1624
```

<210> SEQ ID NO 6
<211> LENGTH: 471
<212> TYPE: PRT
<213> ORGANISM: Oryza sativa Japonica Group

<400> SEQUENCE: 6

```
Met Pro Ser Ser Gly Asp Ala Ala Gly Arg Arg Pro His Val Val Leu
1               5                   10                  15

Ile Pro Ser Ala Gly Met Gly His Leu Val Pro Phe Gly Arg Leu Ala
            20                  25                  30

Val Ala Leu Ser Ser Gly His Gly Cys Asp Val Ser Leu Val Thr Val
        35                  40                  45

Leu Pro Thr Val Ser Thr Ala Glu Ser Lys His Leu Asp Ala Leu Phe
    50                  55                  60

Asp Ala Phe Pro Ala Val Arg Arg Leu Asp Phe Glu Leu Ala Pro Phe
65                  70                  75                  80

Asp Ala Ser Glu Phe Pro Ser Ala Asp Pro Phe Phe Leu Arg Phe Glu
                85                  90                  95

Ala Met Arg Arg Ser Ala Pro Leu Leu Gly Pro Leu Leu Thr Gly Ala
            100                 105                 110

Gly Ala Ser Ala Leu Ala Thr Asp Ile Ala Leu Thr Ser Val Val Ile
```

-continued

```
        115                 120                 125

Pro Val Ala Lys Glu Gln Gly Leu Pro Cys His Ile Leu Phe Thr Ala
    130                 135                 140

Ser Ala Ala Met Leu Ser Leu Cys Ala Tyr Phe Pro Thr Tyr Leu Asp
145                 150                 155                 160

Ala Asn Ala Gly Asp Gly Gly Gly Val Gly Asp Val Asp Ile Pro Gly
                165                 170                 175

Val Tyr Arg Ile Pro Lys Ala Ser Ile Pro Gln Ala Leu His Asp Pro
            180                 185                 190

Asn His Leu Phe Thr Arg Gln Phe Val Ala Asn Gly Arg Ser Leu Thr
        195                 200                 205

Ser Ala Ala Gly Ile Leu Val Asn Thr Phe Asp Ala Leu Glu Pro Glu
    210                 215                 220

Ala Val Ala Ala Leu Gln Gln Gly Lys Val Ala Ser Gly Phe Pro Pro
225                 230                 235                 240

Val Phe Ala Val Gly Pro Leu Leu Pro Ala Ser Asn Gln Ala Lys Asp
                245                 250                 255

Pro Gln Ala Asn Tyr Met Glu Trp Leu Asp Ala Gln Pro Ala Arg Ser
            260                 265                 270

Val Val Tyr Val Ser Phe Gly Ser Arg Lys Ala Ile Ser Gly Glu Gln
        275                 280                 285

Leu Arg Glu Leu Ala Ala Gly Leu Glu Thr Ser Gly His Arg Phe Leu
    290                 295                 300

Trp Val Val Lys Ser Thr Val Val Asp Arg Asp Asp Ala Ala Glu Leu
305                 310                 315                 320

Gly Glu Leu Leu Gly Glu Gly Phe Leu Lys Arg Val Glu Lys Arg Gly
                325                 330                 335

Leu Val Thr Lys Ala Trp Val Asp Gln Glu Glu Val Leu Lys His Glu
            340                 345                 350

Ser Val Ala Leu Phe Val Ser His Cys Gly Trp Asn Ser Val Thr Glu
        355                 360                 365

Ala Ala Ala Ser Gly Val Pro Val Leu Ala Leu Pro Arg Phe Gly Asp
    370                 375                 380

Gln Arg Val Asn Ser Gly Val Val Ala Arg Ala Gly Leu Gly Val Trp
385                 390                 395                 400

Ala Asp Thr Trp Ser Trp Glu Gly Glu Ala Gly Val Ile Gly Ala Glu
                405                 410                 415

Glu Ile Ser Glu Lys Val Lys Ala Ala Met Ala Asp Glu Ala Leu Arg
            420                 425                 430

Arg Lys Ala Ala Ser Leu Ala Lys Ala Ala Ala Lys Ala Val Ala Gly
        435                 440                 445

Gly Gly Ser Ser His Arg Cys Leu Val Glu Phe Ala Arg Leu Cys Gln
    450                 455                 460

Gly Gly Thr Cys Arg Thr Asn
465                 470
```

<210> SEQ ID NO 7
<211> LENGTH: 1178
<212> TYPE: DNA
<213> ORGANISM: Glycyrrhiza echinata

<400> SEQUENCE: 7

```
ctattccatt cttttccgtt caatggcttc ttcaacctca acaaccactt ccaaagagat      60

agacagggag cttcctcctc ttctccgggt ctacaaagat ggaaccgtgg agcgattcct     120
```

```
aggctcatcg tttgtaccac cttcccctga agaccccgaa acaggggttt ccacgaaaga    180

catagtaatc tcagaaaacc ccaccatctc tgctcgcgtt taccttccaa aactgaacaa    240

caccaccgag aagctcccaa tcttggtcta ctaccacggc ggcgcgttct gcctcgaatc    300

tgctttctcc ttcctccacc aacgctacct caacatcgtt gcttccaagg caaatgttct    360

agtagtttcc atcgagtaca ggctcgcccc agaacaccct cttccggctg catatgaaga    420

tggttggtat gctctcaaat gggtcacttc tcattccaca aacaacaaca aacccaccaa    480

cgctgaccca tggttgatca aacacggtga tttcaacagg ttctacatcg gggtgacac    540

ttctggtgca aacattgcac acaatgcggc tcttcgtgtt ggtgctgagg ccttacctgg    600

ggggctgaga atagcagggg tactctctgc ttttcctctg ttttggggtt ctaagcctgt    660

tttgtcagaa cctgtcgagg ggcatgagaa gagctcaccc atgcaagttt ggaactttgt    720

gtacccagat gcaccaggtg gcatagataa cccactaatc aacccctttgg cacctggggc    780

tcctaacttg gccacacttg ggtgtccaaa gatgttggtc tttgttgcgg ggaaggatga    840

tcttagagac agagggattt ggtactatga ggctgtgaag gaaagtgggt ggaaagggga    900

tgtggaactt gctcagtatg aaggggagga acattgcttc cagatctacc atcctgaaac    960

tgagaattct aaagatctca tcggtcgcat cgcttccttc cttgtttgaa cacacagcta    1020

gacttcgggt tcattattac tagtatgtga ttttgtttga ttaatgtttt gtcatcaatt    1080

gatgggtaat aaattggatt agggtactag ggttcctgaa tcatgctcaa ttttactttt    1140

cctgtactat tacttgttta tgaaagaatt aatggcat                            1178
```

<210> SEQ ID NO 8
<211> LENGTH: 328
<212> TYPE: PRT
<213> ORGANISM: Glycyrrhiza echinata

<400> SEQUENCE: 8

```
Met Ala Ser Ser Thr Ser Thr Thr Thr Ser Lys Glu Ile Asp Arg Glu
1               5                   10                  15

Leu Pro Pro Leu Leu Arg Val Tyr Lys Asp Gly Thr Val Glu Arg Phe
            20                  25                  30

Leu Gly Ser Ser Phe Val Pro Pro Ser Pro Glu Asp Pro Glu Thr Gly
        35                  40                  45

Val Ser Thr Lys Asp Ile Val Ile Ser Glu Asn Pro Thr Ile Ser Ala
    50                  55                  60

Arg Val Tyr Leu Pro Lys Leu Asn Asn Thr Thr Glu Lys Leu Pro Ile
65                  70                  75                  80

Leu Val Tyr Tyr His Gly Gly Ala Phe Cys Leu Glu Ser Ala Phe Ser
                85                  90                  95

Phe Leu His Gln Arg Tyr Leu Asn Ile Val Ala Ser Lys Ala Asn Val
            100                 105                 110

Leu Val Val Ser Ile Glu Tyr Arg Leu Ala Pro Glu His Pro Leu Pro
        115                 120                 125

Ala Ala Tyr Glu Asp Gly Trp Tyr Ala Leu Lys Trp Val Thr Ser His
    130                 135                 140

Ser Thr Asn Asn Asn Lys Pro Thr Asn Ala Asp Pro Trp Leu Ile Lys
145                 150                 155                 160

His Gly Asp Phe Asn Arg Phe Tyr Ile Gly Gly Asp Thr Ser Gly Ala
                165                 170                 175

Asn Ile Ala His Asn Ala Ala Leu Arg Val Gly Ala Glu Ala Leu Pro
```

-continued

```
        180                 185                 190

Gly Gly Leu Arg Ile Ala Gly Val Leu Ser Ala Phe Pro Leu Phe Trp
    195                 200                 205

Gly Ser Lys Pro Val Leu Ser Glu Pro Val Glu Gly His Glu Lys Ser
    210                 215                 220

Ser Pro Met Gln Val Trp Asn Phe Val Tyr Pro Asp Ala Pro Gly Gly
225                 230                 235                 240

Ile Asp Asn Pro Leu Ile Asn Pro Leu Ala Pro Gly Ala Pro Asn Leu
                245                 250                 255

Ala Thr Leu Gly Cys Pro Lys Met Leu Val Phe Val Ala Gly Lys Asp
            260                 265                 270

Asp Leu Arg Asp Arg Gly Ile Trp Tyr Tyr Glu Ala Val Lys Glu Ser
        275                 280                 285

Gly Trp Lys Gly Asp Val Glu Leu Ala Gln Tyr Glu Gly Glu Glu His
    290                 295                 300

Cys Phe Gln Ile Tyr His Pro Glu Thr Glu Asn Ser Lys Asp Leu Ile
305                 310                 315                 320

Gly Arg Ile Ala Ser Phe Leu Val
                325


<210> SEQ ID NO 9
<211> LENGTH: 1927
<212> TYPE: DNA
<213> ORGANISM: Campanula medium

<400> SEQUENCE: 9

accaaatgag ctttgtaatt tgagattaat cataattgca tgctcaacta acattctgta      60

ttcatatatc catatgtatt ttgacctata gatattacat tacaccttga ggcctttata     120

tatagagagt gtatctactt cccttaatat cacctttca ttcaacaagt gaagccacca      180

tgtctataga catatccacc ctcttctatg aacttgttgc agcaatttca ctctacttag     240

ctacctactc tttcattcgt ttcctcttca aaccctctca ccaccaccac ctccctcccg     300

gcccaaccgg atggccgatc atcggagccc ttccactctt aggcaccatg ccacatgttt     360

ccttagccga catggccgtt aaatacggtc ctataatgta cctaaaactt ggttcaaagg     420

gcaccgtcgt ggcctcaaat ccaaaagccg cccgagcctt cttgaaaacc catgatgcca     480

atttttctaa ccgtccgatt gatgggggcc ctacctacct cgcgtataat gcacaagaca     540

tggtttttgc agaatatggc ccaaaatgga agcttttgcg aaagctatgt agcttgcaca     600

tgttaggccc gaaggcactc gaggattggg ctcatgtcaa agtttcagag gtcggtcata     660

tgctcaaaga aatgtacgag caatcgagta agtcagtgcc agtgccagtg gtggtgccag     720

agatgttaac ttatgccatg gctaatatga ttggacgaat catactcagc cgacgccctt     780

ttgttatcac gagcaaatta gactcgtctg cttctgcttc tgcttctgtt agtgaattcc     840

aatatatggt tatggagctc atgaggatgg cagggttgtt caatattggt gatttcatac     900

catatattgc atggatggat ttgcaaggca ttcaacgtga tatgaaggtt atacagaaaa     960

agtttgatgt cttgttgaac aaaatgatca aggaacatac agaatccgct catgatcgca    1020

aagataatcc tgattttctt gatattctta tggcggctac ccaagaaaac acggagggaa    1080

ttcagcttaa tcttgtaaat gttaaggcac ttcttttgga tttattcacg gcgggcacgg    1140

atacatcatc aagtgtgatc gaatgggcac tagccgaaat gttgaaccat cgacagatcc    1200

taaaccgggc ccacgaagaa atggaccaag tcattggcag aaacagaaga ctagaacaat    1260
```

ctgacatacc aaacttgcca tatttccaag ccatatgcaa agaaacattc cgaaaacacc 1320
cttccacgcc cttaaacctc ccaagaatct caacagaagc atgtgaagtg gacggatttc 1380
acataccaaa aaacactaga ctaatagtga acatatgggc aatagggagg gaccctaaag 1440
tgtgggaaaa tccattagat tttactccgg aacgtttctt gagtgaaaaa cacgcgaaaa 1500
ttgatccgcg aggtaatcat tttgagttaa tcccatttgg ggctggacga aggatatgtg 1560
caggggctag aatgggagcg gcctcggtcg agtacatatt aggtacattg gtgcactcat 1620
ttgattggaa attgcctgat ggagttgtgg aagttaatat ggaagagagc tttgggatcg 1680
cattgcaaaa aaaagtgcct ctttctgcta ttgttactcc aagattgcct ccaagttctt 1740
acactgtcta ggcaaatgct tatatatatg aataattgat tgagttgttt agttgtatga 1800
aagatttgag aaaataaatt attaggtttt gcaccattat gttgagatgg ttgttgttag 1860
tgttaaggaa gtcgattgta gtaataataa ttttattttt ttcgaaaaaa aaaaaaaaaa 1920
aaaaaaa 1927

<210> SEQ ID NO 10
<211> LENGTH: 523
<212> TYPE: PRT
<213> ORGANISM: Campanula medium

<400> SEQUENCE: 10

Met Ser Ile Asp Ile Ser Thr Leu Phe Tyr Glu Leu Val Ala Ala Ile
1 5 10 15

Ser Leu Tyr Leu Ala Thr Tyr Ser Phe Ile Arg Phe Leu Phe Lys Pro
20 25 30

Ser His His His His Leu Pro Pro Gly Pro Thr Gly Trp Pro Ile Ile
35 40 45

Gly Ala Leu Pro Leu Leu Gly Thr Met Pro His Val Ser Leu Ala Asp
50 55 60

Met Ala Val Lys Tyr Gly Pro Ile Met Tyr Leu Lys Leu Gly Ser Lys
65 70 75 80

Gly Thr Val Val Ala Ser Asn Pro Lys Ala Ala Arg Ala Phe Leu Lys
85 90 95

Thr His Asp Ala Asn Phe Ser Asn Arg Pro Ile Asp Gly Gly Pro Thr
100 105 110

Tyr Leu Ala Tyr Asn Ala Gln Asp Met Val Phe Ala Glu Tyr Gly Pro
115 120 125

Lys Trp Lys Leu Leu Arg Lys Leu Cys Ser Leu His Met Leu Gly Pro
130 135 140

Lys Ala Leu Glu Asp Trp Ala His Val Lys Val Ser Glu Val Gly His
145 150 155 160

Met Leu Lys Glu Met Tyr Glu Gln Ser Ser Lys Ser Val Pro Val Pro
165 170 175

Val Val Val Pro Glu Met Leu Thr Tyr Ala Met Ala Asn Met Ile Gly
180 185 190

Arg Ile Ile Leu Ser Arg Arg Pro Phe Val Ile Thr Ser Lys Leu Asp
195 200 205

Ser Ser Ala Ser Ala Ser Ala Ser Val Ser Glu Phe Gln Tyr Met Val
210 215 220

Met Glu Leu Met Arg Met Ala Gly Leu Phe Asn Ile Gly Asp Phe Ile
225 230 235 240

Pro Tyr Ile Ala Trp Met Asp Leu Gln Gly Ile Gln Arg Asp Met Lys
245 250 255

```
Val Ile Gln Lys Lys Phe Asp Val Leu Leu Asn Lys Met Ile Lys Glu
            260                 265                 270

His Thr Glu Ser Ala His Asp Arg Lys Asp Asn Pro Asp Phe Leu Asp
        275                 280                 285

Ile Leu Met Ala Ala Thr Gln Glu Asn Thr Glu Gly Ile Gln Leu Asn
    290                 295                 300

Leu Val Asn Val Lys Ala Leu Leu Leu Asp Leu Phe Thr Ala Gly Thr
305                 310                 315                 320

Asp Thr Ser Ser Ser Val Ile Glu Trp Ala Leu Ala Glu Met Leu Asn
                325                 330                 335

His Arg Gln Ile Leu Asn Arg Ala His Glu Glu Met Asp Gln Val Ile
            340                 345                 350

Gly Arg Asn Arg Arg Leu Glu Gln Ser Asp Ile Pro Asn Leu Pro Tyr
        355                 360                 365

Phe Gln Ala Ile Cys Lys Glu Thr Phe Arg Lys His Pro Ser Thr Pro
    370                 375                 380

Leu Asn Leu Pro Arg Ile Ser Thr Glu Ala Cys Glu Val Asp Gly Phe
385                 390                 395                 400

His Ile Pro Lys Asn Thr Arg Leu Ile Val Asn Ile Trp Ala Ile Gly
                405                 410                 415

Arg Asp Pro Lys Val Trp Glu Asn Pro Leu Asp Phe Thr Pro Glu Arg
            420                 425                 430

Phe Leu Ser Glu Lys His Ala Lys Ile Asp Pro Arg Gly Asn His Phe
        435                 440                 445

Glu Leu Ile Pro Phe Gly Ala Gly Arg Arg Ile Cys Ala Gly Ala Arg
    450                 455                 460

Met Gly Ala Ala Ser Val Glu Tyr Ile Leu Gly Thr Leu Val His Ser
465                 470                 475                 480

Phe Asp Trp Lys Leu Pro Asp Gly Val Val Glu Val Asn Met Glu Glu
                485                 490                 495

Ser Phe Gly Ile Ala Leu Gln Lys Lys Val Pro Leu Ser Ala Ile Val
            500                 505                 510

Thr Pro Arg Leu Pro Pro Ser Ser Tyr Thr Val
        515                 520
```

<210> SEQ ID NO 11
<211> LENGTH: 1404
<212> TYPE: DNA
<213> ORGANISM: Oryza sativa Japonica Group

<400> SEQUENCE: 11

```
cgtattgctg catatatacg gtccctcgcg gcctcatgtc gtggtatttg tctgcaccac     60

acaaccgcgc tctaattgct tcgatttggg agtaagcttt accaggagca gtgcgatgga    120

ttccagcagc gccgagatcc tcatcgacct cggtggcttc cggctataca aagatggcca    180

cgccgaccgt gccggcggca tggagagtgt gcctgccggc tacgacgacg agaccggcgt    240

cacgtccaag gacgtcgtca tcgacgctgt caccggcgtg tccgcgcgcc tctacctacc    300

accgtgcatc cagccagcta ccgacgacga cggtaagaag ctcccgatcc tcctcttctt    360

ccatgctggc tacttcgtcg tcgggtcagc gagctggcct cctgtccacc gctacaccaa    420

ctctgtcgtc gcaagcgccc gcgtcgtcgc cgtcgccgtc aactaccgcc tcgcgcccga    480

gcacctgctc ccgacagcct acgacgactc atgggcggcg ctcagctggg cggtgtccgg    540

cgccgaccct tggttgtccg cgcacggtga caccggccga gtcttcttgt ccggcgccag    600
```

```
cgccggcggg aacatagccc acaacatgac catcgccgtg ggcgtgcgcg gcctggacgc    660

cgtcgtaccg gcgccacgca tagagggcac gatcttgctc caccccttcct tctgcggcga    720

gacgaggatg gaggttgagc cggaggagtt ctggggcggc gtcaagaaga gatgggcggt    780

catcttcccc ggcgcgaacg gcgggctgga cgatccgcgg atgaacccga tggccgccgg    840

cgcgccgagc ctgacaaagc tggcgtgcga gaggatgctg gtctgctcgg cggggttcga    900

tccgaggagg acaagggatc gggcgtacta cgacgcagtc aaggccagcg ggtggggacg    960

cgaggtggac tggttcgagt cggagggtga gggccaccac ttcttcgtcg acaagcccgg   1020

cagccacgag gccagcaagc tcatggaacg agtggctgct ttcattgctg gccattaaac   1080

tgtgcttcca gctggataat ttgcctcgtg tttctaagag caaggataac agtagagctc   1140

actatctact attagcacat cttaaagcca acacatataa tagattagct ataaggttgg   1200

ctataatttt tcttttccta tctctatatc tcacttatac atttattatt tttgtcttgg   1260

agcttgtgat aagctagctc ttgtatgaga gccaatacct ttgatttttt gttacctctc   1320

tactccatat aagcttatag taagcttata gctcactatt atacttgctc taagatgtca   1380

aaatggtgaa tagtttatcc cgaa                                          1404


<210> SEQ ID NO 12
<211> LENGTH: 320
<212> TYPE: PRT
<213> ORGANISM: Oryza sativa Japonica Group

<400> SEQUENCE: 12

Met Asp Ser Ser Ser Ala Glu Ile Leu Ile Asp Leu Gly Gly Phe Arg
1               5                   10                  15

Leu Tyr Lys Asp Gly His Ala Asp Arg Ala Gly Gly Met Glu Ser Val
            20                  25                  30

Pro Ala Gly Tyr Asp Asp Glu Thr Gly Val Thr Ser Lys Asp Val Val
        35                  40                  45

Ile Asp Ala Val Thr Gly Val Ser Ala Arg Leu Tyr Leu Pro Pro Cys
    50                  55                  60

Ile Gln Pro Ala Thr Asp Asp Asp Gly Lys Lys Leu Pro Ile Leu Leu
65                  70                  75                  80

Phe Phe His Ala Gly Tyr Phe Val Val Gly Ser Ala Ser Trp Pro Pro
                85                  90                  95

Val His Arg Tyr Thr Asn Ser Val Val Ala Ser Ala Arg Val Val Ala
            100                 105                 110

Val Ala Val Asn Tyr Arg Leu Ala Pro Glu His Leu Leu Pro Thr Ala
        115                 120                 125

Tyr Asp Asp Ser Trp Ala Ala Leu Ser Trp Ala Val Ser Gly Ala Asp
    130                 135                 140

Pro Trp Leu Ser Ala His Gly Asp Thr Gly Arg Val Phe Leu Ser Gly
145                 150                 155                 160

Ala Ser Ala Gly Gly Asn Ile Ala His Asn Met Thr Ile Ala Val Gly
                165                 170                 175

Val Arg Gly Leu Asp Ala Val Val Pro Ala Pro Arg Ile Glu Gly Thr
            180                 185                 190

Ile Leu Leu His Pro Ser Phe Cys Gly Glu Thr Arg Met Glu Val Glu
        195                 200                 205

Pro Glu Glu Phe Trp Gly Gly Val Lys Lys Arg Trp Ala Val Ile Phe
    210                 215                 220
```

-continued

```
Pro Gly Ala Asn Gly Gly Leu Asp Asp Pro Arg Met Asn Pro Met Ala
225                 230                 235                 240

Ala Gly Ala Pro Ser Leu Thr Lys Leu Ala Cys Glu Arg Met Leu Val
                245                 250                 255

Cys Ser Ala Gly Phe Asp Pro Arg Arg Thr Arg Asp Arg Ala Tyr Tyr
            260                 265                 270

Asp Ala Val Lys Ala Ser Gly Trp Gly Arg Glu Val Asp Trp Phe Glu
        275                 280                 285

Ser Glu Gly Glu Gly His His Phe Phe Val Asp Lys Pro Gly Ser His
    290                 295                 300

Glu Ala Ser Lys Leu Met Glu Arg Val Ala Ala Phe Ile Ala Gly His
305                 310                 315                 320
```

<210> SEQ ID NO 13
<211> LENGTH: 1416
<212> TYPE: DNA
<213> ORGANISM: Oryza sativa Japonica Group

<400> SEQUENCE: 13

```
atgccgagct ctggcgacgc ggcgggcagg cggccgcatg tggtgctcat cccgagcgcc     60

ggcatgggcc acctcgtccc cttcggccgc ctcgccgtgg cgctctcctc cggccacggc    120

tgcgacgtct ccctcgtcac ggtgctcccc acggtgtcca ccgcggagtc gaagcacctc    180

gacgcgctgt tcgacgcgtt cccggcggtg cggcggctcg acttcgagct cgcgccgttc    240

gacgcgtcgg agttccccag cgccgacccg ttcttcctcc ggttcgaggc catgcggcgg    300

tcggcgccgc tgctcggccc gctcctcacc ggcgccggcg catcggcgct cgccacggac    360

atcgcgctga catccgtcgt catacccgtg gcgaaggagc agggcctccc gtgccacatc    420

ctcttcaccg cctccgccgc gatgctctcc ctctgcgcct acttccccac atacctcgac    480

gccaacgctg gcgacggcgg cggcgtcggc gacgtcgaca tccccggcgt gtaccgcatc    540

cccaaggcct ccatcccgca ggcgctgcac gatcccaacc acctcttcac ccgccagttc    600

gtcgccaacg gccggagcct cacgagcgcc gccggcatcc tcgtcaacac gttcgacgcc    660

ttggagccgg aggccgtcgc ggccctgcag cagggcaagg tcgcctccgg cttcccgccg    720

gtgttcgccg tggggccact tctcccggcg agcaaccagg caaaagatcc gcaggcaaac    780

tacatggagt ggctcgacgc gcagccggcg cggtcggtgg tgtacgtgag cttcggcagc    840

cgcaaggcca tctcagggga gcagctcagg gagctcgccg ccgggctgga gaccagcggc    900

cacaggttcc tgtgggtggt gaagagcacc gtcgtggaca gggacgacgc cgccgagctc    960

ggcgagctgc tcggcgaggg gttcttgaag cgggtggaga agcgaggcct cgtcaccaag   1020

gcatgggtgg atcaggaaga ggtcctgaag cacgagtccg tggcgctgtt cgtgagccac   1080

tgcggctgga actcggtgac ggaggcggcg gcgagcggcg tcccggtgct ggcgctgccg   1140

aggttcggcg accagcgggt gaactccggc gtggtggcgc gcgccgggct cggcgtgtgg   1200

gcggacacct ggagctggga gggggaagcc ggggtgatcg gcgcagagga gatatcggag   1260

aaggtgaagg cggcgatggc ggacgaggcg ttgcgtagga aggcggcgag cctcgccaag   1320

gccgccgcga aggccgtcgc cggcggtgga tcgagccacc gttgtctggt cgagttcgcg   1380

cggctgtgcc aagggggaac atgtcgcact aattga                             1416
```

<210> SEQ ID NO 14
<211> LENGTH: 471
<212> TYPE: PRT
<213> ORGANISM: Oryza sativa Japonica Group

<400> SEQUENCE: 14

Met Pro Ser Ser Gly Asp Ala Ala Gly Arg Arg Pro His Val Val Leu
1 5 10 15

Ile Pro Ser Ala Gly Met Gly His Leu Val Pro Phe Gly Arg Leu Ala
20 25 30

Val Ala Leu Ser Ser Gly His Gly Cys Asp Val Ser Leu Val Thr Val
35 40 45

Leu Pro Thr Val Ser Thr Ala Glu Ser Lys His Leu Asp Ala Leu Phe
50 55 60

Asp Ala Phe Pro Ala Val Arg Arg Leu Asp Phe Glu Leu Ala Pro Phe
65 70 75 80

Asp Ala Ser Glu Phe Pro Ser Ala Asp Pro Phe Phe Leu Arg Phe Glu
85 90 95

Ala Met Arg Arg Ser Ala Pro Leu Leu Gly Pro Leu Leu Thr Gly Ala
100 105 110

Gly Ala Ser Ala Leu Ala Thr Asp Ile Ala Leu Thr Ser Val Val Ile
115 120 125

Pro Val Ala Lys Glu Gln Gly Leu Pro Cys His Ile Leu Phe Thr Ala
130 135 140

Ser Ala Ala Met Leu Ser Leu Cys Ala Tyr Phe Pro Thr Tyr Leu Asp
145 150 155 160

Ala Asn Ala Gly Asp Gly Gly Gly Val Gly Asp Val Asp Ile Pro Gly
165 170 175

Val Tyr Arg Ile Pro Lys Ala Ser Ile Pro Gln Ala Leu His Asp Pro
180 185 190

Asn His Leu Phe Thr Arg Gln Phe Val Ala Asn Gly Arg Ser Leu Thr
195 200 205

Ser Ala Ala Gly Ile Leu Val Asn Thr Phe Asp Ala Leu Glu Pro Glu
210 215 220

Ala Val Ala Ala Leu Gln Gln Gly Lys Val Ala Ser Gly Phe Pro Pro
225 230 235 240

Val Phe Ala Val Gly Pro Leu Leu Pro Ala Ser Asn Gln Ala Lys Asp
245 250 255

Pro Gln Ala Asn Tyr Met Glu Trp Leu Asp Ala Gln Pro Ala Arg Ser
260 265 270

Val Val Tyr Val Ser Phe Gly Ser Arg Lys Ala Ile Ser Gly Glu Gln
275 280 285

Leu Arg Glu Leu Ala Ala Gly Leu Glu Thr Ser Gly His Arg Phe Leu
290 295 300

Trp Val Val Lys Ser Thr Val Val Asp Arg Asp Asp Ala Ala Glu Leu
305 310 315 320

Gly Glu Leu Leu Gly Glu Gly Phe Leu Lys Arg Val Glu Lys Arg Gly
325 330 335

Leu Val Thr Lys Ala Trp Val Asp Gln Glu Glu Val Leu Lys His Glu
340 345 350

Ser Val Ala Leu Phe Val Ser His Cys Gly Trp Asn Ser Val Thr Glu
355 360 365

Ala Ala Ala Ser Gly Val Pro Val Leu Ala Leu Pro Arg Phe Gly Asp
370 375 380

Gln Arg Val Asn Ser Gly Val Val Ala Arg Ala Gly Leu Gly Val Trp
385 390 395 400

Ala Asp Thr Trp Ser Trp Glu Gly Glu Ala Gly Val Ile Gly Ala Glu

```
                405                 410                 415

Glu Ile Ser Glu Lys Val Lys Ala Ala Met Ala Asp Glu Ala Leu Arg
            420                 425                 430

Arg Lys Ala Ala Ser Leu Ala Lys Ala Ala Ala Lys Ala Val Ala Gly
        435                 440                 445

Gly Gly Ser Ser His Arg Cys Leu Val Glu Phe Ala Arg Leu Cys Gln
    450                 455                 460

Gly Gly Thr Cys Arg Thr Asn
465                 470


<210> SEQ ID NO 15
<211> LENGTH: 990
<212> TYPE: DNA
<213> ORGANISM: Lotus japonicus

<400> SEQUENCE: 15

atggcttctg caacaaccac cccaaccaaa gagatagaca gagacctccc tcctcttctc      60

cgagtctaca aagatggaac cgtggaacgt ctcctaggct ctcctgtcgt tccagcaatc     120

cctcatgacc cagaaacaga ggtctcatca aaagacatag tcatctcaca aaccccctta     180

atctctgctc gtatccacct cccaaaacag agcaaccccc aaaacccaaa ggttccaata     240

ttgatctact accatggtgg tgcgttttgc cttgaatcag ctttctcctt cctccaccaa     300

cgctacctca acatcgtggc ttcacgatca aacgttgtgg tggtttccgt cgagtacagg     360

ctcgcgccag agcatcctct gcctgcagca tatgaagatg gttgggaagc tctgaaatgg     420

gttacctctc attccaccga caacaaaccc atcaactctg agccatggtt gatcgaacat     480

ggtgatttca gcagattcta catcggaggt gacacttcag gtgccaacat cgcataccat     540

gtgggtctcc gtgtcggtgg tggagttgag aaattgccag gggatgtgaa aattgcaggg     600

gcgttacttg cttttcccct gttttggagt tcataccctg ttttggaaga acctgttgag     660

gggtttgaac agagtttgag caggaaggtt tggaactttg tgtacccaga tgcacctggt     720

gggatcgaca accctctgat caatcctttg gctgatgggg ctccaagctt gacaacgttt     780

ggaagcaaca agatgttgat ctttgttgca gggaatgatg aactgagaga cagaggaatc     840

tggttctatg aggctgtgaa gaagagtgag tgggaaggtg atgtggaact cattcgagtg     900

gatggagagg agcattgctt ccagatttac catcctgaat ctgagaattc taaagacatg     960

atgaagcgca tagcttcttt ccttgtttga                                      990


<210> SEQ ID NO 16
<211> LENGTH: 329
<212> TYPE: PRT
<213> ORGANISM: Lotus japonicus

<400> SEQUENCE: 16

Met Ala Ser Ala Thr Thr Thr Pro Thr Lys Glu Ile Asp Arg Asp Leu
1               5                   10                  15

Pro Pro Leu Leu Arg Val Tyr Lys Asp Gly Thr Val Glu Arg Leu Leu
            20                  25                  30

Gly Ser Pro Val Val Pro Ala Ile Pro His Asp Pro Glu Thr Glu Val
        35                  40                  45

Ser Ser Lys Asp Ile Val Ile Ser Gln Thr Pro Leu Ile Ser Ala Arg
    50                  55                  60

Ile His Leu Pro Lys Gln Ser Asn Pro Gln Asn Pro Lys Val Pro Ile
65                  70                  75                  80
```

```
Leu Ile Tyr Tyr His Gly Gly Ala Phe Cys Leu Glu Ser Ala Phe Ser
                85                  90                  95

Phe Leu His Gln Arg Tyr Leu Asn Ile Val Ala Ser Arg Ser Asn Val
            100                 105                 110

Val Val Val Ser Val Glu Tyr Arg Leu Ala Pro Glu His Pro Leu Pro
        115                 120                 125

Ala Ala Tyr Glu Asp Gly Trp Glu Ala Leu Lys Trp Val Thr Ser His
    130                 135                 140

Ser Thr Asp Asn Lys Pro Ile Asn Ser Glu Pro Trp Leu Ile Glu His
145                 150                 155                 160

Gly Asp Phe Ser Arg Phe Tyr Ile Gly Gly Asp Thr Ser Gly Ala Asn
                165                 170                 175

Ile Ala Tyr His Val Gly Leu Arg Val Gly Gly Gly Val Glu Lys Leu
            180                 185                 190

Pro Gly Asp Val Lys Ile Ala Gly Ala Leu Leu Ala Phe Pro Leu Phe
        195                 200                 205

Trp Ser Ser Tyr Pro Val Leu Glu Glu Pro Val Glu Gly Phe Glu Gln
    210                 215                 220

Ser Leu Ser Arg Lys Val Trp Asn Phe Val Tyr Pro Asp Ala Pro Gly
225                 230                 235                 240

Gly Ile Asp Asn Pro Leu Ile Asn Pro Leu Ala Asp Gly Ala Pro Ser
                245                 250                 255

Leu Thr Thr Phe Gly Ser Asn Lys Met Leu Ile Phe Val Ala Gly Asn
            260                 265                 270

Asp Glu Leu Arg Asp Arg Gly Ile Trp Phe Tyr Glu Ala Val Lys Lys
        275                 280                 285

Ser Glu Trp Glu Gly Asp Val Glu Leu Ile Arg Val Asp Gly Glu Glu
    290                 295                 300

His Cys Phe Gln Ile Tyr His Pro Glu Ser Glu Asn Ser Lys Asp Met
305                 310                 315                 320

Met Lys Arg Ile Ala Ser Phe Leu Val
                325
```

<210> SEQ ID NO 17
<211> LENGTH: 720
<212> TYPE: DNA
<213> ORGANISM: Torenia hybrid cultivar

<400> SEQUENCE: 17

```
atgaaagata agttctatgg caccattttg cagagcgaag ccctcgcaaa gtatctgtta      60

gagacaagtg cctatccacg agaacatccg cagctcaaag aactaaggag cgcaactgtg     120

gacaagtatc aatattggag cttgatgaat gttccagctg atgaggggca gttcatttca     180

atgttactga aaattatgaa cgcaaaaaag acaattgaag ttggagtttt cacaggctac     240

tcactcctat caactgctct ggctctacct gatgatggca aaatcgttgc cattgatcct     300

gatagagaag cttatgagac tggtttgcca tttatcaaga aagcaaacgt ggctcataaa     360

atccaataca tacaatctga tgccatgaaa gtcatgaatg acctcattgc tgccaaggga     420

gaagaagaag aggggagctt tgactttggg ttcgtggatg cagacaaaga aaactacata     480

aactaccacg agaaactgtt gaagctggtt aaggttggag ggatcatagg atacgacaac     540

actctgtggt ctggaacagt tgctgcatct gaagacgatg agaataatat gcaagactac     600

ttaagaggtt gcagagggca tatcctcaaa ctaaactcct ttctcgcaaa cgatgatcgg     660

attgaattgg ctcacctctc tattggagat ggactcacct tgtgcaaacg tctcaaataa     720
```

<210> SEQ ID NO 18
<211> LENGTH: 239
<212> TYPE: PRT
<213> ORGANISM: Torenia hybrid cultivar

<400> SEQUENCE: 18

```
Met Lys Asp Lys Phe Tyr Gly Thr Ile Leu Gln Ser Glu Ala Leu Ala
1               5                   10                  15

Lys Tyr Leu Leu Glu Thr Ser Ala Tyr Pro Arg Glu His Pro Gln Leu
            20                  25                  30

Lys Glu Leu Arg Ser Ala Thr Val Asp Lys Tyr Gln Tyr Trp Ser Leu
        35                  40                  45

Met Asn Val Pro Ala Asp Glu Gly Gln Phe Ile Ser Met Leu Leu Lys
    50                  55                  60

Ile Met Asn Ala Lys Lys Thr Ile Glu Val Gly Val Phe Thr Gly Tyr
65                  70                  75                  80

Ser Leu Leu Ser Thr Ala Leu Ala Leu Pro Asp Asp Gly Lys Ile Val
                85                  90                  95

Ala Ile Asp Pro Asp Arg Glu Ala Tyr Glu Thr Gly Leu Pro Phe Ile
            100                 105                 110

Lys Lys Ala Asn Val Ala His Lys Ile Gln Tyr Ile Gln Ser Asp Ala
        115                 120                 125

Met Lys Val Met Asn Asp Leu Ile Ala Ala Lys Gly Glu Glu Glu Glu
    130                 135                 140

Gly Ser Phe Asp Phe Gly Phe Val Asp Ala Asp Lys Glu Asn Tyr Ile
145                 150                 155                 160

Asn Tyr His Glu Lys Leu Leu Lys Leu Val Lys Val Gly Gly Ile Ile
                165                 170                 175

Gly Tyr Asp Asn Thr Leu Trp Ser Gly Thr Val Ala Ala Ser Glu Asp
            180                 185                 190

Asp Glu Asn Asn Met Gln Asp Tyr Leu Arg Gly Cys Arg Gly His Ile
        195                 200                 205

Leu Lys Leu Asn Ser Phe Leu Ala Asn Asp Asp Arg Ile Glu Leu Ala
    210                 215                 220

His Leu Ser Ile Gly Asp Gly Leu Thr Leu Cys Lys Arg Leu Lys
225                 230                 235
```

<210> SEQ ID NO 19
<211> LENGTH: 1539
<212> TYPE: DNA
<213> ORGANISM: Torenia hybrid cultivar

<400> SEQUENCE: 19

```
atggacacag tcttaatcac actctacacc gccctgttcg tcatcaccac caccttcctc      60

ctcctcctcc gccgaagggg accaccgtct ccgcccggtc ctctctccct acccataatt     120

ggccacctcc acctcctcgg cccaagactc caccacacgt tccatgaatt ctcactcaaa     180

tacggcccat tgatccagct caagctcggc tcgatcccgt gcgtcgtggc ctcgacgccc     240

gagctcgcga gagagtttct taagacgaac gagctcgcgt tctcctctcg caagcactct     300

acggccatag acatcgtcac ctacgactcg tcctttgctt tctctccgta cggaccctac     360

tggaagtaca tcaagaaact gtgtacctac gagctgctcg gagcgaggaa cctcggacac     420

tttcagccca ttaggaatct cgaggtcagg tcctttctgc agcttctgat gcacaagagc     480

tttaagggcg agagtgtgaa tgtgacagac gagctggtga ggctgacgag caatgtgata     540
```

```
tcccacatga tgctgagcat aaggtgctcg gaagatgaag gcgatgctga ggcggcgaga    600

acagtgatac gcgaggtgac gcagatattt ggggaattcg atgttacgga cataatatgg    660

ttttgcaaga aattcgatct gcaggggata aagaagaggt cagaggatat tcagaggagg    720

tatgatgctt tgctcgagaa gattattagt gatagagaga gatcgaggag gcaaaatcgt    780

gataagcatg gtggcggtaa caatgaggag gccaaggatt ttcttgatat gttgcttgat    840

gtgatggaga gtggggacac ggaggtcaaa ttcactagag agcatctcaa ggctttgatt    900

ctggatttct tcacggccgg tacggacaca acagccatag ccaccgagtg ggccatcgcc    960

gagctcatca acaacccgaa cgtcttgaag aaggcccaag aagaaatatc ccggatcatc   1020

ggaaccaagc ggatcgtaca agaatccgac gccccagacc taccctacct ccaggccatc   1080

atcaaggaga cgttccggct ccacccaccg atcccgatgc tctcgcgtaa gtccacctcc   1140

gattgcacgg tcaacggcta caaaatccaa gccaagagcc tcttgttcgt gaacatatgg   1200

tccatcggtc gaaaccctaa ttactgggaa agccctatgg agttcaggcc cgagcggttc   1260

ttggagaagg gacgcgagtc catcgacgtc aagggccagc actttgagct cttgcctttt   1320

gggacgggcc gcaggggctg tcccggtatg ttgctggcta tacaagaggt ggtcagcatc   1380

attgggacca tggttcagtg cttcgactgg aaattggcag atggttcggg caataatgtg   1440

gacatgaccg aacggtctgg attgaccgct ccgagagcgt tcgatctggt ttgccggttg   1500

tatccacggg ttgacccggc cacaatatcg ggtgcttga                          1539


<210> SEQ ID NO 20
<211> LENGTH: 512
<212> TYPE: PRT
<213> ORGANISM: Torenia hybrid cultivar

<400> SEQUENCE: 20

Met Asp Thr Val Leu Ile Thr Leu Tyr Thr Ala Leu Phe Val Ile Thr
1               5                   10                  15

Thr Thr Phe Leu Leu Leu Leu Arg Arg Arg Gly Pro Pro Ser Pro Pro
            20                  25                  30

Gly Pro Leu Ser Leu Pro Ile Ile Gly His Leu His Leu Leu Gly Pro
        35                  40                  45

Arg Leu His His Thr Phe His Glu Phe Ser Leu Lys Tyr Gly Pro Leu
    50                  55                  60

Ile Gln Leu Lys Leu Gly Ser Ile Pro Cys Val Val Ala Ser Thr Pro
65                  70                  75                  80

Glu Leu Ala Arg Glu Phe Leu Lys Thr Asn Glu Leu Ala Phe Ser Ser
                85                  90                  95

Arg Lys His Ser Thr Ala Ile Asp Ile Val Thr Tyr Asp Ser Ser Phe
            100                 105                 110

Ala Phe Ser Pro Tyr Gly Pro Tyr Trp Lys Tyr Ile Lys Lys Leu Cys
        115                 120                 125

Thr Tyr Glu Leu Leu Gly Ala Arg Asn Leu Gly His Phe Gln Pro Ile
    130                 135                 140

Arg Asn Leu Glu Val Arg Ser Phe Leu Gln Leu Leu Met His Lys Ser
145                 150                 155                 160

Phe Lys Gly Glu Ser Val Asn Val Thr Asp Glu Leu Val Arg Leu Thr
                165                 170                 175

Ser Asn Val Ile Ser His Met Met Leu Ser Ile Arg Cys Ser Glu Asp
            180                 185                 190
```

```
Glu Gly Asp Ala Glu Ala Ala Arg Thr Val Ile Arg Glu Val Thr Gln
        195                 200                 205

Ile Phe Gly Glu Phe Asp Val Thr Asp Ile Ile Trp Phe Cys Lys Lys
    210                 215                 220

Phe Asp Leu Gln Gly Ile Lys Lys Arg Ser Glu Asp Ile Gln Arg Arg
225                 230                 235                 240

Tyr Asp Ala Leu Leu Glu Lys Ile Ile Ser Asp Arg Glu Arg Ser Arg
                245                 250                 255

Arg Gln Asn Arg Asp Lys His Gly Gly Gly Asn Asn Glu Glu Ala Lys
            260                 265                 270

Asp Phe Leu Asp Met Leu Leu Asp Val Met Glu Ser Gly Asp Thr Glu
        275                 280                 285

Val Lys Phe Thr Arg Glu His Leu Lys Ala Leu Ile Leu Asp Phe Phe
    290                 295                 300

Thr Ala Gly Thr Asp Thr Thr Ala Ile Ala Thr Glu Trp Ala Ile Ala
305                 310                 315                 320

Glu Leu Ile Asn Asn Pro Asn Val Leu Lys Lys Ala Gln Glu Glu Ile
                325                 330                 335

Ser Arg Ile Ile Gly Thr Lys Arg Ile Val Gln Glu Ser Asp Ala Pro
            340                 345                 350

Asp Leu Pro Tyr Leu Gln Ala Ile Ile Lys Glu Thr Phe Arg Leu His
        355                 360                 365

Pro Pro Ile Pro Met Leu Ser Arg Lys Ser Thr Ser Asp Cys Thr Val
    370                 375                 380

Asn Gly Tyr Lys Ile Gln Ala Lys Ser Leu Leu Phe Val Asn Ile Trp
385                 390                 395                 400

Ser Ile Gly Arg Asn Pro Asn Tyr Trp Glu Ser Pro Met Glu Phe Arg
                405                 410                 415

Pro Glu Arg Phe Leu Glu Lys Gly Arg Glu Ser Ile Asp Val Lys Gly
            420                 425                 430

Gln His Phe Glu Leu Leu Pro Phe Gly Thr Gly Arg Arg Gly Cys Pro
        435                 440                 445

Gly Met Leu Leu Ala Ile Gln Glu Val Val Ser Ile Ile Gly Thr Met
    450                 455                 460

Val Gln Cys Phe Asp Trp Lys Leu Ala Asp Gly Ser Gly Asn Asn Val
465                 470                 475                 480

Asp Met Thr Glu Arg Ser Gly Leu Thr Ala Pro Arg Ala Phe Asp Leu
                485                 490                 495

Val Cys Arg Leu Tyr Pro Arg Val Asp Pro Ala Thr Ile Ser Gly Ala
            500                 505                 510


<210> SEQ ID NO 21
<211> LENGTH: 1434
<212> TYPE: DNA
<213> ORGANISM: Gentiana triflora

<400> SEQUENCE: 21

atgggttctt taaccaacaa tgataatctt catattttct tagtgtgttt cattggtcaa     60

ggagttgtaa atcctatgct aagacttggc aaggcctttg cttcaaaggg tctattagtc    120

actttgtctg caccagaaat tgttggcaca gaaattagga aagccaataa cctcaatgat    180

gatcaaccca taaaagttgg tagtgggatg atcagatttg agttctttga tgatggatgg    240

gaatctgtta atgggtctaa accctttgat gtttgggtgt acatcaatca tcttgatcaa    300

actgggagac aaaaactccc aattatgctc aagaaacatg aagaaacagg gacccctgtt    360
```

```
tcttgtttga ttctcaatcc tttagttcca tgggttgcag atgttgcaga cagccttcaa    420

atcccttgtg ctactctttg ggttcaatct tgtgccagtt tttctgctta ttaccattat    480

caccatggtc tggtaccttt ccctactgaa tctgaaccag aaattgatgt ccaattacca    540

ggtatgccat tgttgaagta cgatgaagtt cctgattatt tgcatccaag aactccgtat    600

cccttctttg ggaccaatat tctgggtcaa ttcaagaact tgtccaagaa tttctgcata    660

ttgatggaca ctttctatga actcgaacac gagattatag acaacatgtg caagttatgt    720

ccaattaagc ctattggacc cttgttcaag atcccaaaag atcccagctc aaatggtatt    780

actggaaatt tcatgaaggt ggatgattgt aaagagtggc tggacagtag accgacgtcc    840

acggtggtgt atgtctccgt cggcagcgtc gtttacttga aacaagagca agttactgag    900

atggcctatg ggattttgaa ctctgaagtt tcgttcttgt gggttctgag acctcccagt    960

aaacgaatcg gcactgagcc acatgtcttg ccggaagagt tctgggaaaa agccggcgat   1020

agaggcaagg ttgtgcaatg gagccctcaa gaacaagtct tggcacatcc ggcaaccgta   1080

ggtttcttga ctcattgtgg atggaactcg acgcaggaag ccatatctag cggtgtgccg   1140

gtgataactt tccctcagtt tggtgatcaa gttacgaacg ccaagttctt ggtggaagaa   1200

ttcaaagtcg ggtaagatt gggcagaggt gaacttgaga acagaatcat cactagagac    1260

gaggttgaaa gggctctgag ggagatcacg agcgggccta aggcagaaga ggtgaaagag   1320

aatgcattga aatggaagaa aaaggcggag gagaccgtcg ccaagggcgg ctactcggaa   1380

agaaaccttg ttggtttcat tgaagaggtt gctagaaaaa ctggtaccaa ataa         1434
```

<210> SEQ ID NO 22
<211> LENGTH: 477
<212> TYPE: PRT
<213> ORGANISM: Gentiana triflora

<400> SEQUENCE: 22

```
Met Gly Ser Leu Thr Asn Asn Asp Asn Leu His Ile Phe Leu Val Cys
1               5                   10                  15

Phe Ile Gly Gln Gly Val Val Asn Pro Met Leu Arg Leu Gly Lys Ala
            20                  25                  30

Phe Ala Ser Lys Gly Leu Leu Val Thr Leu Ser Ala Pro Glu Ile Val
        35                  40                  45

Gly Thr Glu Ile Arg Lys Ala Asn Asn Leu Asn Asp Asp Gln Pro Ile
    50                  55                  60

Lys Val Gly Ser Gly Met Ile Arg Phe Glu Phe Phe Asp Asp Gly Trp
65                  70                  75                  80

Glu Ser Val Asn Gly Ser Lys Pro Phe Asp Val Trp Val Tyr Ile Asn
                85                  90                  95

His Leu Asp Gln Thr Gly Arg Gln Lys Leu Pro Ile Met Leu Lys Lys
            100                 105                 110

His Glu Glu Thr Gly Thr Pro Val Ser Cys Leu Ile Leu Asn Pro Leu
        115                 120                 125

Val Pro Trp Val Ala Asp Val Ala Asp Ser Leu Gln Ile Pro Cys Ala
    130                 135                 140

Thr Leu Trp Val Gln Ser Cys Ala Ser Phe Ser Ala Tyr Tyr His Tyr
145                 150                 155                 160

His His Gly Leu Val Pro Phe Pro Thr Glu Ser Glu Pro Glu Ile Asp
                165                 170                 175

Val Gln Leu Pro Gly Met Pro Leu Leu Lys Tyr Asp Glu Val Pro Asp
```

```
            180                 185                 190

Tyr Leu His Pro Arg Thr Pro Tyr Pro Phe Phe Gly Thr Asn Ile Leu
        195                 200                 205

Gly Gln Phe Lys Asn Leu Ser Lys Asn Phe Cys Ile Leu Met Asp Thr
    210                 215                 220

Phe Tyr Glu Leu Glu His Glu Ile Ile Asp Asn Met Cys Lys Leu Cys
225                 230                 235                 240

Pro Ile Lys Pro Ile Gly Pro Leu Phe Lys Ile Pro Lys Asp Pro Ser
                245                 250                 255

Ser Asn Gly Ile Thr Gly Asn Phe Met Lys Val Asp Asp Cys Lys Glu
            260                 265                 270

Trp Leu Asp Ser Arg Pro Thr Ser Thr Val Val Tyr Val Ser Val Gly
        275                 280                 285

Ser Val Val Tyr Leu Lys Gln Glu Gln Val Thr Glu Met Ala Tyr Gly
    290                 295                 300

Ile Leu Asn Ser Glu Val Ser Phe Leu Trp Val Leu Arg Pro Pro Ser
305                 310                 315                 320

Lys Arg Ile Gly Thr Glu Pro His Val Leu Pro Glu Glu Phe Trp Glu
                325                 330                 335

Lys Ala Gly Asp Arg Gly Lys Val Val Gln Trp Ser Pro Gln Glu Gln
            340                 345                 350

Val Leu Ala His Pro Ala Thr Val Gly Phe Leu Thr His Cys Gly Trp
        355                 360                 365

Asn Ser Thr Gln Glu Ala Ile Ser Ser Gly Val Pro Val Ile Thr Phe
    370                 375                 380

Pro Gln Phe Gly Asp Gln Val Thr Asn Ala Lys Phe Leu Val Glu Glu
385                 390                 395                 400

Phe Lys Val Gly Val Arg Leu Gly Arg Gly Glu Leu Glu Asn Arg Ile
                405                 410                 415

Ile Thr Arg Asp Glu Val Glu Arg Ala Leu Arg Glu Ile Thr Ser Gly
            420                 425                 430

Pro Lys Ala Glu Glu Val Lys Glu Asn Ala Leu Lys Trp Lys Lys Lys
        435                 440                 445

Ala Glu Glu Thr Val Ala Lys Gly Gly Tyr Ser Glu Arg Asn Leu Val
    450                 455                 460

Gly Phe Ile Glu Glu Val Ala Arg Lys Thr Gly Thr Lys
465                 470                 475
```

<210> SEQ ID NO 23
<211> LENGTH: 58
<212> TYPE: DNA
<213> ORGANISM: Arabidopsis thaliana

<400> SEQUENCE: 23

```
tacatcacaa tcacacaaaa ctaacaaaag atcaaaagca agttcttcac tgttgata       58
```

<210> SEQ ID NO 24
<211> LENGTH: 1356
<212> TYPE: DNA
<213> ORGANISM: Lavandula angustifolia

<400> SEQUENCE: 24

```
atgaccaccc tcctcgaatc ctcccgagtg gcgccgcctc caggcacggt ggctgagcag     60

tcactcccgc tcaccttctt cgacatgacg tggctgcatt tccaccccat gcttcagctt    120

ctcttctacg aactcccctg ttccaaaccc gccttcctcg aaaccgtcgt tccgaaactc    180
```

```
aaacaatcct tatctctaac cctcaaacac ttcttccccc tttcatgcaa tctaatctac    240
cctctatcgc cggagaaaat gccggagttc cggtatcaga acggtgactc ggtttctttc    300
acgattatgg agtctagcga cgattatgaa gatctcgtcg gagatcatcc gcattccgct    360
cataaatact actgctttgc ccctcagctg ccgccgatag tcgaggaatc tgatcggaaa    420
ttgtttcaag ttttagccgt gcaagtgact ctgtttcccg gtcgcggggt gtgcatcgga    480
ataacgacgc accacaccgt tagcgatgct ccatcgtttg tagggtttat gaagagttgg    540
gcttccatca ctaaattcgg aggagatgat gaattcttgg acggaaaagg tgaatgtttg    600
ccggttttcg accgatcgct cgtgaattat ccgcctaaat tggacacata tttatggaac    660
aacgcgcaga aacgtccgtt ggaatcgcag catccatctt taccgacgga tcggattcga    720
gctacctacc ttttcaccca atctgaaatt aagaaattga agggtttgat tcagagaaaa    780
gccccaaatg tagttaatct ctcttccttc gtcgcgatcg cagcttatat ctggaccggc    840
atcgccaaat cggtcggaga ttacaaagac gtggatgacg acaaacgcgc tttcttttta    900
attccgatcg atttaaggcc gcgtttggat ccgccggctc cggggaacta cttcggaaac    960
tgtctatcgt ttgcgatggc gaagatcctg cggcgggatt tggtcggaga tgaaggggtg   1020
tttcgggcag ctgaggcgat cgcggcggaa atagagaaga ggacgagcga caagaagatt   1080
ctagaaactg tggagaactg gccgtctgag attcgcgaag ccttgcaaaa ctgttatttc   1140
tcggtggcgg gatcgagcag gcttgatctt tacggcgcgg atttggatgg gggtaaggcg   1200
gtgaagcaag agatactgtc gattgatgga gagaagttta cgatgtcgtt gtgtaaaccg   1260
agggatgctg ccggaggatt ggaggttgga ttgtctttgc caaaggagga attgcaagct   1320
tttgatgatt attttgcgga gggaataaag ggttga                             1356
```

<210> SEQ ID NO 25
<211> LENGTH: 451
<212> TYPE: PRT
<213> ORGANISM: Lavandula angustifolia

<400> SEQUENCE: 25

```
Met Thr Thr Leu Leu Glu Ser Ser Arg Val Ala Pro Pro Pro Gly Thr
1               5                   10                  15

Val Ala Glu Gln Ser Leu Pro Leu Thr Phe Phe Asp Met Thr Trp Leu
            20                  25                  30

His Phe His Pro Met Leu Gln Leu Leu Phe Tyr Glu Leu Pro Cys Ser
        35                  40                  45

Lys Pro Ala Phe Leu Glu Thr Val Val Pro Lys Leu Lys Gln Ser Leu
    50                  55                  60

Ser Leu Thr Leu Lys His Phe Phe Pro Leu Ser Cys Asn Leu Ile Tyr
65                  70                  75                  80

Pro Leu Ser Pro Glu Lys Met Pro Glu Phe Arg Tyr Gln Asn Gly Asp
                85                  90                  95

Ser Val Ser Phe Thr Ile Met Glu Ser Ser Asp Asp Tyr Glu Asp Leu
            100                 105                 110

Val Gly Asp His Pro His Ser Ala His Lys Tyr Tyr Cys Phe Ala Pro
        115                 120                 125

Gln Leu Pro Pro Ile Val Glu Glu Ser Asp Arg Lys Leu Phe Gln Val
    130                 135                 140

Leu Ala Val Gln Val Thr Leu Phe Pro Gly Arg Gly Val Cys Ile Gly
145                 150                 155                 160
```

```
Ile Thr Thr His His Thr Val Ser Asp Ala Pro Ser Phe Val Gly Phe
                165                 170                 175

Met Lys Ser Trp Ala Ser Ile Thr Lys Phe Gly Gly Asp Asp Glu Phe
            180                 185                 190

Leu Asp Gly Lys Gly Glu Cys Leu Pro Val Phe Asp Arg Ser Leu Val
        195                 200                 205

Asn Tyr Pro Pro Lys Leu Asp Thr Tyr Leu Trp Asn Asn Ala Gln Lys
    210                 215                 220

Arg Pro Leu Glu Ser Gln His Pro Ser Leu Pro Thr Asp Arg Ile Arg
225                 230                 235                 240

Ala Thr Tyr Leu Phe Thr Gln Ser Glu Ile Lys Lys Leu Lys Gly Leu
                245                 250                 255

Ile Gln Arg Lys Ala Pro Asn Val Val Asn Leu Ser Ser Phe Val Ala
            260                 265                 270

Ile Ala Ala Tyr Ile Trp Thr Gly Ile Ala Lys Ser Val Gly Asp Tyr
        275                 280                 285

Lys Asp Val Asp Asp Asp Lys Arg Ala Phe Phe Leu Ile Pro Ile Asp
    290                 295                 300

Leu Arg Pro Arg Leu Asp Pro Pro Ala Pro Gly Asn Tyr Phe Gly Asn
305                 310                 315                 320

Cys Leu Ser Phe Ala Met Ala Lys Ile Leu Arg Arg Asp Leu Val Gly
                325                 330                 335

Asp Glu Gly Val Phe Arg Ala Ala Glu Ala Ile Ala Ala Glu Ile Glu
            340                 345                 350

Lys Arg Thr Ser Asp Lys Lys Ile Leu Glu Thr Val Glu Asn Trp Pro
        355                 360                 365

Ser Glu Ile Arg Glu Ala Leu Gln Asn Cys Tyr Phe Ser Val Ala Gly
    370                 375                 380

Ser Ser Arg Leu Asp Leu Tyr Gly Ala Asp Phe Gly Trp Gly Lys Ala
385                 390                 395                 400

Val Lys Gln Glu Ile Leu Ser Ile Asp Gly Glu Lys Phe Thr Met Ser
                405                 410                 415

Leu Cys Lys Pro Arg Asp Ala Ala Gly Gly Leu Glu Val Gly Leu Ser
            420                 425                 430

Leu Pro Lys Glu Glu Leu Gln Ala Phe Asp Asp Tyr Phe Ala Glu Gly
        435                 440                 445

Ile Lys Gly
    450
```

<210> SEQ ID NO 26
<211> LENGTH: 1344
<212> TYPE: DNA
<213> ORGANISM: Clitoria ternatea L.

<400> SEQUENCE: 26

```
atggaaaaca ataagcatgt cgtaatcttc ccatttccct ttggaagcca ccttccacct      60

ctcttgaacc tcgtcttcaa actcgctcac gccgctccaa acacttcatt ctcattcatc     120

ggcacacaca cttccaacgc attccttttc actaaacgcc acgtcccaga caacatcagg     180

gtcttcacca tcagcgatgg aatcccagag ggttatgtgc ccggcaacaa cccaatcgta     240

aaactcgatt ttttcctctc cactggtccc gacaacttgt gcaagggcat tgaacttgcc     300

gttgcagaga ccaaacagag tgtcacttgc atcattgccg atgcttttgt aacctcttct     360

ctccttgtgg ctcagaccct caatgttcct tggattgtgt tttggcccaa tgtgtcatgc     420
```

```
tcactttctc tttacttcag cattgatttg ataagagaca agtgtacgaa tgatgctaaa    480

aacgcaagct tggatttcct tcctgggttg tccaaattgc gcgttgagga tgtcccacgg    540

ccacaggcca ttgttttgga tggaaaggag acactgtttg caaggacgtt gaattcgttg    600

ggtacggtgt tacctcaagc taaggcggtg gttgtgaatt tctttgcaga attagaccca    660

cctttatttg ttaaggatat gagatccaag ttgcagtctt tgctcttcgt tgatccactt    720

ccatgcccac aattgctact ccctgagaca gattcaaatg ggtgcatgtc gtggttggat    780

tccaagagtt ctagatccgt ggcttatgtt tgttttggaa ccgcggtgag tctaccgcca    840

caagaagttg tagaggtcgc agaggcattg gaggaaagtg gttttccatt tcttttggcc    900

ctcagtgaaa gtctaattgg tgttttgcca aaagggttgg ttgagaggac catgacccgt    960

gggaaagtgg tgtcttgggc accacagtct ctcgttttat cgcatggttc tgttggagta   1020

tttgtgactc actgtggagc taactctgtg actgagagta tttccaatgg ggttcctatg   1080

atatgcaggc ccttctttgg ggaccaagga atagctgcac gggttataca ggatatttgg   1140

gagattgggg tgatcctaga aggtaggatt tttaccaaaa atgggtttgt gaaaaacttg   1200

aatctaattc tggtgcagga agaagggaag aagatcaggg acaatgctct taaagtgaag   1260

cagattgtgc aagatgcagc tggccacat ggacaagctg cagaggattt caacactttg    1320

gtggaaatga tttcctctag ctaa                                          1344


<210> SEQ ID NO 27
<211> LENGTH: 447
<212> TYPE: PRT
<213> ORGANISM: Clitoria ternatea L.

<400> SEQUENCE: 27

Met Glu Asn Asn Lys His Val Val Ile Phe Pro Phe Pro Phe Gly Ser
1               5                   10                  15

His Leu Pro Pro Leu Leu Asn Leu Val Phe Lys Leu Ala His Ala Ala
            20                  25                  30

Pro Asn Thr Ser Phe Ser Phe Ile Gly Thr His Thr Ser Asn Ala Phe
        35                  40                  45

Leu Phe Thr Lys Arg His Val Pro Asp Asn Ile Arg Val Phe Thr Ile
    50                  55                  60

Ser Asp Gly Ile Pro Glu Gly Tyr Val Pro Gly Asn Asn Pro Ile Val
65                  70                  75                  80

Lys Leu Asp Phe Phe Leu Ser Thr Gly Pro Asp Asn Leu Cys Lys Gly
                85                  90                  95

Ile Glu Leu Ala Val Ala Glu Thr Lys Gln Ser Val Thr Cys Ile Ile
            100                 105                 110

Ala Asp Ala Phe Val Thr Ser Ser Leu Leu Val Ala Gln Thr Leu Asn
        115                 120                 125

Val Pro Trp Ile Val Phe Trp Pro Asn Val Ser Cys Ser Leu Ser Leu
    130                 135                 140

Tyr Phe Ser Ile Asp Leu Ile Arg Asp Lys Cys Thr Asn Asp Ala Lys
145                 150                 155                 160

Asn Ala Ser Leu Asp Phe Leu Pro Gly Leu Ser Lys Leu Arg Val Glu
                165                 170                 175

Asp Val Pro Arg Pro Gln Ala Ile Val Leu Asp Gly Lys Glu Thr Leu
            180                 185                 190

Phe Ala Arg Thr Leu Asn Ser Leu Gly Thr Val Leu Pro Gln Ala Lys
        195                 200                 205
```

```
Ala Val Val Val Asn Phe Phe Ala Glu Leu Asp Pro Pro Leu Phe Val
    210                 215                 220

Lys Asp Met Arg Ser Lys Leu Gln Ser Leu Leu Phe Val Asp Pro Leu
225                 230                 235                 240

Pro Cys Pro Gln Leu Leu Leu Pro Glu Thr Asp Ser Asn Gly Cys Met
                245                 250                 255

Ser Trp Leu Asp Ser Lys Ser Ser Arg Ser Val Ala Tyr Val Cys Phe
            260                 265                 270

Gly Thr Ala Val Ser Leu Pro Pro Gln Glu Val Val Glu Val Ala Glu
        275                 280                 285

Ala Leu Glu Glu Ser Gly Phe Pro Phe Leu Leu Ala Leu Ser Glu Ser
    290                 295                 300

Leu Ile Gly Val Leu Pro Lys Gly Leu Val Glu Arg Thr Met Thr Arg
305                 310                 315                 320

Gly Lys Val Val Ser Trp Ala Pro Gln Ser Leu Val Leu Ser His Gly
                325                 330                 335

Ser Val Gly Val Phe Val Thr His Cys Gly Ala Asn Ser Val Thr Glu
            340                 345                 350

Ser Ile Ser Asn Gly Val Pro Met Ile Cys Arg Pro Phe Phe Gly Asp
        355                 360                 365

Gln Gly Ile Ala Ala Arg Val Ile Gln Asp Ile Trp Glu Ile Gly Val
    370                 375                 380

Ile Leu Glu Gly Arg Ile Phe Thr Lys Asn Gly Phe Val Lys Asn Leu
385                 390                 395                 400

Asn Leu Ile Leu Val Gln Glu Glu Gly Lys Lys Ile Arg Asp Asn Ala
                405                 410                 415

Leu Lys Val Lys Gln Ile Val Gln Asp Ala Ala Gly Pro His Gly Gln
            420                 425                 430

Ala Ala Glu Asp Phe Asn Thr Leu Val Glu Met Ile Ser Ser Ser
        435                 440                 445


<210> SEQ ID NO 28
<211> LENGTH: 1422
<212> TYPE: DNA
<213> ORGANISM: Rosa hybrida

<400> SEQUENCE: 28

atgggtggtg atgctatagt tttgtatcca tatccaggac taggccacct aatttccatg     60

gtagagcttg gcaagctctt actcactcac caccettctt tctccatcac aatcctcgcc    120

tcaactgcgc caaccaccat tgcagccacc gccaaactgg tcgccagctc caatgatcag    180

ttgacaaact acatcaaagc cgtctctgcc gacaaccctg ccatcaactt ccaccatctc    240

ccaaccattt cttctcttcc agaacacatt gagaagctca acctcccttt cgaatatgca    300

cgtctccaaa tccccaacat cctccaagtc ctccaaaccc ttaagtcaag cctcaaagcc    360

cttatcctcg acatgttttg tgacgcattg ttcgacgtca cgaaagacct caacatccct    420

acattctact tctacacctc cgcaggaagg agtcttgctg tcttactcaa catccccacc    480

ttccatcgca caaccaacag tctgtctgat tttggcgacg tcccgatttc catttcgggc    540

atgccgccga ttcctgtttc ggcaatgccc aagctgttgt ttgaccgctc tactaatttc    600

tacaagagct tcctgtcgac ttcaactcac atggcaaagt caaatggaat cattctcaac    660

acgtttgatc tgctggaaga gagggccctc aaagcgttga gggctggact gtgcttgcct    720

aaccaaccca cacctccgat cttcaccgtc ggaccgttga tctcagggaa gagtggagat    780
```

```
aatgatgagc atgagagctt gaagtggcta aacaaccagc ccaaagacag cgttgtgttt    840

ctatgtttcg gaagcatggg agtgttttct atcaaacagt tggaggccat ggctttaggt    900

ttagagaaaa gtggccagag gtttttgtgg gtggtacgta atccacctat agaagagtta    960

ccggtagagg agccaagttt ggaggaaata ttgccaaagg gttttgtgga aagaacaaag   1020

gataggggac tggtggtgag gaagtgggcg cctcaggtgg aggtactaag tcatgactcg   1080

gtgggcgggt tcgtgactca ctgtgggtgg aactcggttt tggaagcagt gtgtaatggg   1140

gtgccgatgg ttgcgtggcc tttgtacgcg gagcaaaagc tgggcagggt gtttctggtg   1200

gaggagatga aggtggctgt gggggtgaaa gagtccgaaa ccgggtttgt gagtgcggac   1260

gagttggaga agcgagtgag ggagttgatg gactccgaga gtggggatga aataagaggg   1320

agggtttcgg agttcagtaa tggtggcgtg aaggccaagg aagaaggtgg gtcttctgtt   1380

gcttccttgg ccaagttggc tcagctgtgg aagcaaaaat ga                      1422
```

<210> SEQ ID NO 29
<211> LENGTH: 473
<212> TYPE: PRT
<213> ORGANISM: Rosa hybrida

<400> SEQUENCE: 29

```
Met Gly Gly Asp Ala Ile Val Leu Tyr Pro Tyr Pro Gly Leu Gly His
1               5                   10                  15

Leu Ile Ser Met Val Glu Leu Gly Lys Leu Leu Leu Thr His His Pro
            20                  25                  30

Ser Phe Ser Ile Thr Ile Leu Ala Ser Thr Ala Pro Thr Thr Ile Ala
        35                  40                  45

Ala Thr Ala Lys Leu Val Ala Ser Ser Asn Asp Gln Leu Thr Asn Tyr
    50                  55                  60

Ile Lys Ala Val Ser Ala Asp Asn Pro Ala Ile Asn Phe His His Leu
65                  70                  75                  80

Pro Thr Ile Ser Ser Leu Pro Glu His Ile Glu Lys Leu Asn Leu Pro
                85                  90                  95

Phe Glu Tyr Ala Arg Leu Gln Ile Pro Asn Ile Leu Gln Val Leu Gln
            100                 105                 110

Thr Leu Lys Ser Ser Leu Lys Ala Leu Ile Leu Asp Met Phe Cys Asp
        115                 120                 125

Ala Leu Phe Asp Val Thr Lys Asp Leu Asn Ile Pro Thr Phe Tyr Phe
    130                 135                 140

Tyr Thr Ser Ala Gly Arg Ser Leu Ala Val Leu Leu Asn Ile Pro Thr
145                 150                 155                 160

Phe His Arg Thr Thr Asn Ser Leu Ser Asp Phe Gly Asp Val Pro Ile
                165                 170                 175

Ser Ile Ser Gly Met Pro Pro Ile Pro Val Ser Ala Met Pro Lys Leu
            180                 185                 190

Leu Phe Asp Arg Ser Thr Asn Phe Tyr Lys Ser Phe Leu Ser Thr Ser
        195                 200                 205

Thr His Met Ala Lys Ser Asn Gly Ile Ile Leu Asn Thr Phe Asp Leu
    210                 215                 220

Leu Glu Glu Arg Ala Leu Lys Ala Leu Arg Ala Gly Leu Cys Leu Pro
225                 230                 235                 240

Asn Gln Pro Thr Pro Pro Ile Phe Thr Val Gly Pro Leu Ile Ser Gly
                245                 250                 255

Lys Ser Gly Asp Asn Asp Glu His Glu Ser Leu Lys Trp Leu Asn Asn
```

```
            260                 265                 270

Gln Pro Lys Asp Ser Val Val Phe Leu Cys Phe Gly Ser Met Gly Val
        275                 280                 285

Phe Ser Ile Lys Gln Leu Glu Ala Met Ala Leu Gly Leu Glu Lys Ser
    290                 295                 300

Gly Gln Arg Phe Leu Trp Val Val Arg Asn Pro Pro Ile Glu Glu Leu
305                 310                 315                 320

Pro Val Glu Glu Pro Ser Leu Glu Glu Ile Leu Pro Lys Gly Phe Val
                325                 330                 335

Glu Arg Thr Lys Asp Arg Gly Leu Val Val Arg Lys Trp Ala Pro Gln
            340                 345                 350

Val Glu Val Leu Ser His Asp Ser Val Gly Gly Phe Val Thr His Cys
        355                 360                 365

Gly Trp Asn Ser Val Leu Glu Ala Val Cys Asn Gly Val Pro Met Val
    370                 375                 380

Ala Trp Pro Leu Tyr Ala Glu Gln Lys Leu Gly Arg Val Phe Leu Val
385                 390                 395                 400

Glu Glu Met Lys Val Ala Val Gly Val Lys Glu Ser Glu Thr Gly Phe
                405                 410                 415

Val Ser Ala Asp Glu Leu Glu Lys Arg Val Arg Glu Leu Met Asp Ser
            420                 425                 430

Glu Ser Gly Asp Glu Ile Arg Gly Arg Val Ser Glu Phe Ser Asn Gly
        435                 440                 445

Gly Val Lys Ala Lys Glu Glu Gly Gly Ser Ser Val Ala Ser Leu Ala
    450                 455                 460

Lys Leu Ala Gln Leu Trp Lys Gln Lys
465                 470
```

<210> SEQ ID NO 30
<211> LENGTH: 1344
<212> TYPE: DNA
<213> ORGANISM: Perilla frutescens var. crispa

<400> SEQUENCE: 30

```
atgggatttg aattgcacat tggcgttcta gcattccctt tcgggacaca cgctccccct     60

ctactcgccc tggtgcggag gctggcagcc tcctcaccgg gcactctatt ttctttcttg    120

aacagtgcgg agtcaaacgc cgcactgttc aacgagcgca cgtacgataa catacgggcg    180

tttgatgtgt gggacgggac ccccgaaggc cggattttca ccggaactca tttcgaggcc    240

gtcgggttgt tcctcaaggc ctcaccgggt aacttcgaca aggttattga agaggcggaa    300

cgcaaaactg gcctcaaaat ttgctgctta ataactgatg catttttgtg gtttgcttgt    360

gatatggccc agaaaagagg gctgccatgg gtgccattct ggactgctgc ttcctgctct    420

ctctcttcac acctctacac cgatcaaatc gtgaaagcag gaacagcaaa ccaagagcaa    480

aatctatcgt tcattcccgg attggaaatg gcgaccttga ctgatcttcc gccggaggtt    540

ttcctggaca acagtccatc gccgctggcg ataacaatca acaaaatggt cgagaagctc    600

ccaaaatcca ccgccgtcgt cttgaattcc ttcgaagaaa tcgacccgat catcacggat    660

gacctgaaaa caaaattcaa gaatttcctc aacgtaggcc cttcaattct cgcatcaccc    720

cctcaggcga ctcccgacga cgaaacggga tgcctgtcgt ggctggcaga ccaaaccagt    780

cctaaatcag tggtgtacat cagcttcggc accgtgatca cgccgccgga aaacgagctg    840

gcggcattgg ccgacgcctt ggaaatttgc agattcccat ttctttggtc gctgaaagac    900
```

```
tacgccgtga aatccctccc cgacggattc ctcgaccgca cgaaggggtt cgggaagatc    960

gtggcgtggg ctccgcagca gcaagtgctc gcgcatagaa atgttggagt gttcgtcact   1020

cactgcggct ggaactccat tctggaaagc atttccagct gcgtgccgct gatttgcagg   1080

cccttttcg gcgatcagaa gctcaacagc agaatggtgc aggattcgtg gaaaattggg   1140

gtcagagttg aaggaggcgt cttcactaag aatgaagcgg ttgaatcttt aaaaaagttg   1200

atggcgacgg aggcgggaat gaaaattagg gaaaatgtta gtttgctgag agagaaggct   1260

accgctgcag ttaaaccgga ggggagttcg tctcagaatt tcaagaaact gttagagata   1320

attggtgcgg cggagagcag ttaa                                           1344
```

<210> SEQ ID NO 31
<211> LENGTH: 447
<212> TYPE: PRT
<213> ORGANISM: Perilla frutescens var. crispa

<400> SEQUENCE: 31

```
Met Gly Phe Glu Leu His Ile Gly Val Leu Ala Phe Pro Phe Gly Thr
1               5                   10                  15

His Ala Pro Pro Leu Leu Ala Leu Val Arg Arg Leu Ala Ala Ser Ser
            20                  25                  30

Pro Gly Thr Leu Phe Ser Phe Leu Asn Ser Ala Glu Ser Asn Ala Ala
        35                  40                  45

Leu Phe Asn Glu Arg Thr Tyr Asp Asn Ile Arg Ala Phe Asp Val Trp
    50                  55                  60

Asp Gly Thr Pro Glu Gly Arg Ile Phe Thr Gly Thr His Phe Glu Ala
65                  70                  75                  80

Val Gly Leu Phe Leu Lys Ala Ser Pro Gly Asn Phe Asp Lys Val Ile
                85                  90                  95

Glu Glu Ala Glu Arg Lys Thr Gly Leu Lys Ile Cys Cys Leu Ile Thr
            100                 105                 110

Asp Ala Phe Leu Trp Phe Ala Cys Asp Met Ala Gln Lys Arg Gly Leu
        115                 120                 125

Pro Trp Val Pro Phe Trp Thr Ala Ala Ser Cys Ser Leu Ser Ser His
    130                 135                 140

Leu Tyr Thr Asp Gln Ile Val Lys Ala Gly Thr Ala Asn Gln Glu Gln
145                 150                 155                 160

Asn Leu Ser Phe Ile Pro Gly Leu Glu Met Ala Thr Leu Thr Asp Leu
                165                 170                 175

Pro Pro Glu Val Phe Leu Asp Asn Ser Pro Ser Pro Leu Ala Ile Thr
            180                 185                 190

Ile Asn Lys Met Val Glu Lys Leu Pro Lys Ser Thr Ala Val Val Leu
        195                 200                 205

Asn Ser Phe Glu Glu Ile Asp Pro Ile Ile Thr Asp Asp Leu Lys Thr
    210                 215                 220

Lys Phe Lys Asn Phe Leu Asn Val Gly Pro Ser Ile Leu Ala Ser Pro
225                 230                 235                 240

Pro Gln Ala Thr Pro Asp Asp Glu Thr Gly Cys Leu Ser Trp Leu Ala
                245                 250                 255

Asp Gln Thr Ser Pro Lys Ser Val Val Tyr Ile Ser Phe Gly Thr Val
            260                 265                 270

Ile Thr Pro Pro Glu Asn Glu Leu Ala Ala Leu Ala Asp Ala Leu Glu
        275                 280                 285

Ile Cys Arg Phe Pro Phe Leu Trp Ser Leu Lys Asp Tyr Ala Val Lys
```

```
    290                 295                 300

Ser Leu Pro Asp Gly Phe Leu Asp Arg Thr Lys Gly Phe Gly Lys Ile
305                 310                 315                 320

Val Ala Trp Ala Pro Gln Gln Gln Val Leu Ala His Arg Asn Val Gly
                325                 330                 335

Val Phe Val Thr His Cys Gly Trp Asn Ser Ile Leu Glu Ser Ile Ser
            340                 345                 350

Ser Cys Val Pro Leu Ile Cys Arg Pro Phe Phe Gly Asp Gln Lys Leu
        355                 360                 365

Asn Ser Arg Met Val Gln Asp Ser Trp Lys Ile Gly Val Arg Val Glu
    370                 375                 380

Gly Gly Val Phe Thr Lys Asn Glu Ala Val Glu Ser Leu Lys Lys Leu
385                 390                 395                 400

Met Ala Thr Glu Ala Gly Met Lys Ile Arg Glu Asn Val Ser Leu Leu
                405                 410                 415

Arg Glu Lys Ala Thr Ala Ala Val Lys Pro Glu Gly Ser Ser Ser Gln
            420                 425                 430

Asn Phe Lys Lys Leu Leu Glu Ile Ile Gly Ala Ala Glu Ser Ser
        435                 440                 445


<210> SEQ ID NO 32
<211> LENGTH: 1383
<212> TYPE: DNA
<213> ORGANISM: Dahlia

<400> SEQUENCE: 32

ctacgacgca attgcacttt ctaatccatc attaaagatt ttaccaaatg cttccatttg      60

catactcgga aagcacactc caatttcaaa atcttgtgct gattccttgc acgcacttaa     120

agaaaccgac gcgctatagt cgattgaaac aacttcgtat ttcatcgcct ttccccaccc     180

aaaatcaatg tcatagaagt tgagtttcgg tgtacccgag atccccatct tcctagccgg     240

aatcttgaaa ccatcatacc atcggtcggc atcttccaat attccccccct tcttgttcac     300

cattttgctt atcccctctc caatcaattt agcagccata acaaatccat tttcaccttt     360

taacacacca ttttttatgg tcacaataca cggcgcgcta cagttaccaa aatagttttc     420

aggaagtggc ggatccaaac gtgatcgaca acccaccgac actataaact gttctaactc     480

gtcttcacct ttcttttccc ccatgttgac taatgacttc acaatacaac tccatatata     540

accacacgtt accgtaaagg aggatgtata ctccagcatt gggagttggg tcaggacttg     600

tttcttaagt ccactgatat gggttcgggc caaaacaaat gtggcccgaa ccctatcaga     660

agaagaacca acaaggctcg gagcttgata aaaagttccg agtcttgttt ggttcaacct     720

gttttcatat agttgtgggt tgacaaccac tctatcaaaa acaggtggag atccgttttt     780

caagaatggc tgatcttcac ctgtttcaca aaccgaagcc cacgccttca ggaaaccgaa     840

ccgagtgttg gcgtcactga ggctatgatg atttgtcaag ccaatagaga tacccgagtt     900

cggaaaatac gtcacttgga ccgagaaaac cgggagtgtg acgtaatcgg attctttaac     960

ggcattacct aacggaggga caagcggata aaagttttca catttccgag gatgatttgc    1020

tgacagatcg ttgaaatcaa gagtagtttc tgcgaaagta agcgcgacgg aatcaccttc    1080

cacgtgtcgg atttcgggtt tcctagtgga atcatgaggg tttggatata caataagttt    1140

gccaacaaat gggaaatagt gttgaagtgt gattgataat gagtgtttaa ggtttggaat    1200

aacggtttcc gtgaaatggg atttggaata agggaagtgg tagaagtaaa gatgatggac    1260
```

gggtgggaag agtagccatg caatgtcgaa gaaagtgagt ggcaatgaac ggtggccgat 1320
ggtggacggt ggtggggata ttctagaatg ttctagaatt gttagattgg gaatgttgtc 1380
cat 1383

<210> SEQ ID NO 33
<211> LENGTH: 460
<212> TYPE: PRT
<213> ORGANISM: Dahlia

<400> SEQUENCE: 33

Met Asp Asn Ile Pro Asn Leu Thr Ile Leu Glu His Ser Arg Ile Ser
1 5 10 15

Pro Pro Pro Ser Thr Ile Gly His Arg Ser Leu Pro Leu Thr Phe Phe
20 25 30

Asp Ile Ala Trp Leu Leu Phe Pro Pro Val His His Leu Tyr Phe Tyr
35 40 45

His Phe Pro Tyr Ser Lys Ser His Phe Thr Glu Thr Val Ile Pro Asn
50 55 60

Leu Lys His Ser Leu Ser Ile Thr Leu Gln His Tyr Phe Pro Phe Val
65 70 75 80

Gly Lys Leu Ile Val Tyr Pro Asn Pro His Asp Ser Thr Arg Lys Pro
85 90 95

Glu Ile Arg His Val Glu Gly Asp Ser Val Ala Leu Thr Phe Ala Glu
100 105 110

Thr Thr Leu Asp Phe Asn Asp Leu Ser Ala Asn His Pro Arg Lys Cys
115 120 125

Glu Asn Phe Tyr Pro Leu Val Pro Pro Leu Gly Asn Ala Val Lys Glu
130 135 140

Ser Asp Tyr Val Thr Leu Pro Val Phe Ser Val Gln Val Thr Tyr Phe
145 150 155 160

Pro Asn Ser Gly Ile Ser Ile Gly Leu Thr Asn His His Ser Leu Ser
165 170 175

Asp Ala Asn Thr Arg Phe Gly Phe Leu Lys Ala Trp Ala Ser Val Cys
180 185 190

Glu Thr Gly Glu Asp Gln Pro Phe Leu Lys Asn Gly Ser Pro Pro Val
195 200 205

Phe Asp Arg Val Val Val Asn Pro Gln Leu Tyr Glu Asn Arg Leu Asn
210 215 220

Gln Thr Arg Leu Gly Thr Phe Tyr Gln Ala Pro Ser Leu Val Gly Ser
225 230 235 240

Ser Ser Asp Arg Val Arg Ala Thr Phe Val Leu Ala Arg Thr His Ile
245 250 255

Ser Gly Leu Lys Lys Gln Val Leu Thr Gln Leu Pro Met Leu Glu Tyr
260 265 270

Thr Ser Ser Phe Thr Val Thr Cys Gly Tyr Ile Trp Ser Cys Ile Val
275 280 285

Lys Ser Leu Val Asn Met Gly Glu Lys Lys Gly Glu Asp Glu Leu Glu
290 295 300

Gln Phe Ile Val Ser Val Gly Cys Arg Ser Arg Leu Asp Pro Pro Leu
305 310 315 320

Pro Glu Asn Tyr Phe Gly Asn Cys Ser Ala Pro Cys Ile Val Thr Ile
325 330 335

Lys Asn Gly Val Leu Lys Gly Glu Asn Gly Phe Val Met Ala Ala Lys
340 345 350

-continued

```
Leu Ile Gly Glu Gly Ile Ser Lys Met Val Asn Lys Lys Gly Gly Ile
        355                 360                 365

Leu Glu Asp Ala Asp Arg Trp Tyr Asp Gly Phe Lys Ile Pro Ala Arg
    370                 375                 380

Lys Met Gly Ile Ser Gly Thr Pro Lys Leu Asn Phe Tyr Asp Ile Asp
385                 390                 395                 400

Phe Gly Trp Gly Lys Ala Met Lys Tyr Glu Val Val Ser Ile Asp Tyr
                405                 410                 415

Ser Ala Ser Val Ser Leu Ser Ala Cys Lys Glu Ser Ala Gln Asp Phe
            420                 425                 430

Glu Ile Gly Val Cys Phe Pro Ser Met Gln Met Glu Ala Phe Gly Lys
        435                 440                 445

Ile Phe Asn Asp Gly Leu Glu Ser Ala Ile Ala Ser
    450                 455                 460
```

TRANSFORMED PLANT HAVING BLUE FLOWER COLOR, AND METHOD FOR CREATING SAME

CROSS REFERENCE TO RELATED APPLICATIONS

This application is the National Stage of International Application No. PCT/JP2018/036935, filed Oct. 2, 2018, and claims benefit of Japanese Patent Application No. 2017-193480 filed on Oct. 3, 2017.

REFERENCE TO A SEQUENCE LISTING

The instant application contains a sequence listing which has been submitted in ASCII format via EFS-Web and is hereby incorporated by reference in its entirety. Said ASCII copy, created on Oct. 1, 2018 is named P180461WO_Sequence_Listing.txt and is 87,886 bytes in size.

FIELD

The present invention relates to a method for creating a transformed plant having a blue-hued flower color, characterized in that delphinidin-type anthocyanin and a flavone C-glycoside are made to coexist within the plant cells, and a transformed plant characterized in that delphinidin-type anthocyanin and a flavone C-glycoside coexist within the plant cells, or its inbred or outbred progenies, or their propagules, partial plant bodies (especially cut flowers), processed forms (especially processed cut flowers), tissues or cells.

BACKGROUND

Roses, chrysanthemums and carnations are industrially important plants around the world. In particular, roses are the most popular flowering plant with records of their cultivation from before the Christian Era and artificial breeding has been carried out thereon over several hundred years. However, due to the problem that there are no wild species with a blue-hued flower color among related species that can be crossed, it has been difficult to create a rose variety with a blue-hued flower color by conventional cross breeding or mutation breeding. The creation of a completely new blue-hued flower color will stimulate a new demand for the flower as the areas of use thereof expands, leading to expansion of production and consumption. Therefore, attempts have been made to produce roses having a blue-hued flower color by genetic engineering techniques.

For example, purple to blue flowers are known to contain large amounts of delphinidin-type anthocyanins such as delphinidin, petunidin and malvidin. However, flowers such as roses cannot produce such delphinidin-type anthocyanins and so studies have been conducted in which delphinidin is artificially produced by expression of the flavonoid 3',5'-hydroxylase gene which is necessary for the synthesis thereof (NPL1). However, in order to express the enzyme gene for producing the target substance in a recombinant plant, even if the metabolism of the plant is artificially altered, competition with endogenous enzymes of the plant itself frequently occurs and in most cases accumulation of the target product does not occur at all or occurs to a limited extent.

Furthermore, in addition to the structure of the anthocyanin itself, the color of the flower changes depending on coexisting flavonoids (referred to as copigments), metal ions, the pH of the vacuole, etc. Flavones and flavonols are typical copigments which, by being stacked so as to sandwiched anthocyanin, have an effect of making the anthocyanin appear blue, and dark (NPL2). This is known as the copigment effect. Flavones in particular are known to exhibit a strong copigment effect. For example, it has been reported that analysis of genetically modified carnations found that flavones exhibited a significant copigment effect (NPL3). Further, it has been reported that in the Dutch Iris, the higher the ratio of total flavone content to total delphinidin content, the greater the copigment effect and the color becomes blue (NPL4).

However, not all plants are able to produce flavone, and roses, petunias, and the like do not accumulate flavone. Thus, attempts have been made to express, in such plants, genes encoding proteins that act to synthesize flavone from flavanone in order to modify the color of the flowers (PTL1).

Furthermore, in addition to the free form, flavone is also distributed as a glycoside, and although flavone O-glycoside and flavone C-glycoside are produced, it is known that flavone C-glycoside in particular exhibits a strong copigment effect. For example, it has been reported that isovitexin, which is a type of flavone C-glycoside, exhibits a copigment effect with anthocyanin in *Iris ensata* Thunb and by stabilizing anthocyanin, a blue flower color is also stabilized (NPL5). With regard to flavone C-glycoside, two biosynthetic pathways have thus far been reported. In one of the pathways, flavone C-glycoside is synthesized from flavanone by reactions catalyzed by flavanone 2-hydroxylase and C-glucosyltransferase, and dehydratase. In the other pathway, flavone C-glycoside is synthesized from flavanone by reactions catalyzed by flavone synthase and flavone C-glucosyltransferase (NPL6).

However, there have been no reports so far of examples of these genes being introduced into plants that do not produce flavone C-glycoside. Further, the copigment effect is considered to be influenced by the quantitative ratio of anthocyanin and flavone, modification by sugar or acyl groups on the anthocyanin and flavone, etc., and it is not always possible to make the flower color blue by merely expressing the flavone synthase gene and accumulating flavone. When the torenia flavone synthase gene is expressed in petunias, the bluish-purple color of the flower fades (NPL7). Further, when a *Gentiana scabra*-derived flavone synthase gene is expressed in tobacco, flavone was synthesized (NPL8) but the flower color still faded. Furthermore, there have been attempts to modify the flower color of roses by artificially incorporating flavone and malvidin (PTL2), but the creation of roses having a blue-hued flower color has been unsuccessful.

In fact, up until now, in flower color modification of roses aiming for a blue-hued flower color, roses with a purple color (RHS color chart hue group: Purple group) or a bluish-purple color (Purple-Violet group, Violet group) were the limits and roses with purplish-blue color (Violet-Blue group) or blue color (Blue group) flowers have not been created. Thus, there is still a need for the development of a blue color expression control technique to enable the creation of roses with a true, blue flower color.

CITATION LIST

Patent Literature

[PTL 1] Japanese Unexamined Patent Publication (Kokai) No. 2000-279182
[PTL 2] WO2008/156206

Non-Patent Literature

[NPL 1] Tanaka 2006 Phytochemistry Reviews 5, 283-291
[NPL 2] Goto (1987) Prog. Chem. Org. Natl. Prod. 52
[NPL 3] Fukui et al. Phytochemistry, 63, 15-23, 2003
[NPL 4] Mizuno et al. Plant Physiol. Bioch. 2013 72, 116-124
[NPL 5] Yabuya et al. Euphytica 2000 115, 1-5
[NPL 6] Sasaki et al. FEBS Lett. 2015 589, 182-187
[NPL 7] Tsuda et al. Plant Biotechnology, 21, 377-386, 2004
[NPL 8] Nakatuka et al. 2006, Molecular Breeding 17:91-99

SUMMARY

Technical Problem

The object of the present invention is to provide a transformed plant having a blue-hued flower color or its inbred or outbred progenies, or their propagules, partial plant bodies (especially cut flowers), processed forms (especially processed cut flowers), tissues or cells.

Solution to Problem

The present inventors carried out extensive research in order to solve the problem above and as a result of repeated experimentation, discovered that a transformed plant having a blue-hued flower color (RHS color chart $5^{th}$ edition: Violet-Blue group/Blue group and/or a hue angle of 339.7° to 270.0°) that could not be previously obtained could be created by making a delphinidin-type anthocyanin and a flavone C-glycoside coexist in the petal of plants such as roses, and thereby the present invention was completed.

Specifically, the present invention relates to the following:

[1] A method for creating a transformed plant characterized in that a delphinidin-type anthocyanin and a flavone C-glycoside are made to coexist in a cell of a plant.

[2] The method according to 1, wherein the flavone C-glycoside is selected from the group consisting of flavone 6-C-glucoside, flavone 8-C-glucoside, and a combination thereof.

[3] The method according to 2, wherein the flavone C-glycoside is apigenin 6-C-glucoside and/or luteolin 6-C-glucoside.

[4] The method according to any one of 1 to 3, wherein the delphinidin-type anthocyanin is selected from the group consisting of malvidin 3,5-diglucoside, delphinidin 3,5-diglucoside, petunidin 3,5-diglucoside, acylated anthocyanins (e.g., delphinidin 3-(6"-p-coumaroyl-β-glucosyl)-5-β-glucoside or delphinidin 3-(6"-p-malonyl-β-glucosyl)-3',5'-β-diglucoside), and combinations thereof.

[5] The method according to any one of 1 to 4 comprising transforming a host plant with a vector comprising a flavone synthase (FNS) gene or a homologue thereof and a flavone C-glucosyltransferase (CGT) gene or a homologue thereof.

[6] The method according to 5, wherein the vector further comprises a flavonoid 3',5'-hydroxylase (F3'5'H) gene or a homologue thereof and a methyltransferase (MT) gene or a homologue thereof.

[7] The method according to 6, wherein:

the FNS gene or homologue thereof is selected from the group consisting of (1-a) a polynucleotide consisting of the base sequence of SEQ ID NO: 19, (1-b) a polynucleotide hybridizing to a polynucleotide consisting of a base sequence complimentary to the base sequence of SEQ ID NO: 19 under stringent conditions and encoding a protein having the same activity as a protein encoded by the polynucleotide set forth in (1-a), (1-c) a polynucleotide encoding a protein consisting of the amino acid sequence of SEQ ID NO: 20, (1-d) a polynucleotide encoding a protein consisting of an amino acid sequence including deletion, substitution, insertion, and/or addition of one or more amino acids in the amino acid sequence of SEQ ID NO: 20 and having the same activity as a protein encoded by the polynucleotide set forth in (1-c), and (1-e) a polynucleotide encoding a protein having an amino acid sequence with at least 90% sequence identity to the amino acid sequence of SEQ ID NO: 20 and having the same activity as a protein encoded by the polynucleotide set forth in (1-c);

the CGT gene or homologue thereof is selected from the group consisting of (2-a) a polynucleotide consisting of the base sequence of SEQ ID NO: 21, (2-b) a polynucleotide hybridizing to a polynucleotide consisting of a base sequence complimentary to the base sequence of SEQ ID NO: 21 under stringent conditions and encoding a protein having the same activity as a protein encoded by the polynucleotide set forth in (2-a), (2-c) a polynucleotide encoding a protein consisting of the amino acid sequence of SEQ ID NO: 22, (2-d) a polynucleotide encoding a protein consisting of an amino acid sequence including deletion, substitution, insertion, and/or addition of one or more amino acids in the amino acid sequence of SEQ ID NO: 22 and having the same activity as a protein encoded by the polynucleotide set forth in (2-c), and (2-e) a polynucleotide encoding a protein having an amino acid sequence with at least 90% sequence identity to the amino acid sequence of SEQ ID NO: 22 and having the same activity as a protein encoded by the polynucleotide set forth in (2-c);

the F3'5'H gene or homologue thereof is selected from the group consisting of (3-a) a polynucleotide consisting of the base sequence of SEQ ID NO: 9, (3-b) a polynucleotide hybridizing to a polynucleotide consisting of a base sequence complimentary to the base sequence of SEQ ID NO: 9 under stringent conditions and encoding a protein having the same activity as a protein encoded by the polynucleotide set forth in (3-a), (3-c) a polynucleotide encoding a protein consisting of the amino acid sequence of SEQ ID NO: 10, (3-d) a polynucleotide encoding a protein consisting of an amino acid sequence including deletion, substitution, insertion, and/or addition of one or more amino acids in the amino acid sequence of SEQ ID NO: 10 and having the same activity as a protein encoded by the polynucleotide set forth in (3-c), and (3-e) a polynucleotide encoding a protein having an amino acid sequence with at least 90% sequence identity to the amino acid sequence of SEQ ID NO: 10 and having the same activity as a protein encoded by the polynucleotide set forth in (3-c);

the MT gene or homologue thereof is selected from the group consisting of (4-a) a polynucleotide consisting of the base sequence of SEQ ID NO: 17, (4-b) a polynucleotide hybridizing to a polynucleotide consisting of a base sequence complimentary to the base sequence of SEQ ID NO: 17 under stringent conditions and encoding a protein having the same activity as a protein encoded by the polynucleotide set forth in (4-a), (4-c) a polynucleotide encoding a protein consisting of the amino acid sequence of SEQ ID NO: 18, (4-d) a polynucleotide encoding a protein consisting of an amino acid sequence including deletion, substitution, insertion, and/or addition of one or more amino acids in the amino acid sequence of SEQ ID NO: 18 and having the same activity as a protein encoded by the polynucleotide set forth in (4-c), and (4-e) a polynucleotide encoding a protein having an amino acid sequence with at least 90% sequence identity to the amino acid sequence of SEQ ID NO: 18 and having the same activity as a protein encoded by the polynucleotide set forth in (4-c).

[8] The method according to 7, wherein the CGT gene or a homologue thereof has added thereto an *Arabidopsis* alcohol dehydrogenase (ADH) gene-derived 5' untranslated region (5'-UTR) (SEQ ID NO: 23).

[9] The method according to any one of 1 to 4 comprising transforming a host plant with a vector comprising a flavanone 2-hydroxylase (F2H) gene or a homologue thereof, a flavone C-glucosyltransferase (CGT) gene or a homologue thereof, and a dehydratase (FDH) gene or a homologue thereof.

[10] The method according to 9, wherein the vector further comprises a flavonoid 3',5'-hydroxylase (F3'S'H) gene or a homologue thereof, and a methyltransferase (MT) gene or a homologue thereof.

[11] The method according to 10, wherein:

the F2H gene or homologue thereof is selected from the group consisting of (5-a) a polynucleotide consisting of the base sequence of SEQ ID NO: 3, (5-b) a polynucleotide hybridizing to a polynucleotide consisting of a base sequence complimentary to the base sequence of SEQ ID NO: 3 under stringent conditions and encoding a protein having the same activity as a protein encoded by the polynucleotide set forth in (5-a), (5-c) a polynucleotide encoding a protein consisting of the amino acid sequence of SEQ ID NO: 4, (5-d) a polynucleotide encoding a protein consisting of an amino acid sequence including deletion, substitution, insertion, and/or addition of one or more amino acids in the amino acid sequence of SEQ ID NO: 4 and having the same activity as a protein encoded by the polynucleotide set forth in (5-c), and (5-e) a polynucleotide encoding a protein having an amino acid sequence with at least 90% sequence identity to the amino acid sequence of SEQ ID NO: 4 and having the same activity as a protein encoded by the polynucleotide set forth in (5-c);

the CGT gene or homologue thereof is selected from the group consisting of (6-a) a polynucleotide consisting of the base sequence of SEQ ID NO: 13, (6-b) a polynucleotide hybridizing to a polynucleotide consisting of a base sequence complimentary to the base sequence of SEQ ID NO: 13 under stringent conditions and encoding a protein having the same activity as a protein encoded by the polynucleotide set forth in (6-a), (6-c) a polynucleotide encoding a protein consisting of the amino acid sequence of SEQ ID NO: 14, (6-d) a polynucleotide encoding a protein consisting of an amino acid sequence including deletion, substitution, insertion, and/or addition of one or more amino acids in the amino acid sequence of SEQ ID NO: 14 and having the same activity as a protein encoded by the polynucleotide set forth in (6-c), and (6-e) a polynucleotide encoding a protein having an amino acid sequence with at least 90% sequence identity to the amino acid sequence of SEQ ID NO: 14 and having the same activity as a protein encoded by the polynucleotide set forth in (6-c);

the FDH gene or homologue thereof is selected from the group consisting of (7-a) a polynucleotide consisting of the base sequence of SEQ ID NO: 15, (7-b) a polynucleotide hybridizing to a polynucleotide consisting of a base sequence complimentary to the base sequence of SEQ ID NO: 15 under stringent conditions and encoding a protein having the same activity as a protein encoded by the polynucleotide set forth in (7-a), (7-c) a polynucleotide encoding a protein consisting of the amino acid sequence of SEQ ID NO: 16, (7-d) a polynucleotide encoding a protein consisting of an amino acid sequence including deletion, substitution, insertion, and/or addition of one or more amino acids in the amino acid sequence of SEQ ID NO: 16 and having the same activity as a protein encoded by the polynucleotide set forth in (7-c), and (7-e) a polynucleotide encoding a protein having an amino acid sequence with at least 90% sequence identity to the amino acid sequence of SEQ ID NO: 16 and having the same activity as a protein encoded by the polynucleotide set forth in (7-c);

the F3'5'H gene or homologue thereof is selected from the group consisting of (8-a) a polynucleotide consisting of the base sequence of SEQ ID NO: 9, (8-b) a polynucleotide hybridizing to a polynucleotide consisting of a base sequence complimentary to the base sequence of SEQ ID NO: 9 under stringent conditions and encoding a protein having the same activity as a protein encoded by the polynucleotide set forth in (8-a), (8-c) a polynucleotide encoding a protein consisting of the amino acid sequence of SEQ ID NO: 10, (8-d) a polynucleotide encoding a protein consisting of an amino acid sequence including deletion, substitution, insertion, and/or addition of one or more amino acids in the amino acid sequence of SEQ ID NO: 10 and having the same activity as a protein encoded the polynucleotide set forth in (8-c), and (8-e) a polynucleotide encoding a protein having an amino acid sequence with at least 90% sequence identity to the amino acid sequence of SEQ ID NO: 10 and the same activity as a protein encoded by the polynucleotide set forth in (8-c); and the MT gene or homologue thereof is selected from the group consisting of (9-a) a polynucleotide consisting of the base sequence of SEQ ID NO: 17, (9-b) a polynucleotide hybridizing to a polynucleotide consisting of a base sequence complimentary to the base sequence of SEQ ID NO: 17 under stringent conditions and encoding a protein having the same activity as a protein encoded by the polynucleotide set forth in (9-a), (9-c) a polynucleotide encoding a protein consisting of the amino acid sequence of SEQ ID NO: 18, (9-d) a polynucleotide encoding a protein consisting of an amino acid sequence including deletion, substitution, insertion, and/or addition of one or more amino acids in the amino acid sequence of SEQ ID NO: 18 and having the same activity as a protein encoded by the polynucleotide set forth in (9-c), and (9-e) a polynucleotide encoding a protein having an amino acid sequence with at least 90% sequence identity to the amino acid sequence of SEQ ID NO: 18 and having the same activity as a protein encoded by the polynucleotide set forth in (9-c).

[12] A transformed plant or an inbred or outbred progeny thereof characterized in that delphinidin-type anthocyanin and flavone C-glycoside coexist within a cell thereof.

[13] The transformed plant or inbred or outbred progeny thereof according to 12, wherein the flavone C-glycoside is selected from the group consisting of flavone 6-C-glucoside, flavone 8-C glucoside and a combination thereof.

[14] The transformed plant or inbred or outbred progeny thereof according to 13, wherein the flavone C-glycoside is apigenin 6-C-glucoside.

[15] The transformed plant or inbred or outbred progeny thereof according to any one of 12 to 14, wherein the delphinidin-type anthocyanin is selected from the group consisting of malvidin 3,5-diglucoside, delphinidin 3,5-diglucoside, petunidin 3,5-diglucoside, and acylated anthocyanins (for example, delphinidin 3-(6"-p-coumaroyl-β-glucosyl)-5-β-glucoside or delphinidin 3-(6-p-malonyl-β-glucosyl)-3',5'-β-diglucoside) and combinations thereof.

[16] The transformed plant or inbred or outbred progeny thereof according to any one of 12 to 15 comprising a flavone synthase (FNS) gene or a homologue thereof, and a flavone C-glucosyltransferase (CGT) gene or a homologue thereof.

[17] The transformed plant or inbred or outbred progeny thereof according to 16 further comprising a flavonoid 3',5'-hydroxylase (F3'5'H) gene or a homologue thereof and a methyltransferase (MT) gene or a homologue thereof.

[18] The transformed plant or inbred or outbred progeny thereof according to 17, wherein: the FNS gene or homologue thereof is selected from the group consisting of (1-a) a polynucleotide consisting of the base sequence of SEQ ID NO: 19, (1-b) a polynucleotide hybridizing to a polynucleotide consisting of a base sequence complimentary to the base sequence of SEQ ID NO: 19 under stringent conditions and encoding a protein having the same activity as a protein encoded by the polynucleotide set forth in (1-a), (1-c) a polynucleotide encoding a protein consisting of the amino acid sequence of SEQ ID NO: 20, (1-d) a polynucleotide encoding a protein consisting of an amino acid sequence including deletion, substitution, insertion, and/or addition of one or more amino acids in the amino acid sequence of SEQ ID NO: 20 and having the same activity as a protein encoded by the polynucleotide set forth in (1-c), and (1-e) a polynucleotide encoding a protein having an amino acid sequence with at least 90% sequence identity to the amino acid sequence of SEQ ID NO: 20 and having the same activity as a protein encoded by the polynucleotide set forth in (1-c);

the CGT gene or homologue thereof is selected from the group consisting of (2-a) a polynucleotide consisting of the base sequence of SEQ ID NO: 21, (2-b) a polynucleotide hybridizing to a polynucleotide consisting of a base sequence complimentary to the base sequence of SEQ ID NO: 21 under stringent conditions and encoding a protein having the same activity as a protein encoded by the polynucleotide set forth in (2-a), (2-c) a polynucleotide encoding a protein consisting of the amino acid sequence of SEQ ID NO: 22, (2-d) a polynucleotide encoding a protein consisting of an amino acid sequence including deletion, substitution, insertion, and/or addition of one or more amino acids in the amino acid sequence of SEQ ID NO: 22 and having the same activity as a protein encoded by the polynucleotide set forth in (2-c), and (2-e) a polynucleotide encoding a protein having an amino acid sequence with at least 90% sequence identity to the amino acid sequence of SEQ ID NO: 22 and having the same activity as a protein encoded by the polynucleotide set forth in (2-c);

the F3'S'H gene or homologue thereof is selected from the group consisting of (3-a) a polynucleotide consisting of the base sequence of SEQ ID NO: 9, (3-b) a polynucleotide hybridizing to a polynucleotide consisting of a base sequence complimentary to the base sequence of SEQ ID NO: 9 under stringent conditions and encoding a protein having the same activity as a protein encoded by the polynucleotide set forth in (3-a), (3-c) a polynucleotide encoding a protein consisting of the amino acid sequence of SEQ ID NO: 10, (3-d) a polynucleotide encoding a protein consisting of an amino acid sequence including deletion, substitution, insertion, and/or addition of one or more amino acids in the amino acid sequence of SEQ ID NO: 10 and having the same activity as a protein encoded by the polynucleotide set forth in (3-c), and (3-e) a polynucleotide encoding a protein having an amino acid sequence with at least 90% sequence identity to the amino acid sequence of SEQ ID NO: 10 and having the same activity as a protein encoded by the polynucleotide set forth in (3-c); and the MT gene or homologue thereof is selected from the group consisting of (4-a) a polynucleotide consisting of the base sequence of SEQ ID NO: 17, (4-b) a polynucleotide hybridizing to a polynucleotide consisting of a base sequence complimentary to the base sequence of SEQ ID NO: 17 under stringent conditions and encoding a protein having the same activity as a protein encoded by the polynucleotide set forth in (4-a), (4-c) a polynucleotide encoding a protein consisting of the amino acid sequence of SEQ ID NO: 18, (4-d) a polynucleotide encoding a protein consisting of an amino acid sequence including deletion, substitution, insertion, and/or addition of one or more amino acids in the amino acid sequence of SEQ ID NO: 18 and having the same activity as a protein encoded by the polynucleotide set forth in (4-c), and (4-e) a polynucleotide encoding a protein having an amino acid sequence with at least 90% sequence identity to the amino acid sequence of SEQ ID NO: 18 and having the same activity as a protein encoded by the polynucleotide set forth in (4-c).

[19] The transformed plant or inbred or outbred progeny thereof according to 18, wherein the CGT gene or a homologue thereof has added thereto an *Arabidopsis* alcohol dehydrogenase (ADH) gene-derived 5' untranslated region (5'-UTR) (SEQ ID NO: 23).

[20] The transformed plant or inbred or outbred progeny thereof according to any one of 12 to 15 comprising a flavanone 2-hydroxylase (F2H) gene or a homologue thereof, a flavone C-glucosyltransferase (CGT) gene or a homologue thereof, and a dehydratase (FDH) gene or a homologue thereof.

[21] The transformed plant or inbred or outbred progeny thereof according to 20 further comprising a flavonoid 3',5'-hydroxylase (F3'S'H) gene or a homologue thereof, and a methyltransferase (MT) gene or a homologue thereof.

[22] The transformed plant or inbred or outbred progeny thereof according to 21, wherein: the F2H gene or homologue thereof is selected from the group consisting of (5-a) a polynucleotide consisting of the base sequence of SEQ ID NO: 3, (5-b) a polynucleotide hybridizing to a polynucleotide consisting of a base sequence complimentary to the base sequence of SEQ ID NO: 3 under stringent conditions and encoding a protein having the same activity as a protein encoded by the polynucleotide set forth in (5-a), (5-c) a polynucleotide encoding a protein consisting of the amino acid sequence of SEQ ID NO: 4, (5-d) a polynucleotide encoding a protein consisting of an amino acid sequence including deletion, substitution, insertion, and/or addition of one or more amino acids in the amino acid sequence of SEQ ID NO: 4 and having the same activity as a protein encoded by the polynucleotide set forth in (5-c), and (5-e) a polynucleotide encoding a protein having an amino acid sequence with at least 90% sequence identity to the amino acid sequence of SEQ ID NO: 4 and having the same activity as a protein encoded by the polynucleotide set forth in (5-c);

the CGT gene or homologue thereof is selected from the group consisting of (6-a) a polynucleotide consisting of the base sequence of SEQ ID NO: 13, (6-b) a polynucleotide hybridizing to a polynucleotide consisting of a base sequence complimentary to the base sequence of SEQ ID NO: 13 under stringent conditions and encoding a protein having the same activity as a protein encoded by the polynucleotide set forth in (6-a), (6-c) a polynucleotide encoding a protein consisting of the amino acid sequence of SEQ ID NO: 14, (6-d) a polynucleotide encoding a protein consisting of an amino acid sequence including deletion, substitution, insertion, and/or addition of one or more amino acids in the amino acid sequence of SEQ ID NO: 14 and having the same activity as a protein encoded by the polynucleotide set forth in (6-c), and (6-e) a polynucleotide encoding a protein having an amino acid sequence with at least 90% sequence identity to the amino acid sequence of SEQ ID NO: 14 and having the same activity as a protein encoded by the polynucleotide set forth in (6-c);

the FDH gene or homologue thereof is selected from the group consisting of (7-a) a polynucleotide consisting of the base sequence of SEQ ID NO: 15, (7-b) a polynucleotide hybridizing to a polynucleotide consisting of a base sequence complimentary to the base sequence of SEQ ID NO: 15 under stringent conditions and encoding a protein having the same activity as a protein encoded by the polynucleotide set forth in (7-a), (7-c) a polynucleotide encoding a protein consisting of the amino acid sequence of SEQ ID NO: 16, (7-d) a polynucleotide encoding a protein consisting of an amino acid sequence including deletion, substitution, insertion, and/or addition of one or more amino acids in the amino acid sequence of SEQ ID NO: 16 and having the same activity as a protein encoded by the polynucleotide set forth in (7-c), and (7-e) a polynucleotide encoding a protein having an amino acid sequence with at least 90% sequence identity to the amino acid sequence of SEQ ID NO: 16 and having the same activity as a protein encoded by the polynucleotide set forth in (7-c);

the F3'5'H gene or homologue thereof is selected from the group consisting of (8-a) a polynucleotide consisting of the base sequence of SEQ ID NO: 9, (8-b) a polynucleotide hybridizing to a polynucleotide consisting of a base sequence complimentary to the base sequence of SEQ ID NO: 9 under stringent conditions and encoding a protein having the same activity as a protein encoded by the polynucleotide set forth in (8-a), (8-c) a polynucleotide encoding a protein consisting of the amino acid sequence of SEQ ID NO: 10, (8-d) a polynucleotide encoding a protein consisting of an amino acid sequence including deletion, substitution, insertion, and/or addition of one or more amino acids in the amino acid sequence of SEQ ID NO: 10 and having the same activity as a protein encoded by the polynucleotide set forth in (8-c), and (8-e) a polynucleotide encoding a protein having an amino acid sequence with at least 90% sequence identity to the amino acid sequence of SEQ ID NO: 10 and the same activity as a protein encoded by the polynucleotide set forth in (8-c); and the MT gene or homologue thereof is selected from the group consisting of (9-a) a polynucleotide consisting of the base sequence of SEQ ID NO: 17, (9-b) a polynucleotide hybridizing to a polynucleotide consisting of a base sequence complimentary to the base sequence of SEQ ID NO: 17 under stringent conditions and encoding a protein having the same activity as a protein encoded by the polynucleotide set forth in (9-a), (9-c) a polynucleotide encoding a protein consisting of the amino acid sequence of SEQ ID NO: 18, (9-d) a polynucleotide encoding a protein consisting of an amino acid sequence including deletion, substitution, insertion, and/or addition of one or more amino acids in the amino acid sequence of SEQ ID NO: 18 and having the same activity as a protein encoded by the polynucleotide set forth in (9-c), and (9-e) a polynucleotide encoding a protein having an amino acid sequence with at least 90% sequence identity to the amino acid sequence of SEQ ID NO: 18 and having the same activity as a protein encoded by the polynucleotide set forth in (9-c).

[23] The transformed plant or inbred or outbred progeny thereof according to any one of 12 to 22 having a flower color in the Blue group or Violet-Blue group of the RHS color chart and/or a hue angle of 339.7° to 270° in the CIE L*a*b* color system.

[24] A propagule, part of a plant, tissue or cell of the transformed plant or inbred or outbred progeny thereof according to any one of 12 to 23.

[25] A cut flower of the transformed plant or inbred or outbred progeny thereof according to any one of 12 to 23, or a processed product created from the cut flower.

[26] A vector comprising a flavone synthase (FNS) gene or a homologue thereof and a flavone C-glucosyltransferase (CGT) gene or a homologue thereof.

[27] The vector according to 26 further comprising a flavonoid 3',5'-hydroxylase (F3'5'H) gene or a homologue thereof, and a methyltransferase (MT) gene or a homologue thereof.

[28] The vector according to 27, wherein:

the FNS gene or homologue thereof is selected from the group consisting of (1-a) a polynucleotide consisting of the base sequence of SEQ ID NO: 19, (1-b) a polynucleotide hybridizing to a polynucleotide consisting of a base sequence complimentary to the base sequence of SEQ ID NO:19 under stringent conditions and encoding a protein having the same activity as a protein encoded by the polynucleotide set forth in (1-a), (1-c) a polynucleotide encoding a protein consisting of the amino acid sequence of SEQ ID NO: 20, (1-d) a polynucleotide encoding a protein consisting of an amino acid sequence including deletion, substitution, insertion, and/or addition of one or more amino acids in the amino acid sequence of SEQ ID NO: 20 and having the same activity as a protein encoded by the polynucleotide set forth in (1-c), and (1-e) a polynucleotide encoding a protein having an amino acid sequence with at least 90% sequence identity to the amino acid sequence of SEQ ID NO: 20 and the same activity as a protein encoded by the polynucleotide set forth in (1-c);

the CGT gene or homologue thereof is selected from the group consisting of (2-a) a polynucleotide consisting of the base sequence of SEQ ID NO: 21, (2-b) a polynucleotide hybridizing to a polynucleotide consisting of a base sequence complimentary to the base sequence of SEQ ID NO:21 under stringent conditions and encoding a protein having the same activity as a protein encoded by the polynucleotide set forth in (2-a), (2-c) a polynucleotide encoding a protein consisting of the amino acid sequence of SEQ ID NO: 22, (2-d) a polynucleotide encoding a protein consisting of an amino acid sequence including deletion, substitution, insertion, and/or addition of one or more amino acids in the amino acid sequence of SEQ ID NO: 22 and having the same activity as a protein encoded by the polynucleotide set forth in (2-c), and (2-e) a polynucleotide encoding a protein having an amino acid sequence with at least 90% sequence identity to the amino acid sequence of SEQ ID NO: 22 and having the same activity as a protein encoded by the polynucleotide set forth in (2-c);

the F3'5' gene or homologue thereof is selected from the group consisting of (3-a) a polynucleotide consisting of the base sequence of SEQ ID NO: 9, (3-b) a polynucleotide hybridizing to a polynucleotide consisting of a base sequence complimentary to the base sequence of SEQ ID NO: 9 under stringent conditions and encoding a protein having the same activity as a protein encoded by the polynucleotide set forth in (3-a), (3-c) a polynucleotide encoding a protein consisting of the amino acid sequence of SEQ ID NO: 10, (3-d) a polynucleotide encoding a protein consisting of an amino acid sequence including deletion, substitution, insertion, and/or addition of one or more amino acids in the amino acid sequence of SEQ ID NO: 10 and having the same activity as a protein encoded by the polynucleotide set forth in (3-c), and (3-e) a polynucleotide encoding a protein having an amino acid sequence with at least 90% sequence identity to the amino acid sequence of SEQ ID NO: 10 and having the same activity as a protein encoded by the polynucleotide set forth in (3-c);

the MT gene or homologue thereof is selected from the group consisting of (4-a) a polynucleotide consisting of the base sequence of SEQ ID NO: 17, (4-b) a polynucleotide hybridizing to a polynucleotide consisting of a base sequence complimentary to the base sequence of SEQ ID NO: 17 under stringent conditions and encoding a protein having the same activity as a protein encoded by the polynucleotide set forth in (4-a), (4-c) a polynucleotide encoding a protein consisting of the amino acid sequence of SEQ ID NO: 18, (4-d) a polynucleotide encoding a protein consisting of an amino acid sequence including deletion, substitution, insertion, and/or addition of one or more amino acids in the amino acid sequence of SEQ ID NO: 18 and having the same activity as a protein encoded by the polynucleotide set forth in (4-c), and (4-e) a polynucleotide encoding a protein having an amino acid sequence with at least 90% sequence identity to the amino acid sequence of SEQ ID NO: 18 and having the same activity as a protein encoded by the polynucleotide set forth in (4-c).

[29] The vector according to 28, wherein the CGT gene or a homologue thereof has added thereto an *Arabidopsis* alcohol dehydrogenase (ADH) gene-derived 5' untranslated region (5'-UTR) (SEQ ID NO: 23).

[30] A vector comprising a flavanone 2-hydroxylase (F2H) gene or a homologue thereof, a flavone C-glycoside (CGT) gene or a homologue thereof, and a dehydratase (FDH) gene or a homologue thereof.

[31] The vector according to 30 further comprising a flavonoid 3',5'-hydroxylase (F3'S'H) gene or a homologue thereof, and a methyltransferase (MT) gene or a homologue thereof.

[32] The vector according to 31, wherein:

the F2H gene or homologue thereof is selected from the group consisting of (5-a) a polynucleotide consisting of the base sequence of SEQ ID NO: 3, (5-b) a polynucleotide hybridizing to a polynucleotide consisting of a base sequence complimentary to the base sequence of SEQ ID NO: 3 under stringent conditions and encoding a protein having the same activity as a protein encoded by the polynucleotide set forth in (5-a), (5-c) a polynucleotide encoding a protein consisting of the amino acid sequence of SEQ ID NO: 4, (5-d) a polynucleotide encoding a protein consisting of an amino acid sequence including deletion, substitution, insertion, and/or addition of one or more amino acids in the amino acid sequence of SEQ ID NO: 4 and having the same activity as a protein encoded by the polynucleotide set forth in (5-c), and (5-e) a polynucleotide encoding a protein having an amino acid sequence with at least 90% sequence identity to the amino acid sequence of SEQ ID NO: 4 and the same activity as a protein encoded by the polynucleotide set forth in (5-c);

the CGT gene or homologue thereof is selected from the group consisting of (6-a) a polynucleotide consisting of the base sequence of SEQ ID NO: 13, (6-b) a polynucleotide hybridizing to a polynucleotide consisting of a base sequence complimentary to the base sequence of SEQ ID NO: 13 under stringent conditions and encoding a protein having the same activity as a protein encoded by the polynucleotide set forth in (6-a), (6-c) a polynucleotide encoding a protein consisting of the amino acid sequence of SEQ ID NO: 14, (6-d) a polynucleotide encoding a protein consisting of an amino acid sequence including deletion, substitution, insertion, and/or addition of one or more amino acids in the amino acid sequence of SEQ ID NO: 14 and having the same activity as a protein encoded the polynucleotide set forth in (6-c), and (6-e) a polynucleotide encoding a protein having an amino acid sequence with at least 90% sequence identity to the amino acid sequence of SEQ ID NO: 14 and having the same activity as a protein encoded by the polynucleotide set forth in (6-c);

the FDH gene or homologue thereof is selected from the group consisting of (7-a) a polynucleotide consisting of the base sequence of SEQ ID NO: 15, (7-b) a polynucleotide hybridizing to a polynucleotide consisting of a base sequence complimentary to the base sequence of SEQ ID NO: 15 under stringent conditions and encoding a protein having the same activity as a protein encoded by the polynucleotide set forth in (7-a), (7-c) a polynucleotide encoding a protein consisting of the amino acid sequence of SEQ ID NO: 16, (7-d) a polynucleotide encoding a protein consisting of an amino acid sequence including deletion, substitution, insertion, and/or addition of one or more amino acids in the amino acid sequence of SEQ ID NO: 16 and having the same activity as a protein encoded by the polynucleotide set forth in (7-c), and (7-e) a polynucleotide encoding a protein having an amino acid sequence with at least 90% sequence identity to the amino acid sequence of SEQ ID NO: 16 and having the same activity as a protein encoded by the polynucleotide set forth in (7-c);

the F3'5'H gene or homologue thereof is selected from the group consisting of (8-a) a polynucleotide consisting of the base sequence of SEQ ID NO: 9, (8-b) a polynucleotide hybridizing to a polynucleotide consisting of a base sequence complimentary to the base sequence of SEQ ID NO: 9 under stringent conditions and encoding a protein having the same activity as a protein encoded by the polynucleotide set forth in (8-a), (8-c) a polynucleotide encoding a protein consisting of the amino acid sequence of SEQ ID NO: 10, (8-d) a polynucleotide encoding a protein consisting of an amino acid sequence including deletion, substitution, insertion, and/or addition of one or more amino acids in the amino acid sequence of SEQ ID NO: 10 and having the same activity as a protein encoded by the polynucleotide set forth in (8-c), and (8-e) a polynucleotide encoding a protein having an amino acid sequence with at least 90% sequence identity to the amino acid sequence of SEQ ID NO: 10 and having the same activity as a protein encoded by the polynucleotide set forth in (8-c); and the MT gene or homologue thereof is selected from the group consisting of (9-a) a polynucleotide consisting of the base sequence of SEQ ID NO: 17, (9-b) a polynucleotide hybridizing to a polynucleotide consisting of a base sequence complimentary to the base sequence of SEQ ID NO: 17 under stringent conditions and encoding a protein having the same activity as a protein encoded by the polynucleotide set forth in (9-a), (9-c) a polynucleotide encoding a protein consisting of the amino acid sequence of SEQ ID NO: 18, (9-d) a polynucleotide encoding a protein consisting of an amino acid sequence including deletion, substitution, insertion, and/or addition of one or more amino acids in the amino acid sequence of SEQ ID NO: 18 and having the same activity as a protein encoded by the polynucleotide set forth in (9-c), and (9-e) a polynucleotide encoding a protein having an amino acid sequence with at least 90% sequence identity to the amino acid sequence of SEQ ID NO: 18 and having the same activity as a protein encoded by the polynucleotide set forth in (9-c).

[33] An isolated polynucleotide selected from the group consisting of:

(6-a) a polynucleotide consisting of the base sequence of SEQ ID NO: 13;

(6-b) a polynucleotide hybridizing to a polynucleotide consisting of a base sequence complimentary to the base sequence of SEQ ID NO: 13 under stringent conditions and encoding a protein having the same activity as a protein encoded by the polynucleotide set forth in (6-a);

(6-c) a polynucleotide encoding a protein consisting of the amino acid sequence of SEQ ID NO: 14;

(6-d) a polynucleotide encoding a protein consisting of an amino acid sequence including deletion, substitution, insertion, and/or addition of one or more amino acids in the amino acid sequence of SEQ ID NO: 14 and having the same activity as a protein encoded by the polynucleotide set forth in (6-c), and (6-e) a polynucleotide encoding a protein having an amino acid sequence with at least 90% sequence identity to the amino acid sequence of SEQ ID NO: 14 and the same activity as a protein encoded by the polynucleotide set forth in (6-c).

Advantageous Effects of Invention

According to the present invention, a plant variety having a blue-hued flower color (RHS color chart 5$^{th}$ edition: Violet-Blue group/Blue group and/or a hue angle of 339.7° to 270.0°) that could not be previously obtained could be created.

The present invention is a method for creating a transformed plant having a blue-hued flower color and relates to a method characterized in that delphinidin-type anthocyanin and flavone C-glycoside are made to coexist within the plant cells.

Anthocyanins are a group of pigments that exist widely in plants which are known to exhibit red, blue, and purple flower colors. Depending on the number of hydroxyl groups in the B-ring of the anthocyanidin site, which is an aglycone, the anthocyanidins are classified into the three groups pelargonidin, cyanidin, and delphinidin. The chromophore is the aglycone moiety and pelargonidin-based anthocyanins exhibit a bright red color, cyanidin-based anthocyanins exhibit a purple-red color, and delphinidin-based anthocyanins exhibit a purple-red color. Herein, for example, "delphinidin-based anthocyanin" can refer to delphinidin, malvidin, petunidin, or derivatives thereof, but is preferably malvidin.

Delphinidin-type anthocyanins, when made to coexist with substances such as flavones, flavanols, organic esters and tannins, may develop a bluish color due to intermolecular interactions therewith. This phenomenon is called copigmentation and substances that induce such phenomena are called copigments. Copigmentation not only has the effect of deepening color to induce the appearance of a blue color but also has the effect of darkening colors and improving color stability. The present inventors, at this time, confirmed that rose petals developed a blue color due to the effect of copigmentation of delphinidin-type anthocyanin and flavone C-glycoside.

Figure 1:
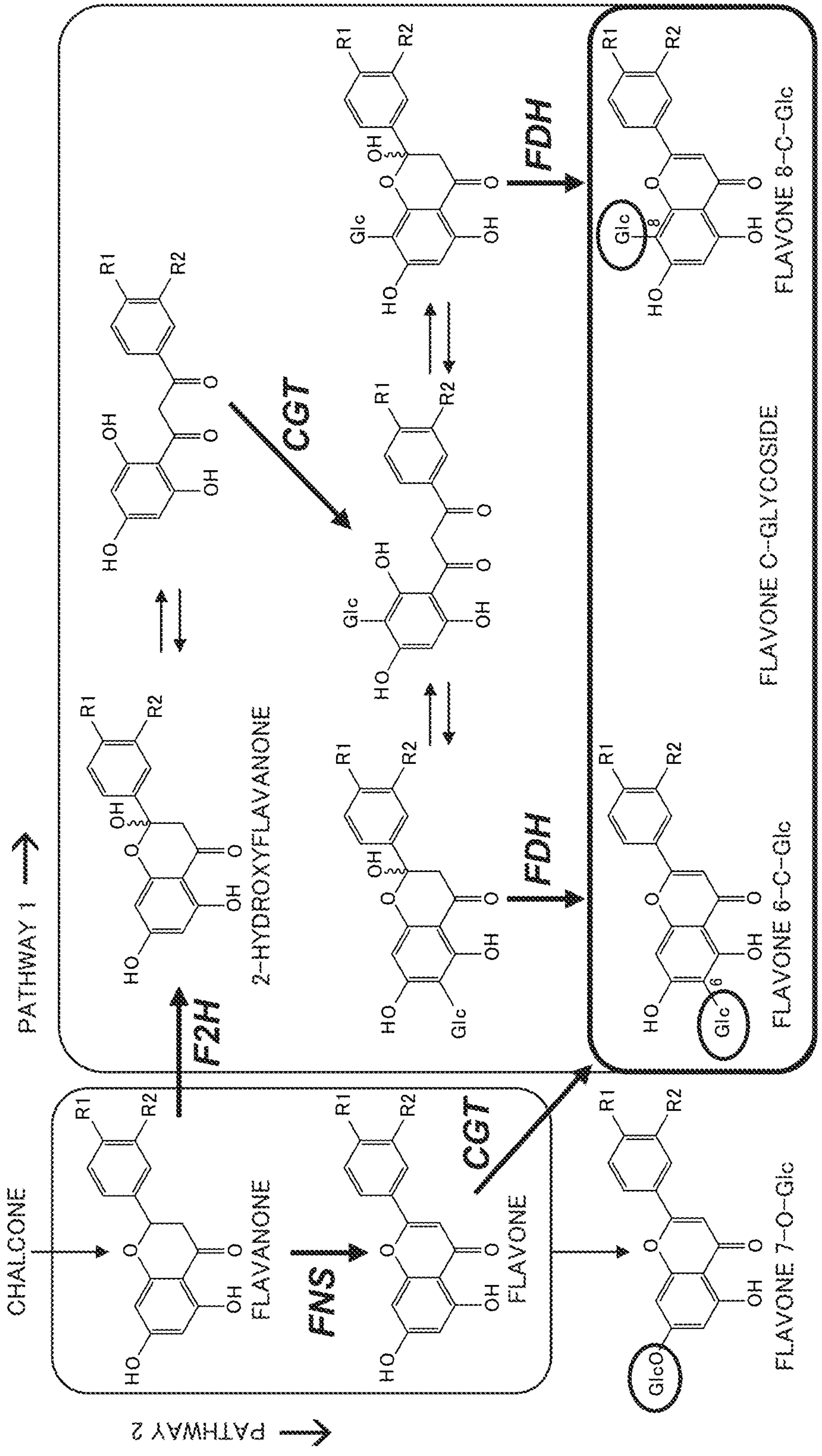
FIG. 1 illustrates the biosynthetic pathways of flavone C-glycoside in plants.
Figure 2:
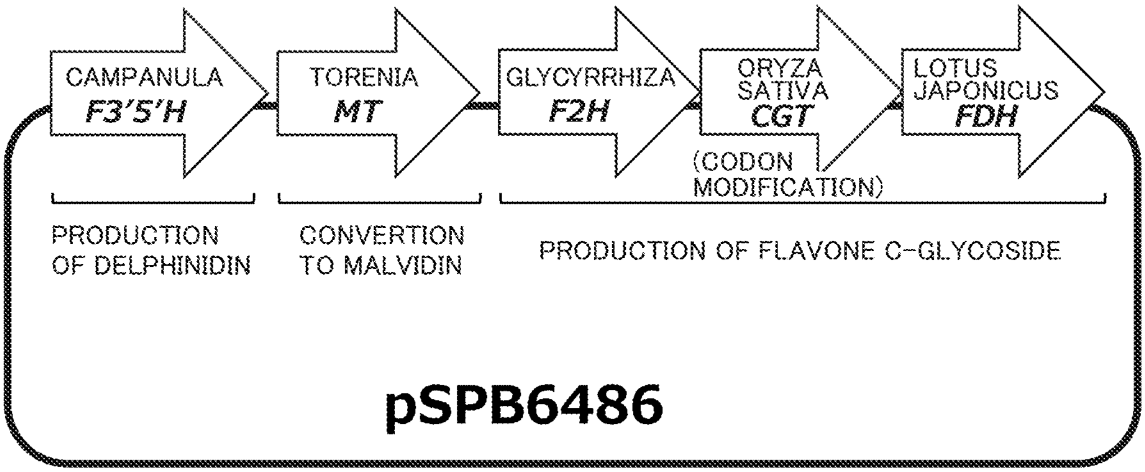
FIG. 2 illustrates the structure of pSPB6486.
Figure 3:
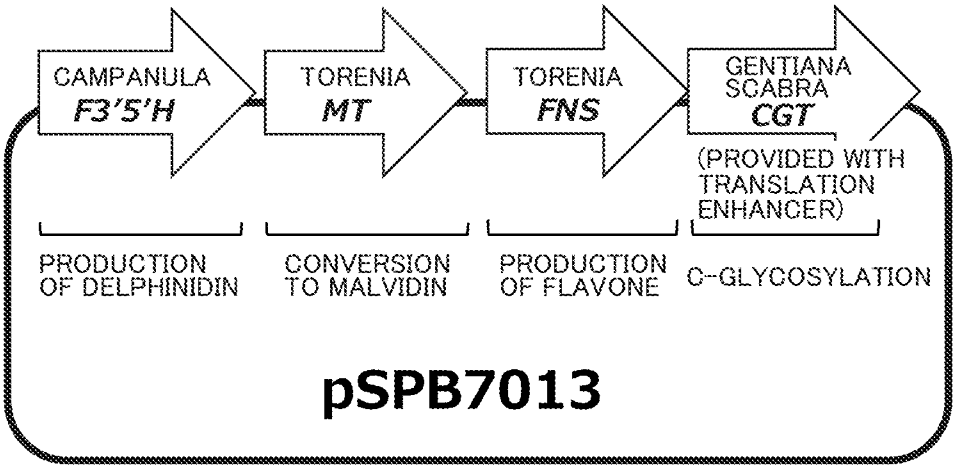
FIG. 3 illustrates the structure of pSPB7013

Flavone, which is a type of organic compound, is a cyclic ketone of a flavan derivative that exists in plants mainly as a glycoside. Flavone in a narrow sense is 2,3-didehydroflavan-4-one and is a compound with the chemical formula $C_{15}H_{10}O_2$ and a molecular weight of 222.24. However, flavone in the broader sense (flavone group) is just one category of flavonoids and flavonoids that have a flavone structure as the basic skeleton and do not have a hydroxyl group at position 3 are categorized as 'flavones'. Herein 'flavone C-glycoside' refers to flavones in the broad sense of the term, and from among glycosides of flavone derivatives, specifically refers to glycosides with aglycone bonded directly to the anomeric carbon of aldose. Examples of flavone C-glycoside include luteolin C-glycoside, tricetin C-glycoside, apigenin C-glycoside, and acacetin C-glycoside, but are not limited thereto. The flavone C-glycoside also include glycosides of apigenin, luteolin, tricetin, and acacetin derivatives. Two biosynthetic pathways of flavone C-glycoside are known in plants (FIG. 1). In pathway 1, flavone 6-C-glucoside and flavone 8-C-glucoside are produced through the action of flavanone 2-hydroxylase (F2H), a flavone C-glucosyltransferase (CGT), and a dehydratase (FDH). In pathway 2, flavone 6-C-glucoside is produced through the action of flavone synthase (FNS) and a flavone C-glucosyltransferase (CGT). It is preferable for the flavone C-glycoside to be selected from the group consisting of flavone 6-C-glucosides, flavone 8-C-glucosides, and combinations thereof. Examples thereof include apigenin 6-C-glucoside (isovitexin), apigenin 8-C-glucoside (vitexin), luteolin 6-C-glucoside (isoorientin), luteolin 8-C-glucoside (orientin), and derivatives thereof.

Accumulation of flavone C-glycoside within plant cells can be achieved by transforming a host plant with a vector containing genes that are essential for pathway 1 (namely, a flavanone 2-hydroxylase (F2H) gene, flavone C-glucosyltransferase (CGT) gene, and a dehydratase (FDH) gene) or a homologues thereof, or a vector containing genes that are essential for pathway 2 (namely, a flavone synthase (FNS) gene and a flavone C-glucosyltransferase (CGT) gene) or homologues thereof.

The source of the F2H gene, which is an essential gene in pathway 1, or a homologue thereof, is not particularly limited provided the desired function is exhibited, but is preferably a *Glycyrrhiza*-derived F2H gene or a homologue thereof comprising a polynucleotide selected from the following group consisting of:

(a) a polynucleotide consisting of the base sequence of SEQ ID NO: 3;

(b) a polynucleotide hybridizing to a polynucleotide consisting of a base sequence complimentary to the base sequence of SEQ ID NO: 3 under stringent conditions and encoding a protein having the same activity as a protein encoded by the polynucleotide set forth in (a);

(c) a polynucleotide encoding a protein consisting of the amino acid sequence of SEQ ID NO: 4;

(d) a polynucleotide encoding a protein consisting of an amino acid sequence including deletion, substitution, insertion, and/or addition of one or more amino acids in the amino acid sequence of SEQ ID NO: 4 and having the same activity as a protein encoded by the polynucleotide set forth in (c); and (e) a polynucleotide encoding a protein having an amino acid sequence with at least 90% sequence identity to the amino acid sequence of SEQ ID NO: 4 and the same activity as a protein encoded by the polynucleotide set forth in (c).

The source of the CGT gene, which is an essential gene in pathway 1, or a homologue thereof, is not particularly limited provided the desired function is exhibited, but is preferably an *Oryza sativa*-derived codon-usage modified CGT gene or a homologue thereof comprising a polynucleotide selected from the following group consisting of:

(a) a polynucleotide consisting of the base sequence of SEQ ID NO: 13;

(b) a polynucleotide hybridizing to a polynucleotide consisting of a base sequence complimentary to the base sequence of SEQ ID NO: 13 under stringent conditions and encoding a protein having the same activity as a protein encoded by the polynucleotide set forth in (a);

(c) a polynucleotide encoding a protein consisting of the amino acid sequence of SEQ ID NO: 14;

(d) a polynucleotide encoding a protein consisting of an amino acid sequence including deletion, substitution, insertion, and/or addition of one or more amino acids in the amino acid sequence of SEQ ID NO: 14 and having the same activity as a protein encoded by the polynucleotide set forth in (c); and (e) a polynucleotide encoding a protein having an amino acid sequence with at least 90% sequence identity to the amino acid sequence of SEQ ID NO: 14 and having the same activity as a protein encoded by the polynucleotide set forth in (c).

The source of the FDH gene, which is an essential gene in pathway 1, or a homologue thereof, is not particularly limited provided the desired function is exhibited, but is preferably a *Lotus japonicus*-derived FDH gene or a homologue thereof comprising a polynucleotide selected from the following group consisting of:

(a) a polynucleotide consisting of the base sequence of SEQ ID NO: 15;

(b) a polynucleotide hybridizing to a polynucleotide consisting of a base sequence complimentary to the base sequence of SEQ ID NO: 15 under stringent conditions and encoding a protein having the same activity as a protein encoded by the polynucleotide set forth in (a);

(c) a polynucleotide encoding a protein consisting of the amino acid sequence of SEQ ID NO: 16;

(d) a polynucleotide encoding a protein consisting of an amino acid sequence including deletion, substitution, insertion, and/or addition of one or more amino acids in the amino acid sequence of SEQ ID NO: 16 and having the same activity as a protein encoded by the polynucleotide set forth in (c); and (e) a polynucleotide encoding a protein having an amino acid sequence with at least 90% sequence identity to the amino acid sequence of SEQ ID NO: 16 and having the same activity as a protein encoded by the polynucleotide set forth in (c).

The source of the FNS gene, which is an essential gene in pathway 2, or a homologue thereof, is not particularly limited provided the desired function is exhibited, but is preferably a *Torenia*-derived FNS gene or a homologue thereof comprising a polynucleotide selected from the following group consisting of:

(a) a polynucleotide consisting of the base sequence of SEQ ID NO: 19;

(b) a polynucleotide hybridizing to a polynucleotide consisting of a base sequence complimentary to the base sequence of SEQ ID NO: 19 under stringent conditions and encoding a protein having the same activity as a protein encoded by the polynucleotide set forth in (a);

(c) a polynucleotide encoding a protein consisting of the amino acid sequence of SEQ ID NO: 20;

(d) a polynucleotide encoding a protein consisting of an amino acid sequence including deletion, substitution, insertion, and/or addition of one or more amino acids in the amino acid sequence of SEQ ID NO: 20 and having the same activity as a protein encoded by the polynucleotide set forth in (c); and (e) a polynucleotide encoding a protein having an amino acid sequence with at least 90% sequence identity to the amino acid sequence of SEQ ID NO: 20 and having the same activity as a protein encoded by the polynucleotide set forth in (c).

The source of the CGT gene, which is an essential gene in pathway 2, or a homologue thereof, is not particularly limited provided the desired function is exhibited, but is preferably a *Gentiana scabra*-derived CGT gene or a homologue thereof comprising a polynucleotide selected from the following group consisting of:

(a) a polynucleotide consisting of the base sequence of SEQ ID NO: 21;

(b) a polynucleotide hybridizing to a polynucleotide consisting of a base sequence complimentary to the base sequence of SEQ ID NO: 21 under stringent conditions and encoding a protein having the same activity as a protein encoded by the polynucleotide set forth in (2-a);

(c) a polynucleotide encoding a protein consisting of the amino acid sequence of SEQ ID NO: 22;

(d) a polynucleotide encoding a protein consisting of an amino acid sequence including deletion, substitution, insertion, and/or addition of one or more amino acids in the amino acid sequence of SEQ ID NO: 22 and having the same activity as a protein encoded by the polynucleotide set forth in (2-c); and (e) a polynucleotide encoding a protein having an amino acid sequence with at least 90% sequence identity to the amino acid sequence of SEQ ID NO: 22 and the same activity as a protein encoded by the polynucleotide set forth in (c).

It is preferable for the CGT gene, which is an essential gene in pathway 2, or a homologue thereof to have added thereto an *Arabidopsis* alcohol dehydrogenase (ADH) gene-derived 5' untranslated region (5'-UTR) (SEQ ID NO: 23).

Accumulation of a delphinidin-type anthocyanin within plant cells can be achieved by incorporating a flavonoid 3',5'-hydroxylase (F3'S'H) gene or a homologue thereof and a methyltransferase (MT) gene or a homologue thereof into a host plant (PTL2). Thus, delphinidin-type anthocyanin and flavone C-glycoside can be made to coexist with cells of a host plant by transforming the host plant with a vector that further contains an F3'S'H gene or a homologue thereof and an MT gene or a homologue thereof in addition to the essential genes for pathways 1 and 2 and the homologues thereof.

The source of the F3'S'H gene or a homologue thereof, is not particularly limited provided the desired function is exhibited, but is preferably a *Campanula*-derived F3'S'H gene or a homologue thereof comprising a polynucleotide selected from the following group consisting of:

(a) a polynucleotide consisting of the base sequence of SEQ ID NO: 9;

(b) a polynucleotide hybridizing to a polynucleotide consisting of a base sequence complimentary to the base sequence of SEQ ID NO: 9 under stringent conditions and encoding a protein having the same activity as a protein encoded by the polynucleotide set forth in (a);

(c) a polynucleotide encoding a protein consisting of the amino acid sequence of SEQ ID NO: 10;

(d) a polynucleotide encoding a protein consisting of an amino acid sequence including deletion, substitution, insertion, and/or addition of one or more amino acids in the amino acid sequence of SEQ ID NO: 10 and having the same activity as a protein encoded by the polynucleotide set forth in (c); and (e) a polynucleotide encoding a protein having an amino acid sequence with at least 90% sequence identity to the amino acid sequence of SEQ ID NO: 10 and the same activity as a protein encoded by the polynucleotide set forth in (c).

The source of the MT gene or a homologue thereof, is not particularly limited provided the desired function is exhibited, but is preferably a *Torenia*-derived MT gene or a homologue thereof comprising a polynucleotide selected from the following group consisting of:

(a) a polynucleotide consisting of the base sequence of SEQ ID NO: 17;

(b) a polynucleotide hybridizing to a polynucleotide consisting of a base sequence complimentary to the base sequence of SEQ ID NO: 17 under stringent conditions and encoding a protein having the same activity as a protein encoded by the polynucleotide set forth in (a);

(c) a polynucleotide encoding a protein consisting of the amino acid sequence of SEQ ID NO: 18;

(d) a polynucleotide encoding a protein consisting of an amino acid sequence including deletion, substitution, insertion, and/or addition of one or more amino acids in the amino acid sequence of SEQ ID NO: 18 and having the same activity as a protein encoded by the polynucleotide set forth in (c);

(e) a polynucleotide encoding a protein having an amino acid sequence with at least 90% sequence identity to the amino acid sequence of SEQ ID NO: 18 and having the same activity as a protein encoded by the polynucleotide set forth in (c).

Herein, the term "nucleotide" refers to DNA or RNA. Herein, the term "stringent conditions" refers to conditions that allow selective and detectable specific binding of polynucleotides or oligonucleotides to genomic DNA. Stringent conditions are defined according to an appropriate combination of salt concentration, organic solvent (e.g. formamide) temperature, and other publicly known conditions. Namely, stringency is increased depending on whether the salt concentration is decreased, the organic solvent concentration is increased, or the hybridization temperature is increased. Furthermore, washing conditions after hybridization are also affected by stringency. These washing conditions are defined according to salt concentration and temperature, and washing stringency is increased depending on whether the salt concentration is decreased or temperature is increased. Thus, the term "stringent conditions" means conditions under which specific hybridization occurs only when the base sequences have a high sequence identity where the degree of "sequence identity" between each base sequence is, for example, as an average for the whole sequence, at least about 80%, preferably at least about 90%, more preferably at least about 95%, even more preferably at least 97% and most preferably 98%. An example of "stringent conditions" are a temperature of 60° C. to 68° C., a sodium concentration of 150 to 900 mM, preferably 600 to 900 mM, a pH of 6 to 8, and as a specific example, hybridization can be performed under conditions that include 5×SSC (750 mN NaCl, 75 mM trisodium citrate), 1% SDS, 5×Denhardt's solution 50% formaldehyde at 42° C. and washing can be performed under conditions that include 0.1×SSC (15 mM NaCl. 1.5 mM trisodium citrate), 0.1% SDS, and 55° C.

Hybridization can be performed according to publicly known methods in the art such as the method disclosed in Current protocols in molecular biology (edited by Frederick M. Ausubel et al., 1987) or methods based thereon. Further, when using commercially available libraries, hybridization can be performed by following the method described in the attached instruction manual. Genes selected by such hybridization methods may be derived from nature and may be a gene derived from a plant or a gene that is not derived from a plant. Further, genes selected by hybridization may be cDNA, genomic DNA, or chemically synthesized DNA.

"An amino acid sequence including deletion, substitution, insertion, and/or addition of one or more amino acids" means an amino acid sequence, wherein, for example, any number of amino acids from 1 to 20, preferably 1 to 5, and more preferably 1 to 3, have been deleted, substituted, inserted and/or added. Site-directed mutagenesis, which is a genetic engineering method, is useful for introducing specific mutations at specific sites and can be performed by following the method disclosed in, for example, Molecular Cloning: A Laboratory Manual, 2nd Ed., Cold Spring Harbor Laboratory Press, Cold Spring Harbor, N.Y., 1989. By expressing this mutant DNA using a suitable expression system, a protein consisting of an amino acid sequence including deletion, substitution, insertion, and/or addition of one or more amino acids can be obtained.

Further, the polynucleotides can be obtained by methods publicly known to a person skilled in the art. For example, chemical synthesis methods such as the phosphoramidite method or nucleic acid amplification methods using primers designed based on the nucleotide sequence of the target gene using a plant nucleic acid sample as a template can be used to obtain the polynucleotide.

Herein, the term "sequence identity" refers to the quantity (number) of amino acid residues or nucleotides composing polypeptide sequences (or amino acid sequences) or polynucleotide sequences (or nucleotide sequences), that can be determined to be identical between the two chains, and refers to the degree of sequence correlation between two polypeptide sequences or two polynucleotide sequences. The "sequence identity" can be easily calculated. Many methods for measuring sequence identity between two polynucleotide sequences or polypeptide sequences are known and the term "sequence identity" is well known to a person skilled in the art (for example, refer to Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. & Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991)).

Furthermore, the value of "sequence identity" herein may be a value calculated using a sequence identity search program publicly known to a person skilled in the art, unless otherwise specified, and is preferably a value calculated using the Clustal W program of the MacVector application (version 9.5 Oxford Molecular Ltd., Oxford, England). In the present invention, the degree of sequence identity between each amino acid sequence is, for example, at least about 90%, preferably at least about 95%, more preferably at least about 97%, and most preferably at least about 98%.

The polynucleotide of the present invention (nucleic acid, gene) 'encodes' a protein of interest. Herein "encodes" means expressing the protein of interest so as to be in an active state. 'Encode' can also refer to both the encoding of a protein by a continuous structural sequence (exons) or through intervening sequences (introns).

The sequence of a gene comprising a native base sequence can be obtained by analysis using a DNA sequencer. Further, DNA encoding an enzyme having a modified amino acid sequence can be synthesized by conventional site-directed mutagenesis or PCR based on DNA having the native base sequence. For example, a modified DNA fragment is obtained by treating native cDNA or genomic DNA with a restriction enzyme, this fragment is used as a template and site-directed mutagenesis or PCR is carried out thereon using a primer into which a desired mutation has been introduced and the desired modified DNA fragment is obtained. Thereafter, the DNA fragment into which this mutation has been introduced can be joined to a DNA fragment encoding a different portion of the target enzyme.

Alternatively, in order to obtain DNA that encodes an enzyme comprising a shortened amino acid sequence, for example, an amino acid sequence longer than the target amino acid sequence, for example, the DNA encoding the full-length amino acid sequence is cut with a desired restriction enzyme, and if as a result thereof, the DNA fragment does not encode the entire amino acid sequence, a DNA fragment that encodes the lacking sequence can be synthesized and joined.

Furthermore, the obtained polynucleotide can be expressed in *E. coli* or yeast gene expression systems, and by measuring the enzymatic activity it can be confirmed whether the obtained polynucleotide encodes a protein having the desired activity.

The present invention also relates to (recombinant) vectors comprising the polynucleotide above, especially expression vectors, as well as plants transformed by the vectors.

Furthermore, the vectors of the present invention contain an expression control region, for example, a promoter, a terminator, or a replication origin that is dependent on the type of host plant into which the vector is introduced.

Examples of promoters that will constitutively express polynucleotides within plant cells include the cauliflower mosaic virus 35S promoter, the $El_2$35S promoter that links two enhancer domains of the 35S promoter, the rd29A gene promoter, the rbcS promoter, the mac-1 promoter, etc. Furthermore, for tissue specific gene expression, promoters for the genes that are specifically expressed in the tissue can be used.

The vectors can be produced according to conventional methods such as using restriction enzymes and ligases. Transformation of the host plant with a vector can also be carried out according to conventional methods.

Under the present state of the art, techniques can be used for introducing a polynucleotide into a plant and for expressing this polynucleotide constitutively or tissue-specifically. The introduction of DNA into a plant can be performed by a method that is publicly known to a person skilled in the art, for example, the *agrobacterium* method, binary vector method, electroporation method, PEG method, or particle gun method.

Plants that can be used as hosts in the present invention are not particularly limited but plants of the genus *Rosa* in the family Rosaceae, the genus *Chrysanthemum* in the family Asteraceae, and the genus *Dianthus* in the family Caryophyllaceae (e.g. carnation) can be used, and particularly preferable is the cultivated rose (scientific name: *Rosa hybrida*) of the genus *Rosa* in the family Rosaceae. Note that the term "rose plant" used herein refers to the cultivated rose (scientific name: *Rosa hybrida*) of the genus *Rosa* in the family Rosaceae. Roses are mainly divided into hybrid tea, *floribunda, polyantha*, etc., but there are only two types of the main pigment (anthocyanin) contained in the petals of each of the strains, namely cyanidin and pelargonidin. The variety of rose plant used as the host in the present invention is not particularly limited and these varieties and strains can be used as appropriate. For example, rose varieties that can be used as the host can include Ocean Song, Noblesse, Rita Perfumera, Cool Water, Fame, Topless, Peach Avalanche, etc.

According to the present invention a transformed plant having blue-hued flower color, wherein delphinidin-type anthocyanin and a flavone C-glycoside coexist within the cells can be obtained, the transformed plant preferably being of the genus *Rosa* in the family Rosaceae, the genus *Chrysanthemum* in the family Asteraceae, and the genus *Dianthus* in the family Caryophyllaceae (e.g. carnation), and particularly preferably the rose plant. The obtained transformed plant has a flower color belonging to the Blue group or Violet-Blue group of the RHS color chart and/or a hue angle of 339.7° to 270.0° in the CIE L*a*b* color system.

The present invention also relates: to a cut flower of the transformed plant obtained above, or an inbred or outbred progeny thereof; a propagule thereof; a part of the plant; tissue; or cell; or a processed product produced from the cut flower (particularly processed cut flowers). The processed cut flowers include pressed flowers, preserved flowers, dried flowers, resin-sealed products, etc. but are not limited thereto.

The present invention is specifically described in the following examples.

EXAMPLES

Example 1: Simulation of Copigment Effect Between Anthocyanin and Flavone C-Glycoside Anthocyanin and flavone C-glycoside were prepared so as to perform a simulation of the copigment effect between anthocyanin and flavone C-glycoside. The malvin (malvidin 3,5-diglucoside) and isovitexin (apigenin 6-C-glucoside) used in this experiment were purchased from Funakoshi Corporation.

With respect to the anthocyanin (malvin) obtained thereby, flavone C-glycoside (isovitexin) was added at molar concentration ratios of 0, 2 and 4 equivalents in a pH 4.5 buffer and the absorption spectrum was measured. The concentration of the anthocyanin was made to be 0.5 mM.

By adding the flavone C-glycoside, the absorbance of the aqueous anthocyanin solution increased and the maximum absorbance (λ max) shifted to a longer wavelength with the addition of flavone C-glycoside. This confirms that isovitexin exhibits a copigment effect when combined with malvin.

TABLE 1

Maximum absorbance (λmax) of aqueous anthocyanin solution when flavone C-glycoside is added

| | 0 Equivalents | 2 Equivalents | 4 Equivalents |
|---|---|---|---|
| Malvin (malvidin-3,5-diglucoside) | 531.8 nm | 566.4 nm | 573.0 nm |

Example 2: (Pathway 1) Introduction of Pansy-Derived F3'5H #40 Gene, *Glycyrrhiza*-Derived F2H Gene, *Oryza sativa*-Derived CGT Gene, and *Glycyrrhiza*-Derived FDH Gene into Rose Variety "Rita Perfumera"

pSPB4743 has the basic skeleton of pBINPLUS and contains the following 4 expression cassettes.

(1) $El_2$35S promoter, pansy-derived F3'S'H, full length cDNA (SEQ ID NO:1) and D8 terminator (2) 35S promoter, *Glycyrrhiza*-derived F2H, full length cDNA (SEQ ID NO: 3), and *perilla*-derived AT terminator (3) 35S promoter, *Oryza sativa*-derived CGT, full length cDNA (SEQ ID NO: 5), and *perilla*-derived AT terminator (4) 35S promoter, *Glycyrrhiza*-derived FDH, full length cDNA (SEQ ID NO. 7), and *perilla*-derived AT terminator This plasmid constitutively expresses the pansy F3'5H #40 gene, the *Glycyrrhiza* F2H gene, the *Oryza sativa* CGT gene, and the *Glycyrrhiza* FDH gene in the plant.

The pSPB4743 constructed in this manner was introduced into an orange rose variety "Rita Perfumera" and a total of 16 transformants were obtained. Pigment analysis was carried out thereon and 15 were confirmed to accumulate delphinidin, and the maximum delphinidin content thereof was 94% (average 89.5%). Furthermore, in 10 of the transformants the flavone C-glycoside isovitexin was confirmed and the maximum amount produced per gram of fresh petals was 0.55 mg.

Analyzed values of the transformants are shown below in Table 2

TABLE 2

| Plant No. | Del (%) | Anthocyanidin (mg/g) Del | Cya | Pel | Flavonol (mg/g) M | Q | K | Flavone (mg/g) Tri | Lut | Api | Flavone C-glycoside (mg/g) IVX |
|---|---|---|---|---|---|---|---|---|---|---|---|
| Host | 0.0% | 0.000 | 0.009 | 0.013 | 0.000 | 0.019 | 2.109 | 0.000 | 0.000 | 0.000 | 0.000 |
| 1 | 87.8% | 0.967 | 0.134 | 0.001 | 0.318 | 0.135 | 0.392 | 0.000 | 0.000 | 0.000 | 0.255 |
| 2 | 84.5% | 0.772 | 0.138 | 0.004 | 0.602 | 0.245 | 1.326 | 0.000 | 0.000 | 0.000 | 0.029 |
| 3 | 85.6% | 0.810 | 0.137 | 0.000 | 0.044 | 0.019 | 0.046 | 0.000 | 0.000 | 0.000 | 0.033 |
| 4 | 92.3% | 1.289 | 0.108 | 0.000 | 0.478 | 0.111 | 0.239 | 0.000 | 0.005 | 0.000 | 0.232 |
| 5 | 92.4% | 1.146 | 0.092 | 0.002 | 0.759 | 0.199 | 1.218 | 0.000 | 0.003 | 0.007 | 0.171 |
| 6 | 93.0% | 1.683 | 0.127 | 0.000 | 1.034 | 0.242 | 0.318 | 0.000 | 0.003 | 0.000 | 0.208 |
| 7 | 90.9% | 0.929 | 0.091 | 0.003 | 0.518 | 0.149 | 0.994 | 0.000 | 0.000 | 0.000 | 0.000 |
| 8 | 91.7% | 0.836 | 0.070 | 0.005 | 0.367 | 0.115 | 1.807 | 0.000 | 0.004 | 0.014 | 0.225 |
| 9 | 94.0% | 1.222 | 0.078 | 0.000 | 0.674 | 0.151 | 0.242 | 0.000 | 0.021 | 0.039 | 0.547 |
| 10 | 92.2% | 1.116 | 0.095 | 0.000 | 0.561 | 0.134 | 0.256 | 0.000 | 0.012 | 0.018 | 0.213 |
| 11 | 83.9% | 1.318 | 0.251 | 0.002 | 0.353 | 0.174 | 0.311 | 0.000 | 0.000 | 0.000 | 0.000 |
| 12 | 85.7% | 0.131 | 0.020 | 0.002 | 0.068 | 0.040 | 1.017 | 0.013 | 0.027 | 0.204 | 0.091 |

Host: Rita Perfumera
Del: Delphinidin, Cya: Cyanidin, Pel: Pelargonidin
M: Myricetin, Q: Quercetin, K: Kaempferol
Tri: Tricetin, Lut: Luteolin, Api: Apigenin, IVX: Isovitexin
Del (%): Delphinidin percentage of all anthocyanidins

Example 3: (Pathway 1) Introduction of Pansy-Derived F3'5'H #40 Gene, *Glycyrrhiza*-Derived F2H Gene, *Oryza sativa*-Derived CGT Gene, and *Glycyrrhiza*-Derived FDH Gene into the Rose Variety "Noblesse"

pSPB4743, which was constructed in the same manner as for Example 2, was introduced into a pink rose variety "Noblesse" and a total of 20 transformants were obtained. Pigment analysis was carried out thereon and all were confirmed to accumulate delphinidin, and the maximum delphinidin content thereof was 88% (average 83.5%). Furthermore, in 18 of the transformants the flavone C-glycoside isovitexin was confirmed and the maximum amount produced per gram of fresh petals was 0.06 mg.

Representative analysis values of the transformants are shown below in Table 3.

TABLE 3

| Plant No. | Del (%) | Anthocyanidin (mg/g) Del | Cya | Pel | Flavonol (mg/g) M | Q | K | Flavone (mg/g) Tri | Lut | Api | Flavone C-glycoside (mg/g) IVX |
|---|---|---|---|---|---|---|---|---|---|---|---|
| Host | 0.0% | 0.020 | 0.040 | 0.000 | 0.000 | 0.012 | 1.430 | 0.000 | 0.000 | 0.000 | 0.000 |
| 1 | 85.1% | 1.127 | 0.196 | 0.003 | 0.320 | 0.041 | 0.072 | 0.000 | 0.100 | 0.487 | 0.036 |
| 2 | 85.6% | 2.078 | 0.348 | 0.004 | 0.309 | 0.036 | 0.059 | 0.016 | 0.074 | 0.333 | 0.000 |
| 3 | 85.3% | 1.011 | 0.174 | 0.002 | 0.223 | 0.023 | 0.038 | 0.015 | 0.110 | 0.491 | 0.013 |
| 4 | 85.2% | 0.875 | 0.152 | 0.002 | 0.273 | 0.039 | 0.057 | 0.000 | 0.065 | 0.303 | 0.052 |
| 5 | 83.7% | 1.603 | 0.311 | 0.003 | 0.230 | 0.043 | 0.072 | 0.000 | 0.092 | 0.366 | 0.056 |
| 6 | 87.7% | 3.405 | 0.475 | 0.002 | 0.443 | 0.055 | 0.070 | 0.060 | 0.121 | 0.431 | 0.031 |
| 7 | 80.5% | 2.418 | 0.581 | 0.005 | 0.409 | 0.077 | 0.154 | 0.020 | 0.083 | 0.399 | 0.000 |
| 8 | 84.4% | 1.154 | 0.212 | 0.003 | 0.251 | 0.042 | 0.084 | 0.000 | 0.073 | 0.388 | 0.046 |
| 9 | 82.4% | 1.150 | 0.241 | 0.007 | 0.341 | 0.050 | 0.134 | 0.000 | 0.039 | 0.208 | 0.030 |
| 10 | 83.7% | 1.017 | 0.197 | 0.002 | 0.259 | 0.039 | 0.053 | 0.000 | 0.115 | 0.630 | 0.022 |
| 11 | 87.2% | 1.051 | 0.153 | 0.003 | 0.261 | 0.030 | 0.055 | 0.003 | 0.074 | 0.364 | 0.023 |
| 12 | 80.3% | 1.416 | 0.342 | 0.008 | 0.239 | 0.052 | 0.144 | 0.000 | 0.055 | 0.332 | 0.017 |
| 13 | 80.9% | 0.946 | 0.223 | 0.004 | 0.157 | 0.039 | 0.077 | 0.000 | 0.080 | 0.465 | 0.048 |
| 14 | 83.3% | 1.129 | 0.224 | 0.005 | 0.307 | 0.047 | 0.112 | 0.000 | 0.038 | 0.199 | 0.017 |
| 15 | 80.7% | 1.220 | 0.291 | 0.006 | 0.320 | 0.065 | 0.150 | 0.000 | 0.049 | 0.359 | 0.024 |
| 16 | 86.1% | 1.815 | 0.292 | 0.003 | 0.383 | 0.052 | 0.104 | 0.000 | 0.089 | 0.598 | 0.028 |
| 17 | 85.5% | 1.150 | 0.197 | 0.000 | 0.425 | 0.066 | 0.141 | 0.000 | 0.061 | 0.490 | 0.051 |
| 18 | 82.1% | 1.187 | 0.254 | 0.006 | 0.277 | 0.046 | 0.119 | 0.000 | 0.053 | 0.392 | 0.031 |
| 19 | 78.9% | 0.845 | 0.219 | 0.009 | 0.236 | 0.048 | 0.143 | 0.000 | 0.035 | 0.270 | 0.018 |
| 20 | 82.2% | 0.859 | 0.185 | 0.003 | 0.259 | 0.041 | 0.079 | 0.000 | 0.048 | 0.295 | 0.032 |

Host: Noblesse
Del: Delphinidin, Cya: Cyanidin, Pel: Pelargonidin
M: Myricetin, Q: Quercetin, K: Kaempferol
Tri: Tricetin, Lut: Luteolin, Api: Apigenin, IVX: Isovitexin
Del (%): Delphinidin percentage of all anthocyanidins

Example 4: (Pathway 1) Introduction of *Campanula*-Derived F3'5'H Gene, *Glycyrrhiza*-Derived F2H Gene, *Oryza sativa*-Derived CGT Gene, and *Oryza sativa*-Derived FDH Gene into Rose Variety "Rita Perfumera"

pSPB6188 has the basic skeleton of pBINPLUS and contains the following 4 expression cassettes.

(1) $El_2$35S promoter, *Campanula*-derived F3'5'H, full length cDNA (SEQ ID NO:9) and D8 terminator (2) 35S promoter, *Glycyrrhiza*-derived F2H, full length cDNA (SEQ ID NO: 3), and *perilla*-derived AT terminator (3) $El_2$35S promoter, *Oryza sativa*-derived CGT, full length cDNA (SEQ ID NO:5) and a *perilla*-derived AT terminator (4) $El_2$35S promoter, *Oryza sativa*-derived FDH, full length cDNA (SEQ ID NO:11) and *Arabidopsis*-derived HSP terminator This plasmid constitutively expresses the *Campanula* F3'5'H gene, the *Glycyrrhiza* F2H gene, the *Oryza sativa* CGT gene, and the *Oryza sativa* FDH gene in the plant.

The pSPB6188 constructed in this manner was introduced into an orange rose variety "Rita Perfumera" and a total of 77 transformants were obtained. Pigment analysis was carried out thereon and 68 were confirmed to accumulate delphinidin, and the maximum delphinidin content thereof was 99.6% (average 93.3%). Furthermore, in 57 of the transformants, the flavone C-glycoside isovitexin was confirmed and the maximum amount constructed per gram of fresh petals was 0.72 mg.

Representative analysis values of the transformants are shown below in Table 4.

TABLE 4

| Plant | Del | Anthocyanidin (mg/g) | | | Flavonol (mg/g) | | | Flavone (mg/g) | | | Flavone C-glycoside (mg/g) |
|---|---|---|---|---|---|---|---|---|---|---|---|
| No. | (%) | Del | Cya | Pel | M | Q | K | Tri | Lut | Api | IVX |
| Host | 0.0% | 0.000 | 0.009 | 0.013 | 0.000 | 0.019 | 2.109 | 0.000 | 0.000 | 0.000 | 0.000 |
| 1 | 96.8% | 1.455 | 0.048 | 0.000 | 0.545 | 0.115 | 0.211 | 0.000 | 0.015 | 0.019 | 0.196 |
| 2 | 96.1% | 0.870 | 0.035 | 0.000 | 0.301 | 0.081 | 0.258 | 0.000 | 0.035 | 0.069 | 0.093 |
| 3 | 93.0% | 0.647 | 0.049 | 0.000 | 0.450 | 0.175 | 0.459 | 0.000 | 0.001 | 0.000 | 0.050 |
| 4 | 96.8% | 1.166 | 0.039 | 0.000 | 0.609 | 0.143 | 0.202 | 0.000 | 0.002 | 0.001 | 0.086 |
| 5 | 97.1% | 1.384 | 0.041 | 0.000 | 0.473 | 0.100 | 0.134 | 0.000 | 0.003 | 0.000 | 0.087 |
| 6 | 95.3% | 0.632 | 0.031 | 0.000 | 0.387 | 0.101 | 0.137 | 0.000 | 0.000 | 0.000 | 0.037 |
| 7 | 93.9% | 1.274 | 0.083 | 0.000 | 0.426 | 0.166 | 0.284 | 0.000 | 0.003 | 0.001 | 0.039 |
| 8 | 95.7% | 0.802 | 0.036 | 0.000 | 0.300 | 0.083 | 0.100 | 0.000 | 0.002 | 0.000 | 0.070 |
| 9 | 94.7% | 1.522 | 0.085 | 0.000 | 0.526 | 0.198 | 0.382 | 0.000 | 0.002 | 0.000 | 0.033 |
| 10 | 94.4% | 1.412 | 0.084 | 0.000 | 0.350 | 0.152 | 0.232 | 0.000 | 0.002 | 0.000 | 0.039 |
| 11 | 93.7% | 1.300 | 0.088 | 0.000 | 0.286 | 0.114 | 0.175 | 0.000 | 0.002 | 0.001 | 0.137 |
| 12 | 97.5% | 1.842 | 0.047 | 0.000 | 0.589 | 0.088 | 0.072 | 0.000 | 0.010 | 0.005 | 0.042 |
| 13 | 97.5% | 1.423 | 0.037 | 0.000 | 0.416 | 0.066 | 0.046 | 0.000 | 0.010 | 0.007 | 0.024 |
| 14 | 95.0% | 0.935 | 0.049 | 0.000 | 0.456 | 0.161 | 0.302 | 0.000 | 0.001 | 0.000 | 0.054 |
| 15 | 93.7% | 1.272 | 0.085 | 0.000 | 0.509 | 0.224 | 0.547 | 0.000 | 0.001 | 0.001 | 0.063 |
| 16 | 93.2% | 0.504 | 0.037 | 0.000 | 0.166 | 0.063 | 0.122 | 0.000 | 0.000 | 0.000 | 0.049 |
| 17 | 93.7% | 1.158 | 0.078 | 0.000 | 0.466 | 0.208 | 0.652 | 0.000 | 0.000 | 0.000 | 0.042 |
| 18 | 98.2% | 1.152 | 0.021 | 0.000 | 0.514 | 0.072 | 0.063 | 0.000 | 0.003 | 0.001 | 0.098 |
| 19 | 94.8% | 1.171 | 0.065 | 0.000 | 0.226 | 0.072 | 0.104 | 0.000 | 0.002 | 0.001 | 0.148 |
| 20 | 90.1% | 0.729 | 0.078 | 0.002 | 0.268 | 0.188 | 0.760 | 0.000 | 0.003 | 0.006 | 0.263 |
| 21 | 93.2% | 1.120 | 0.082 | 0.000 | 0.449 | 0.240 | 0.912 | 0.000 | 0.000 | 0.000 | 0.034 |
| 22 | 93.9% | 1.169 | 0.076 | 0.000 | 0.394 | 0.168 | 0.264 | 0.000 | 0.002 | 0.000 | 0.058 |
| 23 | 98.5% | 1.387 | 0.021 | 0.000 | 0.603 | 0.072 | 0.051 | 0.000 | 0.031 | 0.026 | 0.029 |
| 24 | 94.7% | 1.319 | 0.074 | 0.000 | 0.604 | 0.214 | 0.354 | 0.000 | 0.002 | 0.000 | 0.062 |
| 25 | 96.9% | 1.859 | 0.060 | 0.000 | 0.765 | 0.169 | 0.195 | 0.000 | 0.003 | 0.000 | 0.262 |
| 26 | 75.8% | 0.078 | 0.023 | 0.002 | 0.021 | 0.031 | 0.548 | 0.008 | 0.004 | 0.089 | 0.719 |
| 27 | 97.7% | 1.847 | 0.043 | 0.000 | 0.404 | 0.071 | 0.064 | 0.003 | 0.004 | 0.003 | 0.226 |
| 28 | 94.4% | 0.934 | 0.056 | 0.000 | 0.294 | 0.110 | 0.122 | 0.003 | 0.002 | 0.001 | 0.109 |
| 29 | 94.5% | 1.106 | 0.065 | 0.000 | 0.280 | 0.118 | 0.122 | 0.003 | 0.002 | 0.002 | 0.083 |
| 30 | 94.4% | 0.621 | 0.037 | 0.000 | 0.294 | 0.094 | 0.160 | 0.001 | 0.001 | 0.002 | 0.066 |
| 31 | 98.5% | 1.668 | 0.026 | 0.000 | 0.616 | 0.072 | 0.036 | 0.005 | 0.010 | 0.009 | 0.041 |
| 32 | 98.2% | 2.288 | 0.042 | 0.000 | 0.618 | 0.081 | 0.077 | 0.008 | 0.023 | 0.022 | 0.160 |
| 33 | 98.4% | 2.080 | 0.033 | 0.000 | 0.525 | 0.067 | 0.048 | 0.005 | 0.012 | 0.010 | 0.142 |
| 34 | 97.2% | 1.059 | 0.031 | 0.000 | 0.569 | 0.108 | 0.169 | 0.005 | 0.011 | 0.014 | 0.213 |
| 35 | 98.0% | 1.029 | 0.021 | 0.000 | 0.199 | 0.031 | 0.028 | 0.002 | 0.010 | 0.009 | 0.047 |
| 36 | 96.9% | 1.338 | 0.043 | 0.000 | 0.252 | 0.056 | 0.111 | 0.004 | 0.005 | 0.006 | 0.165 |
| 37 | 97.7% | 1.493 | 0.035 | 0.000 | 0.422 | 0.078 | 0.040 | 0.004 | 0.006 | 0.004 | 0.076 |
| 38 | 95.7% | 1.305 | 0.059 | 0.000 | 0.391 | 0.128 | 0.105 | 0.007 | 0.003 | 0.002 | 0.113 |
| 39 | 97.9% | 1.199 | 0.026 | 0.000 | 0.280 | 0.048 | 0.030 | 0.004 | 0.010 | 0.006 | 0.035 |
| 40 | 94.7% | 1.284 | 0.072 | 0.000 | 0.264 | 0.090 | 0.113 | 0.007 | 0.002 | 0.002 | 0.068 |
| 41 | 94.4% | 0.517 | 0.031 | 0.000 | 0.106 | 0.037 | 0.042 | 0.000 | 0.003 | 0.002 | 0.070 |
| 42 | 97.0% | 1.734 | 0.053 | 0.000 | 0.867 | 0.169 | 0.183 | 0.007 | 0.006 | 0.008 | 0.076 |
| 43 | 90.6% | 0.617 | 0.064 | 0.001 | 0.183 | 0.097 | 0.259 | 0.003 | 0.001 | 0.003 | 0.055 |
| 44 | 97.0% | 1.157 | 0.036 | 0.000 | 0.258 | 0.053 | 0.038 | 0.002 | 0.008 | 0.006 | 0.059 |
| 45 | 97.6% | 1.662 | 0.041 | 0.000 | 0.382 | 0.077 | 0.041 | 0.001 | 0.003 | 0.001 | 0.125 |
| 46 | 98.2% | 1.456 | 0.026 | 0.000 | 0.620 | 0.083 | 0.050 | 0.003 | 0.005 | 0.004 | 0.125 |
| 47 | 97.9% | 0.875 | 0.019 | 0.000 | 0.271 | 0.035 | 0.018 | 0.002 | 0.018 | 0.013 | 0.018 |
| 48 | 98.2% | 1.281 | 0.024 | 0.000 | 0.171 | 0.025 | 0.018 | 0.001 | 0.011 | 0.008 | 0.048 |
| 49 | 95.1% | 1.611 | 0.083 | 0.000 | 0.684 | 0.235 | 0.338 | 0.014 | 0.002 | 0.000 | 0.202 |
| 50 | 93.4% | 0.779 | 0.056 | 0.000 | 0.217 | 0.091 | 0.125 | 0.002 | 0.001 | 0.002 | 0.078 |

Example 5: (Pathway 1) Introduction of *Campanula*-Derived F3'S'H Gene, *Glycyrrhiza*-Derived F2H Gene, *Oryza sativa*-Derived CGT Gene, and *Oryza sativa*-Derived FDH Gene into Rose Variety "Noblesse"

pSPB6188, which was constructed in the same manner as for Example 4, was introduced into a pink rose variety "Noblesse" and a total of 51 transformants were obtained. Pigment analysis was carried out thereon and all were confirmed to accumulate delphinidin, and the maximum delphinidin content thereof was 99.7% (average 66.9%). Furthermore, in 48 of the transformants the flavone C-glycoside isovitexin was confirmed and the maximum amount produced per gram of fresh petals was 0.58 mg.

Representative analysis values of the transformants are shown below in Table 5.

TABLE 5

| Plant | Del | Anthocyanidin (mg/g) | | | Flavonol (mg/g) | | | Flavone (mg/g) | | | Flavone C-glycoside (mg/g) |
|---|---|---|---|---|---|---|---|---|---|---|---|
| No. | (%) | Del | Cya | Pel | M | Q | K | Tri | Lut | Api | IVX |
| Host | 0.0 | 0.020 | 0.040 | 0.000 | 0.000 | 0.012 | 1.430 | 0.000 | 0.000 | 0.000 | 0.000 |
| 1 | 97.1 | 1.312 | 0.039 | 0.000 | 0.382 | 0.026 | 0.055 | 0.008 | 0.002 | 0.004 | 0.553 |
| 2 | 97.0 | 1.562 | 0.049 | 0.000 | 0.501 | 0.036 | 0.085 | 0.012 | 0.002 | 0.004 | 0.580 |
| 3 | 96.6 | 1.185 | 0.042 | 0.000 | 0.423 | 0.030 | 0.075 | 0.010 | 0.002 | 0.005 | 0.523 |
| 4 | 76.3 | 0.522 | 0.139 | 0.024 | 0.100 | 0.034 | 0.609 | 0.044 | 0.010 | 0.092 | 0.033 |
| 5 | 92.9 | 0.475 | 0.033 | 0.003 | 0.130 | 0.015 | 0.104 | 0.014 | 0.026 | 0.111 | 0.044 |
| 6 | 86.2 | 0.374 | 0.055 | 0.005 | 0.119 | 0.029 | 0.182 | 0.017 | 0.016 | 0.128 | 0.061 |
| 7 | 73.0 | 0.244 | 0.075 | 0.016 | 0.029 | 0.011 | 0.154 | 0.011 | 0.014 | 0.086 | 0.020 |
| 8 | 89.9 | 0.201 | 0.020 | 0.003 | 0.026 | 0.005 | 0.046 | 0.020 | 0.128 | 0.264 | 0.132 |
| 9 | 75.7 | 0.217 | 0.060 | 0.010 | 0.044 | 0.017 | 0.158 | 0.025 | 0.074 | 0.302 | 0.327 |
| 10 | 89.5 | 0.881 | 0.095 | 0.009 | 0.057 | 0.013 | 0.088 | 0.007 | 0.007 | 0.027 | 0.252 |
| 11 | 92.0 | 0.667 | 0.055 | 0.004 | 0.189 | 0.030 | 0.182 | 0.017 | 0.008 | 0.028 | 0.305 |
| 12 | 93.2 | 0.523 | 0.035 | 0.003 | 0.110 | 0.015 | 0.083 | 0.007 | 0.013 | 0.062 | 0.227 |
| 13 | 66.1 | 0.211 | 0.098 | 0.012 | 0.053 | 0.027 | 0.335 | 0.018 | 0.023 | 0.303 | 0.104 |
| 14 | 66.5 | 0.172 | 0.068 | 0.020 | 0.057 | 0.020 | 0.362 | 0.023 | 0.003 | 0.049 | 0.017 |
| 15 | 88.9 | 0.908 | 0.101 | 0.013 | 0.127 | 0.025 | 0.288 | 0.043 | 0.117 | 0.335 | 0.202 |
| 16 | 51.0 | 0.120 | 0.106 | 0.010 | 0.023 | 0.032 | 0.413 | 0.023 | 0.034 | 0.519 | 0.130 |
| 17 | 41.3 | 0.121 | 0.136 | 0.037 | 0.038 | 0.028 | 0.926 | 0.038 | 0.015 | 0.348 | 0.086 |
| 18 | 58.8 | 0.262 | 0.165 | 0.020 | 0.029 | 0.035 | 0.476 | 0.032 | 0.039 | 0.465 | 0.136 |
| 19 | 96.0 | 0.888 | 0.037 | 0.001 | 0.425 | 0.037 | 0.133 | 0.013 | 0.002 | 0.003 | 0.266 |
| 20 | 94.9 | 0.783 | 0.043 | 0.000 | 0.611 | 0.060 | 0.287 | 0.016 | 0.002 | 0.006 | 0.178 |
| 21 | 99.4 | 0.727 | 0.004 | 0.000 | 0.255 | 0.004 | 0.002 | 0.020 | 0.091 | 0.055 | 0.266 |
| 22 | 99.6 | 0.860 | 0.004 | 0.000 | 0.258 | 0.002 | 0.002 | 0.027 | 0.134 | 0.097 | 0.123 |
| 23 | 99.7 | 1.028 | 0.004 | 0.000 | 0.367 | 0.004 | 0.002 | 0.025 | 0.124 | 0.093 | 0.223 |
| 24 | 93.3 | 0.682 | 0.049 | 0.000 | 0.188 | 0.009 | 0.017 | 0.031 | 0.165 | 0.260 | 0.346 |
| 25 | 99.0 | 0.861 | 0.009 | 0.000 | 0.397 | 0.007 | 0.006 | 0.023 | 0.130 | 0.139 | 0.151 |
| 26 | 99.6 | 0.374 | 0.001 | 0.000 | 0.227 | 0.002 | 0.001 | 0.030 | 0.156 | 0.142 | 0.095 |
| 27 | 60.9 | 0.112 | 0.067 | 0.005 | 0.019 | 0.016 | 0.105 | 0.015 | 0.118 | 0.759 | 0.248 |
| 28 | 91.3 | 0.941 | 0.087 | 0.003 | 0.354 | 0.033 | 0.138 | 0.014 | 0.001 | 0.003 | 0.234 |
| 29 | 98.2 | 0.820 | 0.015 | 0.000 | 0.334 | 0.012 | 0.023 | 0.016 | 0.067 | 0.074 | 0.046 |

Host: Noblesse
Del: Delphinidin, Cya: Cyanidin, Pel: Pelargonidin
M: Myricetin, Q: Quercetin, K: Kaempferol
Tri: Tricetin, Lut: Luteolin, Api: Apigenin, IVX: Isovitexin
Del (%): Delphinidin percentage of all anthocyanidins

Example 6: (Pathway 1) Introduction of Pansy-Derived F3'5'H #40 Gene *Glycyrrhiza*-Derived F2H Gene, *Oryza sativa*-Derived Codon-Usage Modified CGT Gene, and *Lotus japonicus*-Derived FDH Gene into Rose Variety "Rita Perfumera"

pSPB5588 has the basic skeleton of pBINPLUS and contains the following 4 expression cassettes.

(1) $El_2$35S promoter, pansy-derived F3'S'H, full length cDNA (SEQ ID NO:1) and D8 terminator (2) 35S promoter, *Campanula*-derived F2H, full length cDNA (SEQ ID NO: 3), and *perilla*-derived AT terminator (3) 35S promoter, *Oryza sativa*-derived codon-usage modified CGT, full length cDNA (SEQ ID NO:13) and an *Arabidopsis*-derived HSP terminator (4) 35S promoter, *Lotus japonicus*-derived FDH, full length cDNA (SEQ ID NO:15) and *Arabidopsis*-derived HSP terminator This plasmid constitutively expresses the pansy F3'5'H #40 gene, the *Glycyrrhiza* F2H gene, the *Oryza sativa* codon-usage modified CGT gene, and the *Lotus japonicus* FDH gene in the plant.

The pSPB5588 constructed in this manner was introduced into an orange rose variety "Rita Perfumera" and a total of 92 transformants were obtained. Pigment analysis was carried out on 65 thereof and 44 were confirmed to accumulate delphinidin, and the maximum delphinidin content thereof was 100% (average 62.3%). Furthermore, in 37 of the transformants the flavone C-glycoside isovitexin was confirmed and the maximum amount produced per gram of fresh petals was a high content of 2.02 mg.

Representative analysis values of the transformants are shown below in Table 6.

TABLE 6

| Plant No. | Del (%) | Anthocyanidin (mg/g) Del | Cya | Pel | Flavonol (mg/g) M | Q | K | Flavone (mg/g) Tri | Lut | Api | Flavone C-glycoside (mg/g) IVX |
|---|---|---|---|---|---|---|---|---|---|---|---|
| Host | 0.0% | 0.000 | 0.009 | 0.013 | 0.000 | 0.019 | 2.109 | 0.000 | 0.000 | 0.000 | 0.000 |
| 1 | 89.3% | 0.819 | 0.097 | 0.002 | 0.864 | 0.289 | 0.922 | 0.000 | 0.000 | 0.000 | 0.151 |
| 2 | 90.2% | 0.404 | 0.044 | 0.001 | 0.583 | 0.213 | 1.008 | 0.000 | 0.000 | 0.000 | 0.028 |
| 3 | 77.6% | 0.116 | 0.029 | 0.004 | 0.120 | 0.090 | 2.945 | 0.000 | 0.000 | 0.000 | 0.291 |
| 4 | 71.7% | 0.091 | 0.033 | 0.003 | 0.118 | 0.092 | 1.174 | 0.000 | 0.000 | 0.017 | 0.231 |
| 5 | 70.8% | 0.144 | 0.054 | 0.006 | 0.010 | 0.028 | 0.387 | 0.000 | 0.003 | 0.025 | 0.446 |
| 6 | 83.4% | 0.655 | 0.128 | 0.003 | 0.547 | 0.338 | 1.877 | 0.000 | 0.007 | 0.022 | 0.368 |
| 7 | 84.9% | 0.625 | 0.111 | 0.001 | 0.293 | 0.146 | 0.311 | 0.000 | 0.007 | 0.028 | 0.085 |
| 8 | 100.0% | 0.107 | 0.000 | 0.000 | 0.286 | 0.147 | 0.510 | 0.000 | 0.000 | 0.000 | 0.007 |
| 9 | 69.3% | 0.055 | 0.022 | 0.002 | 0.039 | 0.034 | 0.815 | 0.000 | 0.000 | 0.045 | 0.127 |
| 10 | 67.6% | 0.061 | 0.026 | 0.003 | 0.057 | 0.049 | 1.131 | 0.000 | 0.000 | 0.093 | 0.267 |
| 11 | 46.7% | 0.031 | 0.032 | 0.004 | 0.000 | 0.047 | 1.150 | 0.000 | 0.003 | 0.070 | 0.547 |
| 12 | 60.0% | 0.052 | 0.028 | 0.007 | 0.029 | 0.030 | 1.066 | 0.000 | 0.000 | 0.071 | 0.188 |
| 13 | 64.6% | 0.029 | 0.013 | 0.003 | 0.034 | 0.031 | 1.096 | 0.000 | 0.000 | 0.087 | 0.199 |
| 14 | 68.9% | 0.046 | 0.017 | 0.003 | 0.048 | 0.045 | 1.489 | 0.000 | 0.000 | 0.082 | 0.303 |
| 15 | 88.9% | 0.769 | 0.097 | 0.000 | 1.066 | 0.403 | 1.601 | 0.000 | 0.007 | 0.046 | 0.091 |
| 16 | 87.0% | 1.302 | 0.194 | 0.002 | 0.392 | 0.140 | 0.362 | 0.000 | 0.000 | 0.000 | 0.024 |
| 17 | 49.7% | 0.025 | 0.023 | 0.002 | 0.036 | 0.048 | 1.097 | 0.000 | 0.004 | 0.141 | 0.453 |
| 18 | 68.9% | 0.091 | 0.039 | 0.002 | 0.065 | 0.054 | 0.552 | 0.000 | 0.004 | 0.068 | 0.239 |
| 19 | 64.8% | 0.059 | 0.027 | 0.005 | 0.000 | 0.049 | 1.528 | 0.000 | 0.000 | 0.072 | 0.738 |
| 20 | 87.0% | 0.574 | 0.085 | 0.001 | 0.259 | 0.097 | 0.213 | 0.000 | 0.004 | 0.010 | 0.027 |
| 21 | 67.0% | 0.037 | 0.014 | 0.005 | 0.041 | 0.033 | 1.481 | 0.000 | 0.000 | 0.046 | 0.075 |
| 22 | 66.3% | 0.091 | 0.040 | 0.007 | 0.049 | 0.052 | 1.590 | 0.000 | 0.000 | 0.049 | 0.379 |
| 23 | 86.6% | 0.780 | 0.121 | 0.001 | 0.378 | 0.165 | 0.306 | 0.000 | 0.010 | 0.029 | 0.123 |
| 24 | 89.8% | 1.128 | 0.127 | 0.001 | 0.432 | 0.122 | 0.188 | 0.000 | 0.008 | 0.022 | 0.108 |
| 25 | 87.0% | 0.508 | 0.075 | 0.001 | 0.286 | 0.107 | 0.203 | 0.000 | 0.008 | 0.026 | 0.071 |
| 26 | 92.1% | 0.907 | 0.076 | 0.002 | 0.289 | 0.076 | 0.131 | 0.000 | 0.005 | 0.011 | 0.056 |
| 27 | 87.1% | 0.758 | 0.110 | 0.002 | 0.260 | 0.092 | 0.252 | 0.000 | 0.006 | 0.023 | 0.211 |
| 28 | 30.8% | 0.005 | 0.007 | 0.005 | 0.006 | 0.019 | 1.803 | 0.000 | 0.000 | 0.030 | 0.112 |
| 29 | 64.6% | 0.062 | 0.030 | 0.004 | 0.047 | 0.054 | 1.794 | 0.000 | 0.008 | 0.183 | 1.479 |
| 30 | 57.5% | 0.037 | 0.023 | 0.005 | 0.020 | 0.038 | 1.447 | 0.000 | 0.002 | 0.058 | 0.408 |
| 31 | 85.1% | 0.421 | 0.073 | 0.001 | 0.277 | 0.120 | 0.263 | 0.000 | 0.008 | 0.033 | 0.053 |
| 32 | 51.2% | 0.058 | 0.051 | 0.003 | 0.040 | 0.070 | 1.003 | 0.000 | 0.000 | 0.117 | 2.016 |
| 33 | 60.2% | 0.070 | 0.041 | 0.005 | 0.050 | 0.070 | 1.376 | 0.000 | 0.000 | 0.067 | 1.027 |
| 34 | 87.3% | 1.225 | 0.176 | 0.002 | 0.255 | 0.138 | 0.354 | 0.015 | 0.010 | 0.044 | 0.643 |

Host: Rita Perfumera
Del: Delphinidin, Cya: Cyanidin, Pel: Pelargonidin
M: Myricetin, Q: Quercetin, K: Kaempferol
Tri: Tricetin, Lut: Luteolin, Api: Apigenin, IVX: Isovitexin
Del (%): Delphinidin percentage of all anthocyanidins

Example 7: (Pathway 1) Introduction of Pansy-Derived F3'5'H #40 Gene, *Glycyrrhiza*-Derived F2H Gene, *Oryza sativa*-Derived Codon-Usage Modified CGT Gene, and *Lotus japonicus*-Derived FDH Gene into Rose Variety “Noblesse”

pSPB5588, which was constructed in the same manner as for Example 4, was introduced into an orange rose variety “Noblesse” and a total of 60 transformants were obtained. Pigment analysis was carried out thereon and 42 were confirmed to accumulate delphinidin, and the maximum delphinidin content thereof was 96.9% (average 54.4%). Furthermore, in 29 of the transformants, the flavone C-glycoside isovitexin was confirmed and the maximum amount produced per gram of fresh petals was a high content of 1.60 mg.

Representative analysis values of the transformants are shown below in Table 7.

TABLE 7

| Plant No. | Del (%) | Anthocyanidin (mg/g) Del | Cya | Pel | Flavonol (mg/g) M | Q | K | Flavone (mg/g) Tri | Lut | Api | Flavone C-glycoside (mg/g) IVX |
|---|---|---|---|---|---|---|---|---|---|---|---|
| Host | 0.0% | 0.020 | 0.040 | 0.000 | 0.000 | 0.012 | 1.430 | 0.000 | 0.000 | 0.000 | 0.000 |
| 1 | 67.6% | 0.372 | 0.156 | 0.023 | 0.074 | 0.034 | 0.637 | 0.000 | 0.000 | 0.043 | 1.398 |
| 2 | 68.2% | 0.145 | 0.051 | 0.016 | 0.056 | 0.024 | 0.707 | 0.000 | 0.000 | 0.045 | 0.712 |
| 3 | 55.4% | 0.151 | 0.097 | 0.025 | 0.033 | 0.025 | 0.739 | 0.000 | 0.000 | 0.120 | 1.602 |
| 4 | 50.5% | 0.174 | 0.121 | 0.050 | 0.035 | 0.023 | 0.802 | 0.000 | 0.000 | 0.012 | 0.333 |
| 5 | 58.9% | 0.247 | 0.131 | 0.041 | 0.047 | 0.027 | 0.712 | 0.000 | 0.000 | 0.005 | 0.058 |
| 6 | 69.3% | 0.398 | 0.152 | 0.025 | 0.107 | 0.045 | 1.008 | 0.000 | 0.000 | 0.029 | 1.045 |
| 7 | 59.2% | 0.283 | 0.161 | 0.036 | 0.059 | 0.032 | 1.041 | 0.000 | 0.000 | 0.016 | 0.655 |
| 8 | 94.2% | 0.899 | 0.056 | 0.000 | 0.348 | 0.030 | 0.072 | 0.000 | 0.002 | 0.009 | 0.507 |
| 9 | 54.3% | 0.384 | 0.252 | 0.070 | 0.077 | 0.047 | 1.075 | 0.000 | 0.000 | 0.000 | 0.098 |

TABLE 7-continued

| Plant No. | Del (%) | Anthocyanidin (mg/g) Del | Cya | Pel | Flavonol (mg/g) M | Q | K | Flavone (mg/g) Tri | Lut | Api | Flavone C-glycoside (mg/g) IVX |
|---|---|---|---|---|---|---|---|---|---|---|---|
| 10 | 95.1% | 1.580 | 0.083 | 0.000 | 0.426 | 0.037 | 0.067 | 0.000 | 0.010 | 0.035 | 1.015 |
| 11 | 66.5% | 0.160 | 0.068 | 0.013 | 0.051 | 0.025 | 0.672 | 0.000 | 0.000 | 0.096 | 1.426 |
| 12 | 90.6% | 1.226 | 0.128 | 0.001 | 0.346 | 0.042 | 0.101 | 0.000 | 0.019 | 0.086 | 0.792 |
| 13 | 81.8% | 0.649 | 0.127 | 0.018 | 0.192 | 0.036 | 0.570 | 0.000 | 0.000 | 0.000 | 0.241 |
| 14 | 83.5% | 0.808 | 0.148 | 0.013 | 0.202 | 0.044 | 0.475 | 0.000 | 0.000 | 0.008 | 0.696 |
| 15 | 86.1% | 0.945 | 0.144 | 0.011 | 0.540 | 0.090 | 0.913 | 0.000 | 0.000 | 0.021 | 0.951 |
| 16 | 92.5% | 0.981 | 0.080 | 0.000 | 0.592 | 0.048 | 0.131 | 0.000 | 0.003 | 0.019 | 0.264 |
| 17 | 32.2% | 0.099 | 0.140 | 0.070 | 0.050 | 0.039 | 1.803 | 0.000 | 0.000 | 0.001 | 0.044 |
| 18 | 60.4% | 0.071 | 0.031 | 0.015 | 0.085 | 0.024 | 0.829 | 0.000 | 0.000 | 0.000 | 0.028 |
| 19 | 91.6% | 0.689 | 0.063 | 0.000 | 0.523 | 0.043 | 0.272 | 0.000 | 0.001 | 0.014 | 0.195 |
| 20 | 85.3% | 0.660 | 0.104 | 0.010 | 0.360 | 0.047 | 0.531 | 0.000 | 0.001 | 0.008 | 0.288 |
| 21 | 89.6% | 0.340 | 0.039 | 0.001 | 0.347 | 0.051 | 0.383 | 0.000 | 0.001 | 0.012 | 0.233 |
| 22 | 46.3% | 0.179 | 0.158 | 0.049 | 0.066 | 0.043 | 1.173 | 0.004 | 0.000 | 0.011 | 0.158 |
| 23 | 95.6% | 1.005 | 0.047 | 0.000 | 0.482 | 0.022 | 0.064 | 0.000 | 0.009 | 0.027 | 0.581 |
| 24 | 96.9% | 0.599 | 0.020 | 0.000 | 0.542 | 0.032 | 0.071 | 0.000 | 0.016 | 0.087 | 0.600 |
| 25 | 94.8% | 1.168 | 0.064 | 0.001 | 0.686 | 0.038 | 0.161 | 0.000 | 0.009 | 0.042 | 1.124 |
| 26 | 75.8% | 0.354 | 0.085 | 0.028 | 0.111 | 0.029 | 0.672 | 0.022 | 0.001 | 0.009 | 0.166 |
| 27 | 77.4% | 0.494 | 0.108 | 0.036 | 0.206 | 0.049 | 1.572 | 0.000 | 0.001 | 0.024 | 0.500 |
| 28 | 76.4% | 0.194 | 0.057 | 0.003 | 0.105 | 0.047 | 0.721 | 0.037 | 0.001 | 0.022 | 0.355 |

Host: Noblesse
Del: Delphinidin, Cya: Cyanidin, Pel: Pelargonidin
M: Myricetin, Q: Quercetin, K: Kaempferol
Tri: Tricetin, Lut: Luteolin, Api: Apigenin, IVX: Isovitexin
Del (%): Delphinidin percentage of all anthocyanidins

Example 8: (Pathway 1) Introduction of *Campanula*-Derived F3'S'H Gene, *Torenia*-Derived MT Gene, *Campanula*-Derived F2H Gene, *Oryza sativa*-Derived Codon-Usage Modified CGT Gene and *Lotus japonicus*-Derived FDH Gene into Rose Variety "Ocean Song"

pSPB6486 has the basic skeleton of pBINPLUS and contains the following 5 expression cassettes.

(1) $El_2$35S promoter, *Campanula*-derived F3'5'H, full length cDNA (SEQ ID NO:9) and D8 terminator (2) $El_2$35S promoter, *Torenia*-derived MT, full length cDNA (SEQ ID NO: 17), and NOS terminator (3) 35S promoter, *Glycyrrhiza*-derived F2H, full length cDNA (SEQ ID NO: 3) and a *perilla*-derived AT terminator (4) 35S promoter, *Oryza sativa*-derived codon-usage modified CGT, full length cDNA (SEQ ID NO:13) and *Arabidopsis*-derived HSP terminator (5) 35S promoter, *Lotus japonicus*-derived FDH, full length cDNA (SEQ ID NO:15) and *Arabidopsis*-derived HSP terminator This plasmid constitutively expresses the *Campanula* F3'5'H gene, the *Torenia* MT gene, the *Glycyrrhiza* F2H gene, the *Oryza sativa* codon-usage modified CGT gene, and the *Lotus japonicus* FDH gene in the plant.

The pSPB6486 constructed in this manner was introduced into a blue-hued rose variety "Ocean song" and a total of 27 transformants were obtained. Pigment analysis was carried out thereon and 26 were confirmed to accumulate malvidin, and the maximum malvidin content thereof was 74.5% (average 57.0%). Furthermore, in this system, in addition to the isovitexin analyzed so far as the flavone C-glycoside, vitexin (apigenin 8-C-glucoside), vicenin-2 (apigenin 6,8-C diglucoside), isoorientin (luteolin 6-C-glucoside) and orientin (luteolin 8-C-glucoside) were also identified and quantified. Flavone C-glycoside could be detected in all of the transformants in which malvidin was detected and from the total amount thereof, the maximum amount produced per gram of fresh petals was a high content of 1.563 mg. Furthermore, in most transformants, the total amount of flavone C-glycoside was a high content of 1 mg or more per gram of fresh petals which was approximately 10 times or more than the amount of malvidin produced.

Representative analysis values of the transformants are shown below in Table 8.

TABLE 8

| Plant No. | Mal (%) | Anthocyanidin (mg/g) Del | Cya | Pet | Pel | Mal | Flavonol (mg/g) M | Q | K | Flavone (mg/g) Tri | Lut | Api | Flavone C-glycoside (mg/g) Vic2 | VX | IVX | Ori | Iori |
|---|---|---|---|---|---|---|---|---|---|---|---|---|---|---|---|---|---|
| Host | 0.0 | 0.000 | 0.024 | 0.000 | 0.000 | 0.000 | 0.000 | 2.883 | 0.586 | 0.000 | 0.000 | 0.000 | 0.000 | 0.000 | 0.000 | 0.000 | 0.000 |
| 1 | 70.8 | 0.024 | 0.000 | 0.009 | 0.000 | 0.080 | 1.225 | 0.077 | 0.023 | 0.000 | 0.013 | 0.010 | 0.187 | 0.205 | 0.505 | 0.009 | 0.073 |
| 2 | 66.2 | 0.025 | 0.000 | 0.007 | 0.000 | 0.062 | 2.453 | 0.181 | 0.020 | 0.009 | 0.047 | 0.029 | 0.743 | 0.109 | 0.319 | 0.027 | 0.077 |
| 3 | 54.6 | 0.022 | 0.006 | 0.008 | 0.000 | 0.050 | 1.058 | 1.381 | 0.515 | 0.000 | 0.000 | 0.000 | 0.896 | 0.093 | 0.219 | 0.000 | 0.015 |
| 4 | 52.7 | 0.020 | 0.003 | 0.007 | 0.000 | 0.035 | 0.858 | 0.482 | 0.178 | 0.000 | 0.003 | 0.006 | 0.429 | 0.174 | 0.354 | 0.007 | 0.035 |
| 5 | 64.0 | 0.028 | 0.000 | 0.009 | 0.000 | 0.065 | 2.045 | 0.168 | 0.063 | 0.000 | 0.000 | 0.000 | 0.586 | 0.130 | 0.299 | 0.002 | 0.030 |
| 6 | 67.7 | 0.028 | 0.000 | 0.007 | 0.000 | 0.074 | 1.593 | 0.455 | 0.115 | 0.011 | 0.010 | 0.009 | 0.795 | 0.126 | 0.355 | 0.018 | 0.050 |
| 7 | 72.1 | 0.027 | 0.000 | 0.008 | 0.000 | 0.089 | 2.753 | 0.526 | 0.183 | 0.006 | 0.004 | 0.004 | 0.905 | 0.093 | 0.262 | 0.000 | 0.028 |
| 8 | 54.7 | 0.019 | 0.007 | 0.005 | 0.000 | 0.049 | 1.010 | 2.128 | 0.418 | 0.018 | 0.002 | 0.005 | 0.945 | 0.226 | 0.325 | 0.000 | 0.021 |
| 9 | 39.1 | 0.018 | 0.009 | 0.004 | 0.000 | 0.025 | 0.679 | 1.438 | 0.322 | 0.005 | 0.002 | 0.002 | 0.672 | 0.246 | 0.283 | 0.007 | 0.020 |
| 10 | 39.8 | 0.013 | 0.009 | 0.005 | 0.000 | 0.021 | 0.447 | 1.129 | 0.586 | 0.000 | 0.000 | 0.002 | 0.432 | 0.080 | 0.179 | 0.000 | 0.010 |

TABLE 8-continued

| Plant | Mal | Anthocyanidin (mg/g) | | | | | Flavonol (mg/g) | | | Flavone (mg/g) | | | Flavone C-glycoside (mg/g) | | | | |
|---|---|---|---|---|---|---|---|---|---|---|---|---|---|---|---|---|---|
| No. | (%) | Del | Cya | Pet | Pel | Mal | M | Q | K | Tri | Lut | Api | Vic2 | VX | IVX | Ori | Iori |
| 11 | 45.9 | 0.011 | 0.011 | 0.006 | 0.000 | 0.034 | 0.914 | 3.471 | 1.481 | 0.000 | 0.000 | 0.000 | 0.839 | 0.050 | 0.118 | 0.000 | 0.003 |
| 12 | 45.4 | 0.022 | 0.005 | 0.007 | 0.000 | 0.032 | 0.803 | 0.992 | 0.418 | 0.000 | 0.004 | 0.005 | 0.511 | 0.142 | 0.354 | 0.000 | 0.024 |
| 13 | 62.8 | 0.032 | 0.000 | 0.008 | 0.000 | 0.067 | 1.830 | 0.210 | 0.059 | 0.018 | 0.023 | 0.015 | 0.910 | 0.000 | 0.249 | 0.000 | 0.049 |
| 14 | 65.6 | 0.024 | 0.000 | 0.007 | 0.000 | 0.060 | 1.942 | 0.258 | 0.078 | 0.011 | 0.019 | 0.015 | 1.047 | 0.056 | 0.305 | 0.016 | 0.054 |
| 15 | 52.9 | 0.042 | 0.002 | 0.009 | 0.000 | 0.062 | 0.993 | 0.377 | 0.100 | 0.000 | 0.004 | 0.005 | 0.396 | 0.197 | 0.450 | 0.000 | 0.050 |
| 16 | 63.9 | 0.031 | 0.000 | 0.007 | 0.000 | 0.067 | 2.742 | 0.221 | 0.056 | 0.009 | 0.030 | 0.018 | 0.591 | 0.063 | 0.285 | 0.022 | 0.058 |
| 17 | 63.5 | 0.016 | 0.000 | 0.005 | 0.000 | 0.037 | 1.767 | 0.102 | 0.013 | 0.009 | 0.051 | 0.029 | 0.621 | 0.147 | 0.242 | 0.022 | 0.061 |
| 18 | 74.5 | 0.029 | 0.000 | 0.009 | 0.000 | 0.109 | 2.078 | 0.187 | 0.029 | 0.017 | 0.030 | 0.015 | 0.604 | 0.051 | 0.276 | 0.021 | 0.061 |
| 19 | 55.4 | 0.019 | 0.009 | 0.006 | 0.000 | 0.059 | 0.937 | 1.893 | 0.502 | 0.008 | 0.001 | 0.000 | 1.002 | 0.078 | 0.218 | 0.000 | 0.007 |
| 20 | 38.5 | 0.006 | 0.010 | 0.002 | 0.000 | 0.019 | 0.480 | 2.621 | 0.468 | 0.007 | 0.001 | 0.003 | 0.890 | 0.147 | 0.247 | 0.000 | 0.012 |
| 21 | 47.7 | 0.025 | 0.000 | 0.009 | 0.000 | 0.031 | 2.684 | 0.376 | 0.102 | 0.008 | 0.019 | 0.018 | 0.700 | 0.147 | 0.303 | 0.017 | 0.048 |
| 22 | 39.5 | 0.011 | 0.013 | 0.003 | 0.000 | 0.026 | 0.497 | 2.333 | 0.524 | 0.000 | 0.004 | 0.008 | 0.720 | 0.224 | 0.346 | 0.009 | 0.030 |
| 23 | 65.3 | 0.019 | 0.001 | 0.007 | 0.000 | 0.055 | 1.615 | 1.007 | 0.223 | 0.005 | 0.001 | 0.000 | 0.828 | 0.101 | 0.207 | 0.000 | 0.013 |
| 24 | 70.0 | 0.028 | 0.000 | 0.008 | 0.000 | 0.087 | 2.776 | 0.531 | 0.166 | 0.000 | 0.001 | 0.000 | 0.913 | 0.055 | 0.178 | 0.000 | 0.012 |
| 25 | 66.2 | 0.014 | 0.003 | 0.007 | 0.000 | 0.058 | 1.428 | 1.898 | 0.525 | 0.000 | 0.008 | 0.014 | 0.907 | 0.255 | 0.368 | 0.000 | 0.034 |
| 26 | 42.7 | 0.036 | 0.017 | 0.011 | 0.000 | 0.063 | 0.991 | 2.495 | 0.457 | 0.000 | 0.000 | 0.000 | 0.529 | 0.030 | 0.094 | 0.000 | 0.000 |

Host: Ocean Song
Del: Delphinidin, Cya: Cyanidin, Pet: Petunidin, Pel: Pelargonidin, Mal: Malvidin
M: Myricetin, Q: Quercetin, K: Kaempferol
Tri: Tricetin, Lut: Luteolin, Api: Apigenin, Vic2: Vicenin-2, VX: Vitexin, IVX: Isovitexin, Ori: Orientin, Iori: Isoorientin
Mal (%): Malvidin percentage of all anthocyanidins

Example 9: (Pathway 2) Introduction of Pansy-Derived F3'5'H #40 Gene, *Torenia*-Derived MT Gene, *Torenia*-Derived FNS Gene, *Gentiana scabra*-Derived CGT Gene into Rose Variety "Rita Perfumera"

pSPB6438 has the basic skeleton of pBINPLUS and contains the following 4 expression cassettes.

(1) $El_2$35S promoter, pansy-derived F3'5'H, full length cDNA (SEQ ID NO: 1) and NOS terminator (2) $El_2$35S promoter, *Torenia*-derived MT gene, full length cDNA (SEQ ID NO: 17) and NOS terminator (3) $El_2$35S promoter, *Torenia*-derived FNS gene, full length cDNA (SEQ ID NO: 19) and D8 terminator (4) $El_2$35S promoter, *Gentiana scabra*-derived CGT, full length cDNA (SEQ ID NO: 21) and *Arabidopsis*-derived HSP terminator This plasmid constitutively expresses the pansy F3'5'H #40 gene, the *Torenia* MT gene, the *Torenia* FNS gene, and the *Gentiana scabra* CGT gene.

The pSPB6438 constructed in this manner was introduced into an orange rose variety "Rita Perfumera" and a total of 122 transformants were obtained. Pigment analysis was carried out thereon and 71 transformants were confirmed to accumulate malvidin, and the maximum malvidin content thereof was 69.6% (average 25.9%). Furthermore, in this system, in addition to the isovitexin analyzed so far as the flavone C-glycoside, vitexin (apigenin 8-C-glucoside) and vicenin-2 (apigenin 6,8-C diglucoside) were also identified and quantified. Of the transformants in which malvidin could be detected, flavone C-glycoside could be confirmed in 16, and from the total amount thereof, the maximum amount produced per gram of fresh petals was 0.02 mg. In contrast thereto, the total amount of flavones (apigenin, luteolin, and tricetin) was a high content of 2.07 mg per gram of fresh petals.

Representative analysis values of the transformants are shown below in Table 9.

TABLE 9

| Plant | Mal | Anthocyanidin (mg/g) | | | | | Flavonol (mg/g) | | | Flavone (mg/g) | | | Flavone C-glycoside (mg/g) | | |
|---|---|---|---|---|---|---|---|---|---|---|---|---|---|---|---|
| No. | (%) | Del | Cya | Pet | Pel | Mal | M | Q | K | Tri | Lut | Api | Vic2 | VX | IVX |
| Host | 0.0 | 0.000 | 0.009 | 0.000 | 0.013 | 0.000 | 0.000 | 0.019 | 2.109 | 0.000 | 0.000 | 0.000 | 0.000 | 0.000 | 0.000 |
| 1 | 39.3 | 0.051 | 0.013 | 0.040 | 0.002 | 0.078 | 0.177 | 0.099 | 0.471 | 0.626 | 0.258 | 0.208 | 0.007 | 0.000 | 0.000 |
| 2 | 33.0 | 0.094 | 0.026 | 0.068 | 0.004 | 0.106 | 0.243 | 0.130 | 0.654 | 0.824 | 0.311 | 0.227 | 0.009 | 0.000 | 0.000 |
| 3 | 62.5 | 0.104 | 0.022 | 0.071 | 0.003 | 0.397 | 0.465 | 0.232 | 0.684 | 1.105 | 0.327 | 0.170 | 0.009 | 0.000 | 0.000 |
| 4 | 69.9 | 0.044 | 0.010 | 0.038 | 0.003 | 0.315 | 0.343 | 0.190 | 0.649 | 0.730 | 0.336 | 0.194 | 0.007 | 0.000 | 0.000 |
| 5 | 32.7 | 0.095 | 0.021 | 0.068 | 0.002 | 0.099 | 0.257 | 0.123 | 0.532 | 1.032 | 0.345 | 0.282 | 0.013 | 0.000 | 0.000 |
| 6 | 27.0 | 0.099 | 0.021 | 0.062 | 0.002 | 0.073 | 0.203 | 0.086 | 0.496 | 1.151 | 0.414 | 0.502 | 0.015 | 0.000 | 0.000 |
| 7 | 33.9 | 0.070 | 0.019 | 0.052 | 0.003 | 0.083 | 0.251 | 0.117 | 0.616 | 0.790 | 0.309 | 0.257 | 0.010 | 0.000 | 0.000 |
| 8 | 28.6 | 0.056 | 0.018 | 0.038 | 0.001 | 0.049 | 0.175 | 0.079 | 0.231 | 1.065 | 0.414 | 0.314 | 0.018 | 0.000 | 0.000 |
| 9 | 15.2 | 0.006 | 0.005 | 0.003 | 0.004 | 0.004 | 0.023 | 0.025 | 0.972 | 0.000 | 0.063 | 0.624 | 0.008 | 0.000 | 0.004 |
| 10 | 19.0 | 0.003 | 0.003 | 0.002 | 0.003 | 0.003 | 0.027 | 0.030 | 1.517 | 0.093 | 0.049 | 0.598 | 0.005 | 0.000 | 0.007 |
| 11 | 10.5 | 0.002 | 0.004 | 0.001 | 0.006 | 0.002 | 0.007 | 0.022 | 1.891 | 0.079 | 0.045 | 0.790 | 0.006 | 0.000 | 0.008 |
| 12 | 30.5 | 0.037 | 0.011 | 0.026 | 0.001 | 0.037 | 0.135 | 0.065 | 0.251 | 0.565 | 0.243 | 0.205 | 0.009 | 0.000 | 0.000 |
| 13 | 55.7 | 0.023 | 0.008 | 0.020 | 0.000 | 0.080 | 0.093 | 0.088 | 0.144 | 0.276 | 0.243 | 0.241 | 0.009 | 0.000 | 0.000 |

TABLE 9-continued

| Plant | Mal | Anthocyanidin (mg/g) | | | | | Flavonol (mg/g) | | | Flavone (mg/g) | | | Flavone C-glycoside (mg/g) | | |
|---|---|---|---|---|---|---|---|---|---|---|---|---|---|---|---|
| No. | (%) | Del | Cya | Pet | Pel | Mal | M | Q | K | Tri | Lut | Api | Vic2 | VX | IVX |
| 14 | 37.0 | 0.065 | 0.029 | 0.051 | 0.002 | 0.105 | 0.191 | 0.147 | 0.348 | 0.640 | 0.341 | 0.181 | 0.013 | 0.000 | 0.000 |
| 15 | 40.5 | 0.072 | 0.021 | 0.059 | 0.002 | 0.123 | 0.249 | 0.148 | 0.530 | 0.749 | 0.317 | 0.225 | 0.010 | 0.000 | 0.000 |
| 16 | 17.4 | 0.003 | 0.004 | 0.000 | 0.003 | 0.002 | 0.013 | 0.023 | 0.828 | 0.050 | 0.041 | 0.739 | 0.009 | 0.000 | 0.006 |

Host: Rita Perfumera
Del: Delphinidin, Cya: Cyanidin, Pet: Petunidin, Pel: Pelargonidin, Mal: Malvidin
M: Myricetin, Q: Quercetin, K: Kaempferol
Tri: Tricetin, Lut: Luteolin, Api: Apigenin, Vic2: Vicenin-2, VX: Vitexin, IVX: Isovitexin
Mal (%): Malvidin percentage of all anthocyanidins

Example 10: (Pathway 2) Introduction of *Campanula*-Derived F3'S"H Gene, *Torenia*-Derived MT Gene, *Torenia*-Derived FNS Gene, and *Gentiana scabra*-Derived CGT Gene into Rose Variety "Ocean Song"

pSPB7013 has the basic skeleton of pBINPLUS and contains the following 4 expression cassettes.

(1) El$_2$35S promoter, *Campanula*-derived F3'5'H, full length cDNA (SEQ ID NO:9) and D8 terminator (2) El$_2$35S promoter, *Torenia*-derived MT, full length cDNA (SEQ ID NO: 17) and NOS terminator (3) El$_2$35S promoter, *Torenia*-derived FNS, full length cDNA (SEQ ID NO: 19) and a D8 terminator (4) El$_2$35S promoter, *Gentiana scabra*-derived CGT, full length cDNA (SEQ ID NO:21) (*Arabidopsis* ADH gene-derived 5'-UTR (SEQ ID NO: 23) added to 5' end) and *Arabidopsis*-derived HSP terminator This plasmid constitutively expresses the *Campanula* F3'5'H gene, the *Torenia* MT gene, the *Torenia* FNS gene, and the *Gentiana scabra* CGT gene in plants.

The pSPB7013 constructed in this manner was introduced into a blue-hued rose variety "Ocean Song" and a total of 15 transformants were obtained. Pigment analysis was carried out thereon and all transformants were confirmed to accumulate malvidin, and the maximum malvidin content thereof was 67.2% (average 40.9%). Furthermore, in this system, in addition to the isovitexin, vitexin, and vicenin-2 analyzed so far as the flavone C-glycoside, isoorientin (luteolin 6-C-glucoside) and orientin (luteolin 8-C-glucoside) were also identified and quantified. Flavone C-glycoside could be detected in all of the transformants in which malvidin was detected, and from the total amount thereof, the maximum amount produced per gram of fresh petals was a high content of 1.410 mg.

Representative analysis values of the transformants are shown below in Table 10.

TABLE 10

| Plant | Mal | Anthocyanidin (mg/g) | | | | | Flavonol (mg/g) | | | Flavone (mg/g) | | | Flavone C-glycoside (mg/g) | | | | |
|---|---|---|---|---|---|---|---|---|---|---|---|---|---|---|---|---|---|
| No. | (%) | Del | Cya | Pet | Pel | Mal | M | Q | K | Tri | Lut | Api | Vic2 | VX | IVX | Ori | Iori |
| Host | 0.0 | 0.000 | 0.024 | 0.000 | 0.000 | 0.000 | 0.000 | 2.883 | 0.586 | 0.000 | 0.000 | 0.000 | 0.000 | 0.000 | 0.000 | 0.000 | 0.000 |
| 1 | 42.0 | 0.011 | 0.000 | 0.005 | 0.000 | 0.012 | 1.108 | 0.258 | 0.091 | 0.899 | 0.433 | 0.042 | 0.010 | 0.000 | 0.479 | 0.000 | 0.921 |
| 2 | 41.3 | 0.012 | 0.000 | 0.006 | 0.000 | 0.013 | 1.178 | 0.347 | 0.113 | 0.822 | 0.401 | 0.037 | 0.009 | 0.000 | 0.337 | 0.000 | 0.731 |
| 3 | 32.4 | 0.014 | 0.000 | 0.005 | 0.000 | 0.010 | 0.956 | 0.328 | 0.082 | 0.892 | 0.473 | 0.035 | 0.010 | 0.000 | 0.159 | 0.000 | 0.619 |
| 4 | 44.5 | 0.013 | 0.001 | 0.007 | 0.000 | 0.018 | 1.338 | 0.447 | 0.105 | 0.680 | 0.361 | 0.031 | 0.008 | 0.000 | 0.349 | 0.000 | 0.777 |
| 5 | 38.5 | 0.014 | 0.007 | 0.006 | 0.000 | 0.024 | 0.619 | 1.582 | 0.278 | 0.033 | 0.023 | 0.004 | 0.000 | 0.000 | 0.014 | 0.000 | 0.087 |
| 6 | 41.5 | 0.042 | 0.002 | 0.022 | 0.000 | 0.048 | 3.590 | 1.293 | 0.598 | 0.063 | 0.038 | 0.005 | 0.000 | 0.000 | 0.003 | 0.000 | 0.075 |
| 7 | 44.4 | 0.017 | 0.000 | 0.009 | 0.000 | 0.023 | 0.959 | 0.369 | 0.052 | 0.795 | 0.416 | 0.030 | 0.017 | 0.000 | 0.224 | 0.000 | 0.884 |
| 8 | 40.4 | 0.037 | 0.002 | 0.016 | 0.000 | 0.039 | 3.619 | 1.467 | 0.621 | 0.028 | 0.011 | 0.001 | 0.000 | 0.000 | 0.000 | 0.000 | 0.026 |
| 9 | 32.0 | 0.050 | 0.002 | 0.017 | 0.000 | 0.033 | 1.968 | 0.635 | 0.089 | 0.031 | 0.018 | 0.002 | 0.000 | 0.000 | 0.000 | 0.000 | 0.033 |
| 10 | 41.8 | 0.048 | 0.003 | 0.022 | 0.000 | 0.056 | 3.123 | 1.343 | 0.400 | 0.040 | 0.013 | 0.001 | 0.000 | 0.000 | 0.002 | 0.000 | 0.031 |
| 11 | 40.3 | 0.016 | 0.000 | 0.006 | 0.000 | 0.015 | 1.076 | 0.285 | 0.099 | 0.652 | 0.328 | 0.026 | 0.012 | 0.000 | 0.108 | 0.000 | 0.488 |
| 12 | 36.3 | 0.038 | 0.000 | 0.012 | 0.000 | 0.028 | 1.330 | 0.308 | 0.088 | 0.226 | 0.129 | 0.012 | 0.000 | 0.000 | 0.022 | 0.000 | 0.175 |
| 13 | 33.3 | 0.045 | 0.001 | 0.017 | 0.000 | 0.032 | 2.311 | 0.547 | 0.151 | 0.049 | 0.015 | 0.002 | 0.000 | 0.000 | 0.000 | 0.000 | 0.036 |
| 14 | 67.2 | 0.038 | 0.000 | 0.011 | 0.000 | 0.099 | 2.892 | 0.767 | 0.224 | 0.064 | 0.037 | 0.005 | 0.000 | 0.000 | 0.010 | 0.000 | 0.071 |
| 15 | 38.3 | 0.013 | 0.000 | 0.005 | 0.000 | 0.012 | 0.688 | 0.234 | 0.031 | 0.658 | 0.409 | 0.028 | 0.014 | 0.000 | 0.135 | 0.000 | 0.622 |

Host: Ocean Song
Del: Delphinidin, Cya: Cyanidin, Pet: Petunidin, Pel: Pelargonidin, Mal: Malvidin
M: Myricetin, Q: Quercetin, K: Kaempferol
Tri: Tricetin, Lut: Luteolin, Api: Apigenin, Vic2: Vicenin-2, VX: Vitexin, IVX: Isovitexin
Ori: Orientin, Iori: Isoorientin
Mal (%): Malvidin percentage of all anthocyanidins

Example 11: Evaluation of Flower Color of Roses Containing Flavone C-Glycoside The transformants (rose variety "Ocean Song" used as host) created in Examples 8 and 10 were categorized into groups, wherein: (1) delphinidin had accumulated as the main pigment but flavone was not present; (2) malvidin had accumulated as the main pigment and flavone C-glycoside created through pathway 1 was present; (3) malvidin had accumulated as the main pigment and flavone C-glycoside created through pathway 2 was present; and the host (wherein cyanidin had accumulated as the main pigment). The color of each of the petals thereof were measured using a spectrophotometer CM-2022 (Minolta Co., Ltd) with a 10-degree field of view and a D65 light source and analyzed using the color management software SpectraMagic™ (Minolta Co., Ltd.) (n=5).

Even in rose types in which the main pigment was delphinidin, the hue angle of the petals shifted towards blue. Furthermore, when flavone C-glycoside was made to coexist in rose types in which the main pigment was malvidin, this tendency was even more remarkable and the hue angle also greatly shifted to the blue side. The system of Example 10 was found to exhibit such a remarkable tendency. From the results above, it was confirmed that the color of petals turned more blue due to the coexistence of malvidin and flavone C-glycoside.

The results are shown in Table 11.

TABLE 11

| | Gene and flavonoid combination | Hue angle |
|---|---|---|
| Host | Ocean Song<br>Cyanidin accumulated as main pigment<br>Flavone C-glycoside not contained at all | Average 362.57° |
| | 1. *Campanula* F3'5'H<br>High accumulation of delphinidin as main pigment<br>Flavone C-glycoside not contained at all | Average 337.33°<br>Maximum blue value 333.15° |
| Example 8 | 2. *Campanula* F3'5'H + *Torenia* MT + *Glycyrrhiza* F2H + *Oryza sativa* CGT (codon-usage modified) + *Lotus japonicus* FDH<br>High accumulation of malvidin as main pigment<br>Flavone C-glycoside contained | Average 320.16°<br>Maximum blue value 318.89° |
| Example 10 | 3. *Campanula* F3'5'H + *Torenia* MT + *Torenia* FNS + *Gentiana scabra* CGT<br>High accumulation of malvidin as main pigment<br>Flavone C-glycoside contained | Average 313.75°<br>Maximum blue value 277.05° |

Example 12: (Pathway 1) Introduction of *Campanula*-Derived F3'5'H Gene, Lavender-Derived 3AT Gene, *Glycyrrhiza*-Derived F2H Gene, *Oryza sativa*-Derived Codon-Usage Modified CGT Gene, and *Lotus japonicus*-Derived FDH Gene into Rose Variety "Ocean Song"

pSPB6495 has the basic skeleton of pBINPLUS and contains the following 5 expression cassettes.

(1) $El_2$35S promoter, *Campanula*-derived F3'5'H, full length cDNA (SEQ ID NO: 9) and D8 terminator (2) $El_2$35S promoter, lavender-derived 3AT, full length cDNA (SEQ ID NO: 24) and *Arabidopsis*-derived HSP terminator (3) 35S promoter, *Glycyrrhiza*-derived F2H gene, full length cDNA (SEQ ID NO: 3) and *Perilla*-derived AT terminator (4) 35S promoter, *Oryza sativa*-derived codon-usage modified CGT, full length cDNA (SEQ ID NO: 13) and *Arabidopsis*-derived HSP terminator (5) 35S promoter, *Lotus japonicus*-derived FDH, full length cDNA (SEQ ID NO: 15) and *Arabidopsis*-derived HSP terminator This plasmid constitutively expresses the *Campanula* F3',5'H gene, the Lavender 3AT gene, the *Glycyrrhiza* F2H gene, the *Oryza sativa* codon-usage modified CGT gene, and the *Lotus japonicus* FDH gene in the plant.

The pSPB6495 constructed in this manner was introduced into a blue rose variety "Ocean song" and a total of 228 transformants were obtained. Pigment analysis was carried out thereon and 59 transformants were confirmed to accumulate acylated delphinidin. Furthermore, in this system, in addition to the isovitexin analyzed so far as the flavone C-glycoside, vitexin (apigenin 8-C-glucoside), vicenin-2 (apigenin 6,8-C-diglucoside), isoorientin (luteolin 6-C-glucoside), and orientin (luteolin 8-C-glucoside) were also identified and quantified. Flavone C-glycoside could be detected in all of the transformants in which acylated delphinidin was detected. There was a transformant having a high maximum amount thereof as high as from the total amount thereof, the maximum amount produced per gram of fresh petals included a transformant with a high content of 1.720 mg, but the average value was 0.833 mg.

Representative analysis values of the transformants are shown below in Table 12.

TABLE 12

| Plant | Del | Anthocyanidin (mg) | | | | | Flavonol (mg/g) | | | Flavone (mg/g) | | | Flavone C-glycoside (mg/g) | | | | |
|---|---|---|---|---|---|---|---|---|---|---|---|---|---|---|---|---|---|
| No. | (%) | Del | Cya | Pet | Pel | Mal | M | Q | K | Tri | Lut | Api | Vic2 | VX | IVX | Ori | Iori |
| 1 | 94.6 | 0.126 | 0.007 | 0.000 | 0.000 | 0.000 | 1.140 | 0.476 | 0.056 | 0.008 | 0.004 | 0.002 | 0.508 | 0.030 | 0.088 | 0.000 | 0.011 |
| 2 | 94.7 | 0.078 | 0.004 | 0.000 | 0.000 | 0.000 | 1.864 | 1.082 | 0.524 | 0.000 | 0.000 | 0.000 | 0.320 | 0.000 | 0.022 | 0.000 | 0.000 |
| 3 | 92.4 | 0.135 | 0.011 | 0.001 | 0.000 | 0.000 | 2.853 | 2.384 | 1.236 | 0.000 | 0.000 | 0.000 | 0.745 | 0.014 | 0.049 | 0.000 | 0.000 |
| 4 | 92.3 | 0.082 | 0.007 | 0.000 | 0.000 | 0.000 | 1.574 | 0.922 | 0.165 | 0.000 | 0.002 | 0.002 | 0.746 | 0.043 | 0.094 | 0.000 | 0.011 |
| 5 | 92.7 | 0.077 | 0.006 | 0.001 | 0.000 | 0.000 | 1.398 | 0.700 | 0.142 | 0.000 | 0.000 | 0.000 | 0.575 | 0.033 | 0.102 | 0.000 | 0.012 |
| 6 | 93.6 | 0.117 | 0.008 | 0.000 | 0.000 | 0.000 | 1.683 | 0.934 | 0.131 | 0.000 | 0.001 | 0.001 | 0.779 | 0.034 | 0.105 | 0.000 | 0.014 |
| 7 | 92.9 | 0.091 | 0.007 | 0.001 | 0.000 | 0.000 | 1.415 | 0.637 | 0.086 | 0.000 | 0.001 | 0.000 | 0.637 | 0.027 | 0.059 | 0.000 | 0.007 |
| 8 | 92.1 | 0.090 | 0.008 | 0.001 | 0.000 | 0.000 | 1.121 | 0.692 | 0.147 | 0.000 | 0.000 | 0.000 | 0.461 | 0.015 | 0.060 | 0.000 | 0.000 |
| 9 | 91.7 | 0.096 | 0.009 | 0.000 | 0.000 | 0.000 | 2.380 | 1.311 | 0.296 | 0.006 | 0.005 | 0.010 | 0.594 | 0.065 | 0.139 | 0.000 | 0.015 |

TABLE 12-continued

| Plant No. | Del (%) | Anthocyanidin (mg) Del | Cya | Pet | Pel | Mal | Flavonol (mg/g) M | Q | K | Flavone (mg/g) Tri | Lut | Api | Flavone C-glycoside (mg/g) Vic2 | VX | IVX | Ori | Iori |
|---|---|---|---|---|---|---|---|---|---|---|---|---|---|---|---|---|---|
| 10 | 94.1 | 0.098 | 0.006 | 0.001 | 0.000 | 0.000 | 2.300 | 1.122 | 0.241 | 0.000 | 0.001 | 0.000 | 0.698 | 0.030 | 0.096 | 0.000 | 0.009 |
| 11 | 95.7 | 0.093 | 0.004 | 0.000 | 0.000 | 0.000 | 1.765 | 0.703 | 0.120 | 0.000 | 0.008 | 0.010 | 0.654 | 0.030 | 0.103 | 0.000 | 0.015 |
| 12 | 95.8 | 0.078 | 0.003 | 0.000 | 0.000 | 0.000 | 1.783 | 0.682 | 0.126 | 0.000 | 0.007 | 0.011 | 0.614 | 0.041 | 0.117 | 0.000 | 0.016 |
| 13 | 100.0 | 0.073 | 0.000 | 0.000 | 0.000 | 0.000 | 2.114 | 0.320 | 0.041 | 0.000 | 0.010 | 0.007 | 0.405 | 0.052 | 0.126 | 0.000 | 0.023 |
| 14 | 100.0 | 0.076 | 0.000 | 0.000 | 0.000 | 0.000 | 2.593 | 0.267 | 0.037 | 0.000 | 0.032 | 0.025 | 0.636 | 0.174 | 0.346 | 0.019 | 0.064 |
| 15 | 100.0 | 0.085 | 0.000 | 0.000 | 0.000 | 0.000 | 2.262 | 0.301 | 0.049 | 0.000 | 0.032 | 0.022 | 0.710 | 0.122 | 0.317 | 0.017 | 0.060 |
| 16 | 93.9 | 0.072 | 0.005 | 0.001 | 0.000 | 0.000 | 1.373 | 0.583 | 0.093 | 0.000 | 0.000 | 0.000 | 0.573 | 0.020 | 0.065 | 0.000 | 0.006 |
| 17 | 91.4 | 0.094 | 0.009 | 0.001 | 0.000 | 0.000 | 1.236 | 0.734 | 0.087 | 0.000 | 0.000 | 0.000 | 0.485 | 0.015 | 0.048 | 0.000 | 0.000 |
| 18 | 97.4 | 0.100 | 0.003 | 0.001 | 0.000 | 0.000 | 1.764 | 0.808 | 0.302 | 0.000 | 0.000 | 0.000 | 0.481 | 0.013 | 0.082 | 0.000 | 0.006 |
| 19 | 95.6 | 0.097 | 0.005 | 0.000 | 0.000 | 0.000 | 2.792 | 1.657 | 0.410 | 0.000 | 0.008 | 0.015 | 0.575 | 0.029 | 0.117 | 0.000 | 0.014 |
| 20 | 97.2 | 0.088 | 0.003 | 0.001 | 0.000 | 0.000 | 1.858 | 0.573 | 0.131 | 0.000 | 0.001 | 0.001 | 0.763 | 0.018 | 0.069 | 0.000 | 0.009 |
| 21 | 96.9 | 0.101 | 0.003 | 0.001 | 0.000 | 0.000 | 2.990 | 1.293 | 0.424 | 0.000 | 0.001 | 0.000 | 0.846 | 0.017 | 0.093 | 0.000 | 0.007 |
| 22 | 96.8 | 0.090 | 0.003 | 0.001 | 0.000 | 0.000 | 2.171 | 0.728 | 0.173 | 0.000 | 0.000 | 0.000 | 0.662 | 0.011 | 0.047 | 0.000 | 0.000 |
| 23 | 96.6 | 0.100 | 0.003 | 0.000 | 0.000 | 0.000 | 3.097 | 1.561 | 0.484 | 0.000 | 0.008 | 0.019 | 0.650 | 0.026 | 0.103 | 0.000 | 0.010 |
| 24 | 93.6 | 0.073 | 0.005 | 0.000 | 0.000 | 0.000 | 1.506 | 0.687 | 0.074 | 0.000 | 0.000 | 0.000 | 0.633 | 0.020 | 0.058 | 0.000 | 0.006 |
| 25 | 93.4 | 0.074 | 0.005 | 0.000 | 0.000 | 0.000 | 1.292 | 0.683 | 0.075 | 0.000 | 0.004 | 0.003 | 0.491 | 0.017 | 0.055 | 0.000 | 0.007 |
| 26 | 90.2 | 0.093 | 0.010 | 0.000 | 0.000 | 0.000 | 2.371 | 1.426 | 0.279 | 0.000 | 0.001 | 0.000 | 0.777 | 0.021 | 0.071 | 0.000 | 0.004 |
| 27 | 90.3 | 0.104 | 0.011 | 0.000 | 0.000 | 0.000 | 1.766 | 1.172 | 0.190 | 0.000 | 0.001 | 0.000 | 0.786 | 0.020 | 0.055 | 0.000 | 0.004 |
| 28 | 90.8 | 0.100 | 0.010 | 0.001 | 0.000 | 0.000 | 2.273 | 1.494 | 0.278 | 0.000 | 0.001 | 0.000 | 0.760 | 0.024 | 0.078 | 0.000 | 0.006 |
| 29 | 91.2 | 0.097 | 0.009 | 0.000 | 0.000 | 0.000 | 1.680 | 1.113 | 0.225 | 0.000 | 0.000 | 0.000 | 0.579 | 0.012 | 0.035 | 0.000 | 0.004 |
| 30 | 94.0 | 0.099 | 0.006 | 0.000 | 0.000 | 0.000 | 1.623 | 0.941 | 0.184 | 0.000 | 0.001 | 0.000 | 0.811 | 0.024 | 0.070 | 0.000 | 0.007 |
| 31 | 92.0 | 0.091 | 0.008 | 0.001 | 0.000 | 0.000 | 1.379 | 0.814 | 0.116 | 0.000 | 0.002 | 0.000 | 0.749 | 0.019 | 0.073 | 0.000 | 0.007 |
| 32 | 92.2 | 0.088 | 0.008 | 0.001 | 0.000 | 0.000 | 1.402 | 0.767 | 0.102 | 0.000 | 0.001 | 0.000 | 0.880 | 0.023 | 0.085 | 0.000 | 0.007 |
| 33 | 93.2 | 0.072 | 0.005 | 0.001 | 0.000 | 0.000 | 1.919 | 1.105 | 0.302 | 0.000 | 0.001 | 0.000 | 0.707 | 0.026 | 0.086 | 0.000 | 0.006 |
| 34 | 93.4 | 0.104 | 0.007 | 0.001 | 0.000 | 0.000 | 1.572 | 0.781 | 0.103 | 0.000 | 0.002 | 0.000 | 0.900 | 0.047 | 0.158 | 0.000 | 0.017 |
| 35 | 91.4 | 0.099 | 0.009 | 0.000 | 0.000 | 0.000 | 1.550 | 1.028 | 0.160 | 0.000 | 0.008 | 0.009 | 0.752 | 0.047 | 0.166 | 0.000 | 0.020 |
| 36 | 90.9 | 0.113 | 0.011 | 0.001 | 0.000 | 0.000 | 1.607 | 1.118 | 0.212 | 0.000 | 0.000 | 0.000 | 0.752 | 0.014 | 0.072 | 0.000 | 0.000 |
| 37 | 95.7 | 0.067 | 0.003 | 0.000 | 0.000 | 0.000 | 1.938 | 0.695 | 0.123 | 0.000 | 0.010 | 0.016 | 0.706 | 0.071 | 0.156 | 0.000 | 0.020 |
| 38 | 91.1 | 0.089 | 0.009 | 0.001 | 0.000 | 0.000 | 2.127 | 1.346 | 0.263 | 0.000 | 0.011 | 0.015 | 0.693 | 0.069 | 0.151 | 0.000 | 0.016 |
| 39 | 96.0 | 0.097 | 0.004 | 0.000 | 0.000 | 0.000 | 2.271 | 1.100 | 0.244 | 0.000 | 0.003 | 0.005 | 0.560 | 0.021 | 0.063 | 0.000 | 0.005 |
| 40 | 95.2 | 0.094 | 0.005 | 0.000 | 0.000 | 0.000 | 1.396 | 0.541 | 0.105 | 0.000 | 0.012 | 0.014 | 0.540 | 0.120 | 0.338 | 0.000 | 0.040 |
| 41 | 97.7 | 0.076 | 0.002 | 0.000 | 0.000 | 0.000 | 2.413 | 0.859 | 0.236 | 0.011 | 0.013 | 0.023 | 0.590 | 0.019 | 0.073 | 0.000 | 0.010 |
| 42 | 100.0 | 0.074 | 0.000 | 0.000 | 0.000 | 0.000 | 1.947 | 0.358 | 0.072 | 0.000 | 0.007 | 0.007 | 0.618 | 0.043 | 0.121 | 0.000 | 0.023 |
| 43 | 94.7 | 0.069 | 0.004 | 0.000 | 0.000 | 0.000 | 1.621 | 0.692 | 0.146 | 0.000 | 0.001 | 0.000 | 0.704 | 0.015 | 0.055 | 0.000 | 0.000 |
| 44 | 93.9 | 0.081 | 0.005 | 0.001 | 0.000 | 0.000 | 1.528 | 0.648 | 0.093 | 0.000 | 0.001 | 0.000 | 0.586 | 0.017 | 0.054 | 0.000 | 0.000 |
| 45 | 95.6 | 0.078 | 0.004 | 0.000 | 0.000 | 0.000 | 1.692 | 0.672 | 0.156 | 0.000 | 0.001 | 0.000 | 0.673 | 0.021 | 0.055 | 0.000 | 0.007 |
| 46 | 95.2 | 0.112 | 0.006 | 0.000 | 0.000 | 0.000 | 1.958 | 0.851 | 0.202 | 0.000 | 0.001 | 0.000 | 0.794 | 0.023 | 0.069 | 0.000 | 0.007 |
| 47 | 97.4 | 0.106 | 0.003 | 0.001 | 0.000 | 0.000 | 3.277 | 1.210 | 0.472 | 0.000 | 0.000 | 0.000 | 0.661 | 0.018 | 0.085 | 0.000 | 0.007 |
| 48 | 97.5 | 0.120 | 0.003 | 0.000 | 0.000 | 0.000 | 2.848 | 1.063 | 0.341 | 0.000 | 0.001 | 0.000 | 0.976 | 0.016 | 0.095 | 0.000 | 0.010 |
| 49 | 94.8 | 0.130 | 0.007 | 0.001 | 0.000 | 0.000 | 1.815 | 0.798 | 0.146 | 0.000 | 0.000 | 0.000 | 0.855 | 0.020 | 0.086 | 0.000 | 0.010 |
| 50 | 91.1 | 0.074 | 0.007 | 0.001 | 0.000 | 0.000 | 1.620 | 0.907 | 0.163 | 0.000 | 0.001 | 0.000 | 0.640 | 0.015 | 0.047 | 0.000 | 0.000 |
| 51 | 91.2 | 0.085 | 0.008 | 0.000 | 0.000 | 0.000 | 2.123 | 1.204 | 0.163 | 0.000 | 0.001 | 0.001 | 0.665 | 0.037 | 0.092 | 0.000 | 0.009 |
| 52 | 92.5 | 0.091 | 0.007 | 0.000 | 0.000 | 0.000 | 1.908 | 1.074 | 0.238 | 0.000 | 0.001 | 0.001 | 0.638 | 0.025 | 0.052 | 0.000 | 0.005 |
| 53 | 93.1 | 0.097 | 0.007 | 0.000 | 0.000 | 0.000 | 2.411 | 1.360 | 0.322 | 0.000 | 0.000 | 0.000 | 0.701 | 0.028 | 0.048 | 0.000 | 0.000 |
| 54 | 100.0 | 0.052 | 0.000 | 0.000 | 0.000 | 0.000 | 3.621 | 0.476 | 0.106 | 0.000 | 0.000 | 0.000 | 1.148 | 0.216 | 0.325 | 0.000 | 0.031 |

Host: Ocean Song

Del: Delphinidin, Cya: Cyanidin, Pet: Petunidin, Pel: Pelargonidin, Mal: Malvidin M: Myricetin, Q, Quercetin, K: Kaempferol Tri: Tricetin, Lut: Luteolin, Api: Apigenin, Vic2: Vicenin-2, VX: Vitexin, IVX: Isovitexin Ori: Orientin, Iori: Isoorientin Del (%): Delphinidin percentage of all anthocyandidins Example 13: (Pathway 1) Introduction of *Campanula*-Derived F3'S'H Gene, *Clitoria Ternatea*-Derived 3’s'GT Gene, Rose-Derived 53GT(RNAi) Gene, *Perilla*-Derived 3GT Gene, Dahlia-Derived 3 Malonyl Transferase (MaT) Gene, *Glycyrrhiza*-Derived F2H Gene, *Oryza sativa*-Derived Codon-Usage Modified CGT Gene, and *Lotus japonicus* FDH Gene into Rose Variety “Ocean Song”

pSPB7189 has the basic skeleton of pBINPLUS and contains the following 5 expression cassettes.

(1) $El_2$35S promoter, *Campanula*-derived F3'S'H, full length cDNA (SEQ ID NO:9) and NOS terminator (2) $El_2$35S promoter, *Clitoria ternatea*-derived A3’S'GT, full length cDNA (SEQ ID NO: 26) and *Arabidopsis*-derived HSP terminator (3) $El_2$35S promoter, Rose-derived 53GT, full length cDNA (SEQ ID NO: 28) (RNAi), and *Arabidopsis*-derived HSP terminator (4) SAT promoter and *Perilla*-derived 3GT, full length cDNA (SEQ ID NO: 30), and *Arabidopsis*-derived HSP terminator (5) $El_2$35S promoter, Dahlia-derived 3MaT, full length cDNA (SEQ ID NO: 32), and *Arabidopsis*-derived HSP terminator (6) 35S promoter, *Glycyrrhiza*-derived F2H, full length cDNA (SEQ ID NO: 3), and *Perilla*-derived AT terminator (7) 35S promoter, *Oryza sativa*-derived codon-usage modified CGT, full length cDNA (SEQ ID NO: 13), and *Arabidopsis*-derived HSP terminator (8) 35S promoter, *Lotus japonicus*-derived FDH, full length cDNA (SEQ ID NO: 15), and *Arabidopsis*-derived HSP terminator.

This plasmid constitutively expresses the *Campanula* F3'5'H gene, the *Clitoria ternatea* A3',5'GT gene, the *Perilla* 3GT gene, the Dahlia 3MaT gene, the *Glycyrrhiza* F2H gene, the *Oryza sativa* codon-usage modified CGT gene, and the *Lotus japonicus* FDH gene, and inhibits expression of the endogenous Rose 5,3GT gene in plants.

The pSPB7189 constructed in this manner was introduced into a blue-hued rose variety “Ocean Song” and a total of 101 transformants were obtained. Pigment analysis was carried out thereon and only 1 transformant was confirmed to accumulate delphinidin, and acylation thereof was not confirmed. Furthermore, in this system, in addition to the isovitexin used so far as the flavone C-glycoside, vitexin (apigenin 8-C-glucoside), vicenin-2 (apigenin 6,8-C-diglucoside), isoorientin (luteolin 6-C-glucoside), and orientin (luteolin 8-C-glucoside) were also identified and quantified. Flavone C-glycoside could be detected in this transformant, and from the total amount thereof, the amount produced per gram of fresh petals was a high content of 1.024 mg. Analyzed values of the transformants are shown below in Table 13.

TABLE 13

| Plant | Del | Anthocyanidin (mg/g) | | | | | Flavonol (mg/g) | | | Flavone (mg/g) | | | Flavone C-glycoside (mg/g) | | | | |
|---|---|---|---|---|---|---|---|---|---|---|---|---|---|---|---|---|---|
| No. | (%) | Del | Cya | Pet | Pel | Mal | M | Q | K | Tri | Lut | Api | Vic2 | VX | IVX | Ori | Iori |
| 1 | 100.0 | 0.068 | 0.000 | 0.000 | 0.000 | 0.000 | 2.522 | 0.321 | 0.122 | 0.012 | 0.010 | 0.016 | 0.607 | 0.135 | 0.225 | 0.012 | 0.045 |

Host: Ocean Song

Del: Delphinidin, Cya: Cyanidin, Pet: Petunidin, Pel: Pelargonidin, Mal: Malvidin M: Myricetin, Q: Quercetin, K: Kaempferol Tri: Tricetin, Lut: Luteolin, Api: Apigenin, Vic2: Vicenin-2, VX: Vitexin, IVX: Isovitexin, Ori: Orientin, Iori: Isoorientin Del (%): Delphinidin percentage of all anthocyanidins Example 14: Evaluation of Flower Color of Roses Containing Flavone C-Glycoside The transformants (rose variety "Ocean Song" used as host) created in Examples 12 and 13 were categorized into groups, wherein: (1) delphinidin (a portion of which was acylated) had accumulated as the main pigment and flavone C-glycoside had been created through pathway 1; and (2) delphinidin had accumulated as the main pigment and flavone C-glycoside had been created through pathway 1. The color of each petal was measured using a spectrophotometer CM-2022 (Minolta Co., Ltd) with a 10-degree field of view and a D65 light source and analyzed using the color management software SpectraMagic™ (Minolta Co., Ltd.) (n=5).

For rose types in which the main pigment was delphinidin, even if a portion thereof was acylated, the hue angle of the petals was not confirmed to shift towards blue compared to transformants created in Examples 8 and 10 (however, there was a greater blue shift than for acylated anthocyanin alone). From the results above, it was confirmed that the color of petals turned more blue due to the coexistence of malvidin and flavone C-glycoside.

The results are shown in Table 14.

TABLE 14

| | Gene and flavonoid combination | Hue angle |
|---|---|---|
| Example 12 | 4. *Campanula* F3'5'H + Lavender-3AT + *Glycyrrhiza* F2H + *Oryza sativa* CGT (codon-usage modified) + *Lotus japonicus* FDH Delphinidin (a portion of which is acylated) accumulated as main pigment, flavone C-glycoside contained | Average 332.56° Maximum blue value 329.42° |
| Example 13 | 5. *Campanula* F3'5'H + *Clitoria ternatea* A3'5'GT + Rose 5,3GT(RNAi) + *Perilla* 3GT + *Dahlia* 3MaT + *Glycyrrhiza* F2H + *Oryza sativa* CGT (codon-usage modified) + *Lotus japonicus* FDH Delphinidin accumulated as main pigment, flavone C-glycoside contained | 342.66° |

The invention claimed is:

1. A method for creating a transformed rose plant or an inbred or an outbred progeny thereof, a propagule thereof, a part thereof, a tissue or a cell of the transformed rose plant or the inbred or the outbred progeny thereof, comprising the step of transforming a rose of Ocean Song variety so that a delphinidin-type anthocyanin coexists with a flavone C-glycoside in a cell of the rose plant, wherein the flavone C-glycoside is selected from the group consisting of flavone 6-C-glucoside, flavone 8-C-glucoside, and a combination thereof, wherein the transforming step is carried out by:

(a) introducing into the cell of the rose:

(i) a flavone synthase (FNS) gene encoding an FNS having at least 90% sequence identity to SEQ ID NO: 20;

(ii) a first flavone C-glucosyltransferase (CGT) gene encoding a CGT having at least 90% sequence identity to SEQ ID NO: 22, wherein an *Arabidopsis* alcohol dehydrogenase (ADH) gene-derived 5' untranslated region (5'-UTR) (SEQ ID NO: 23) has been operably linked to the 5' end of the CGT gene;

(iii) a flavonoid 3',5'-hydroxylase (F3'5'H) gene encoding an F3'5'H having at least 90% sequence identity to SEQ ID NO: 10; and (iv) a methyltransferase (MT) gene encoding an MT having at least 90% sequence identity to SEQ ID NO: 18, or (b) introducing into the cell of the rose:

(i) a flavanone 2-hydroxylase (F2H) gene encoding an F2H having at least 90% sequence identity to SEQ ID NO: 4;

(ii) a second flavone C-glucosyltransferase (CGT) gene encoding a CGT having at least 90% sequence identity to SEQ ID NO: 14;

(iii) a dehydratase (FDH) gene encoding an FDH having at least 90% sequence identity to SEQ ID NO: 16;

(iv) a flavonoid 3',5'-hydroxylase (F3'5'H) gene encoding an F3'5'H having at least 90% sequence identity to SEQ ID NO: 10; and (v) a methyltransferase (MT) gene encoding an MT having at least 90% sequence identity to SEQ ID NO: 18, wherein the transformed rose plant or inbred or outbred progeny thereof has a flower color belonging to the Blue group or Violet-Blue group of the RHS color chart and/or a hue angle of 339.7° to 270.0° in the CIE L*a*b* color system.

2. The method according to claim 1, wherein the flavone C-glycoside is apigenin 6-C-glucoside and/or luteolin 6-C-glucoside.

3. The method according to claim 1, wherein the delphinidin-type anthocyanin is selected from the group consisting of malvidin 3,5-diglucoside, delphinidin 3,5-diglucoside, petunidin 3,5-diglucoside, acylated anthocyanins, and combinations thereof.

4. The method according to claim 1, wherein the transforming step is carried out by introducing into the cell of the rose a vector comprising the FNS gene and the first CGT gene.

5. The method according to claim 4, wherein the vector further comprises the F3'5'H gene and the MT gene.

6. The method according to claim 5, wherein:

the FNS gene encodes an FNS having at least 95% sequence identity to SEQ ID NO: 20;

the first CGT gene encodes a CGT having at least 95% sequence identity to SEQ ID NO: 22;

the F3'5'H gene encodes an F3'5'H having at least 95% sequence identity to SEQ ID NO: 10;

the MT gene encodes an MT having at least 95% sequence identity to SEQ ID NO: 18.

7. The method according to claim 1, wherein the transforming step is carried out by introducing into the cell of the rose a vector comprising the F2H gene, the second CGT gene, and the FDH gene.

8. The method according to claim 7, wherein the vector further comprises the F3'5'H gene and the MT gene.

9. The method according to claim 8, wherein:

the F2H gene encodes an F2H having at least 95% sequence identity to SEQ ID NO: 4;

the second CGT gene encodes a CGT having at least 95% sequence identity to SEQ ID NO: 14;

the FDH gene encodes an FDH having at least 95% sequence identity to SEQ ID NO: 16;

the F3'5'H gene encodes a F3'5'H having at least 95% sequence identity to SEQ ID NO: 10; and the MT gene encodes an MT having at least 95% sequence identity to SEQ ID NO: 18.

10. A transformed rose plant or an inbred or an outbred progeny thereof, a propagule thereof, a part thereof, a tissue or a cell of the transformed rose plant or the inbred or the outbred progeny thereof, comprising:

(a) a flavone synthase (FNS) gene encoding an FNS having at least 90% sequence identity to SEQ ID NO: 20, a first flavone C-glucosyltransferase (CGT) gene encoding a CGT having at least 90% sequence identity to SEQ ID NO: 22, wherein an *Arabidopsis* alcohol dehydrogenase (ADH) gene-derived 5' untranslated region (5'-UTR) (SEQ ID NO: 23) has been operably linked to the 5' end of the CGT gene, a flavonoid 3',5'-hydroxylase (F3'5'H) gene encoding an F3'5'H having at least 90% sequence identity to SEQ ID NO: 10, and a methyltransferase (MT) gene encoding an MT having at least 90% sequence identity to SEQ ID NO: 18; or (b) a flavanone 2-hydroxylase (F2H) gene encoding an F2H having at least 90% sequence identity to SEQ ID NO: 4, a second flavone C-glucosyltransferase (CGT) gene encoding a CGT having at least 90% sequence identity to SEQ ID NO: 14, a dehydratase (FDH) gene encoding a FDH having at least 90% sequence identity to SEQ ID NO: 16, a flavonoid 3',5'-hydroxylase (F3'5'H) gene encoding an F3'5'H having at least 90% sequence identity to SEQ ID NO: 10, and a methyltransferase (MT) gene encoding an MT having at least 90% sequence identity to SEQ ID NO: 18, so that a delphinidin-type anthocyanin coexists with a flavone C-glycoside in a cell of the rose plant, wherein the flavone C-glycoside is selected from the group consisting of flavone 6-C-glucoside, flavone 8-C glucoside, and a combination thereof, wherein the transformed rose plant is obtained from a rose of Ocean Song variety, and wherein the transformed rose plant or inbred or outbred progeny thereof has a flower color belonging to the Blue group or Violet-Blue group of the RHS color chart and/or a hue angle of 339.7° to 270.0° in the CIE L*a*b* color system.

11. The transformed rose plant or the inbred or the outbred progeny thereof, the propagule thereof, the part thereof, the tissue or the cell of the transformed rose plant or the inbred or the outbred progeny thereof according to claim 10, wherein the flavone C-glycoside is apigenin 6-C-glucoside.

12. The transformed rose plant or the inbred or the outbred progeny thereof, the propagule thereof, the part thereof, the tissue or the cell of the transformed rose plant or the inbred or the outbred progeny thereof according to claim 10, wherein the delphinidin-type anthocyanin is selected from the group consisting of malvidin 3,5-diglucoside, delphinidin 3,5-diglucoside, petunidin 3,5-diglucoside, and acylated anthocyanins, and combinations thereof.

13. The transformed rose plant or inbred or outbred progeny thereof according to claim 10, wherein:

the FNS gene encodes an FNS having at least 95% sequence identity to SEQ ID NO: 20;

the first CGT gene encodes a CGT having at least 95% sequence identity to SEQ ID NO: 22;

the F3'5'H gene encodes an F3'5'H having at least 95% sequence identity to SEQ ID NO: 10;

the MT gene encodes an MT having at least 95% sequence identity to SEQ ID NO: 18.

14. The transformed rose plant or the inbred or the outbred progeny thereof, the propagule thereof, the part thereof, the tissue or the cell of the transformed rose plant or the inbred or the outbred progeny thereof according to claim 10, wherein:

the F2H gene encodes an F2H having at least 95% sequence identity to SEQ ID NO: 4;

the second CGT gene encodes a CGT having at least 95% sequence identity to SEQ ID NO: 14;

the FDH gene encodes an FDH having at least 95% sequence identity to SEQ ID NO: 16;

the F3'5'H gene encodes an F3'5'H having at least 95% sequence identity to SEQ ID NO: 10; and the MT gene encodes an MT having at least 95% sequence identity to SEQ ID NO: 18.

15. The propagule, the part, the tissue, or the cell of the transformed rose plant or the inbred or the outbred progeny thereof according to claim 10.

16. A cut flower of the transformed rose plant or the inbred or the outbred progeny thereof according to claim 10, or a processed product created from the cut flower.

17. A vector comprising (a) a flavone synthase (FNS) gene encoding an FNS having at least 90% sequence identity to SEQ ID NO: 20; (b) a first flavone C-glucosyltransferase (CGT) gene (i) encoding a CGT having at least 90% sequence identity to SEQ ID NO: 22 and (ii) further comprising an operably linked *Arabidopsis* alcohol dehydrogenase (ADH) gene-derived 5' untranslated region (5'-UTR) (SEQ ID NO: 23); (c) a flavonoid 3',5'-hydroxylase (F3'5'H) gene encoding an F3'5'H having at least 90% sequence identity SEQ ID NO: 10; and (d) a methyltransferase (MT) gene encoding an MT having at least 90% sequence identity SEQ ID NO: 18.

18. A vector comprising (a) a flavanone 2-hydroxylase (F2H) gene encoding an F2H having at least 90% sequence identity to SEQ ID NO: 4; (b) a second flavone C-glucosyltransferase (CGT) gene encoding a CGT having at least 90% sequence identity to SEQ ID NO: 14; (c) a dehydratase (FDH) gene encoding an FDH having at least 90% sequence identity to SEQ ID NO: 16; (d) a flavonoid 3',5'-hydroxylase (F3'5'H) gene encoding an F3'5'H having at least 90% sequence identity to SEQ ID NO: 10; and (e) a methyltransferase (MT) gene encoding an MT having at least 90% sequence identity to SEQ ID NO: 18.

* * * * *